(12) United States Patent
Blackadar et al.

(10) Patent No.: US 9,734,304 B2
(45) Date of Patent: Aug. 15, 2017

(54) VERSATILE SENSORS WITH DATA FUSION FUNCTIONALITY

(71) Applicant: LumiraDx UK Ltd., London (GB)

(72) Inventors: Thomas P. Blackadar, Natick, MA (US); David P. Monahan, West Chester, PA (US)

(73) Assignee: LUMIRADX UK LTD, London (GB)

( * ) Notice: Subject to any disclaimer, the term of this patent is extended or adjusted under 35 U.S.C. 154(b) by 0 days.

(21) Appl. No.: 13/840,098

(22) Filed: Mar. 15, 2013

(65) Prior Publication Data

US 2013/0217979 A1   Aug. 22, 2013

Related U.S. Application Data

(63) Continuation-in-part of application No. 13/690,313, filed on Nov. 30, 2012.
(Continued)

(51) Int. Cl.
*A61B 5/1455* (2006.01)
*G06F 19/00* (2011.01)
(Continued)

(52) U.S. Cl.
CPC ............ *G06F 19/36* (2013.01); *A61B 5/0024* (2013.01); *A61B 5/0205* (2013.01);
(Continued)

(58) Field of Classification Search
CPC . A61B 5/1455; A61B 5/14532; A61B 5/0002; A61B 5/0059; A61B 5/14551;
(Continued)

(56) References Cited

U.S. PATENT DOCUMENTS

| 3,797,010 A | 3/1974 | Adler et al. |
| 3,943,918 A | 3/1976 | Lewis |

(Continued)

FOREIGN PATENT DOCUMENTS

| EP | 0 209 804 A2 | 1/1987 |
| EP | 0 770 349 A1 | 5/1997 |

(Continued)

OTHER PUBLICATIONS

Invitation to Pay Additional Fees for PCT Application No. PCT/US2012/067310, mailed Mar. 13, 2013.
(Continued)

*Primary Examiner* — Eric Winakur
*Assistant Examiner* — Chu Chuan (JJ) Liu
(74) *Attorney, Agent, or Firm* — Pierce Atwood LLP

(57) ABSTRACT

Apparatuses and methods are disclosed for identifying with a single, small, intelligent activity monitor a particular type of activity from among a plurality of different activities. The monitor may include a multi-axis accelerometer and microcontroller configured to combine and process accelerometer data so as to generate features representative of an activity. The features may be processed to identify a particular activity (e.g., running, biking, swimming) from among a plurality of different activities that may include activities not performed by a human subject. An intelligent activity monitor may be configured to operate as a versatile sensor, or to operate in combination with a versatile sensor, to further receive and process physiological data and compute a fitness metric for a subject.

33 Claims, 19 Drawing Sheets

Related U.S. Application Data

(60) Provisional application No. 61/566,528, filed on Dec. 2, 2011.

(51) Int. Cl.
*A61B 5/0205* (2006.01)
*A61B 5/00* (2006.01)
*A61B 5/145* (2006.01)
*A61B 5/11* (2006.01)
*G01C 22/00* (2006.01)

(52) U.S. Cl.
CPC .......... *A61B 5/1118* (2013.01); *A61B 5/1123* (2013.01); *A61B 5/14532* (2013.01); *A61B 5/14551* (2013.01); *A61B 5/6823* (2013.01); *A61B 5/6824* (2013.01); *A61B 5/6828* (2013.01); *A61B 5/6829* (2013.01); *A61B 5/7264* (2013.01); *A61B 5/7239* (2013.01); *A61B 5/742* (2013.01); *A61B 2560/0209* (2013.01); *A61B 2562/0219* (2013.01); *G01C 22/006* (2013.01)

(58) Field of Classification Search
CPC ..... A61B 5/14552; A61B 5/68; A61B 5/6823; A61B 5/6824; A61B 5/6828; A61B 5/6829; A61B 5/0205
USPC ....... 600/300, 476, 301, 310, 316, 322, 323, 600/331, 333, 340, 344, 473; 356/41; 435/24
See application file for complete search history.

(56) References Cited

U.S. PATENT DOCUMENTS

| | | |
|---|---|---|
| 4,141,367 A | 2/1979 | Ferreira |
| 4,578,769 A | 3/1986 | Frederick |
| 4,791,933 A | 12/1988 | Asai et al. |
| 4,800,894 A | 1/1989 | Milani |
| 4,957,109 A | 9/1990 | Groeger et al. |
| 4,958,645 A | 9/1990 | Cadell et al. |
| 4,974,607 A | 12/1990 | Miwa |
| 5,125,405 A | 6/1992 | Schmid |
| 5,257,631 A | 11/1993 | Wilk |
| 5,294,928 A | 3/1994 | Cooper et al. |
| 5,305,746 A | 4/1994 | Fendrock |
| 5,309,918 A | 5/1994 | Schraag |
| 5,319,363 A | 6/1994 | Welch et al. |
| 5,458,122 A | 10/1995 | Hethuin |
| 5,464,021 A | 11/1995 | Birnbaum |
| 5,515,735 A | 5/1996 | Sarihan |
| 5,538,007 A | 7/1996 | Gorman |
| 5,544,661 A | 8/1996 | Davis et al. |
| 5,579,001 A | 11/1996 | Dempsey et al. |
| 5,579,775 A | 12/1996 | Dempsey et al. |
| 5,600,071 A | 2/1997 | Sooriakumar et al. |
| 5,634,468 A | 6/1997 | Platt et al. |
| 5,682,803 A | 11/1997 | Boianjiu |
| 5,687,734 A | 11/1997 | Dempsey et al. |
| 5,694,940 A | 12/1997 | Unger et al. |
| 5,743,269 A | 4/1998 | Okigami et al. |
| 5,748,103 A | 5/1998 | Flach et al. |
| 5,767,791 A | 6/1998 | Stoop et al. |
| 5,769,755 A | 6/1998 | Henry et al. |
| 5,808,331 A | 9/1998 | Zhang et al. |
| 5,832,490 A | 11/1998 | Riley |
| 5,871,451 A | 2/1999 | Unger et al. |
| 5,882,300 A | 3/1999 | Malinouskas et al. |
| 5,889,211 A | 3/1999 | Maudie et al. |
| 5,899,866 A | 5/1999 | Cyrus et al. |
| 5,910,109 A | 6/1999 | Peters et al. |
| 5,916,159 A | 6/1999 | Kelly et al. |
| 5,917,414 A | 6/1999 | Oppelt et al. |
| 5,919,141 A | 7/1999 | Money et al. |
| 5,938,597 A | 8/1999 | Stratbucker |
| 5,966,692 A | 10/1999 | Langer et al. |
| 5,987,519 A | 11/1999 | Peifer et al. |
| 5,995,861 A | 11/1999 | Price |
| 6,006,125 A | 12/1999 | Kelly et al. |
| 6,013,933 A | 1/2000 | Foerstner et al. |
| 6,018,673 A | 1/2000 | Chin et al. |
| 6,018,705 A | 1/2000 | Gaudet et al. |
| 6,026,321 A | 2/2000 | Miyata et al. |
| 6,057,758 A | 5/2000 | Dempsey et al. |
| 6,066,093 A | 5/2000 | Kelly et al. |
| 6,073,046 A | 6/2000 | Patel et al. |
| 6,076,003 A | 6/2000 | Rogel |
| 6,089,692 A | 7/2000 | Anagnostopoulos |
| 6,150,951 A | 11/2000 | Olejniczak |
| 6,161,036 A | 12/2000 | Matsumura et al. |
| 6,167,290 A * | 12/2000 | Yang et al. .................. 600/322 |
| 6,171,236 B1 | 1/2001 | Bonutti |
| 6,171,237 B1 | 1/2001 | Avitall et al. |
| 6,198,394 B1 | 3/2001 | Jacobsen et al. |
| 6,212,944 B1 | 4/2001 | Kwun et al. |
| 6,298,314 B1 | 10/2001 | Blackadar et al. |
| 6,331,444 B1 | 12/2001 | Ferrari et al. |
| 6,440,067 B1 | 8/2002 | DeLuca et al. |
| 6,448,621 B1 | 9/2002 | Thakur |
| 6,459,934 B1 | 10/2002 | Kadhiresan |
| 6,493,652 B1 | 12/2002 | Ohlenbusch et al. |
| 6,529,771 B1 | 3/2003 | Kieval et al. |
| 6,539,613 B1 | 4/2003 | Ulmer |
| 6,544,171 B2 | 4/2003 | Beetz et al. |
| 6,544,173 B2 | 4/2003 | West et al. |
| 6,544,174 B2 | 4/2003 | West et al. |
| 6,579,231 B1 | 6/2003 | Phipps |
| 6,586,810 B2 | 7/2003 | Thakur |
| 6,623,312 B2 | 9/2003 | Merry et al. |
| 6,794,900 B2 | 9/2004 | Tang et al. |
| 6,847,892 B2 | 1/2005 | Zhou et al. |
| 6,870,484 B1 | 3/2005 | Brinsfield et al. |
| 6,898,550 B1 | 5/2005 | Blackadar et al. |
| 6,904,313 B1 | 6/2005 | Snell |
| 6,911,727 B1 | 6/2005 | Martin et al. |
| 6,997,882 B1 | 2/2006 | Parker et al. |
| 7,187,924 B2 | 3/2007 | Ohlenbusch et al. |
| 7,280,040 B2 | 10/2007 | Devaul |
| 7,318,417 B2 | 1/2008 | Lang et al. |
| 7,382,247 B2 | 6/2008 | Welch et al. |
| 7,439,856 B2 | 10/2008 | Weiner et al. |
| 7,486,980 B2 | 2/2009 | Lin et al. |
| 7,508,064 B2 | 3/2009 | Martin et al. |
| 7,515,043 B2 | 4/2009 | Welch et al. |
| 7,515,044 B2 | 4/2009 | Welch et al. |
| 7,563,632 B2 | 7/2009 | Martin et al. |
| 7,647,196 B2 | 1/2010 | Kahn et al. |
| 7,653,508 B1 | 1/2010 | Kahn et al. |
| 7,753,861 B1 | 7/2010 | Kahn et al. |
| 7,881,902 B1 | 2/2011 | Kahn et al. |
| 7,981,058 B2 | 7/2011 | Akay |
| 7,987,070 B2 | 7/2011 | Kahn et al. |
| 8,180,591 B2 | 5/2012 | Yuen et al. |
| 8,214,007 B2 | 7/2012 | Baker et al. |
| 8,437,824 B2 * | 5/2013 | Moon ................ A61B 5/14551 600/323 |
| 8,630,699 B2 | 1/2014 | Baker et al. |
| 8,750,974 B2 | 6/2014 | Baker et al. |
| 8,965,492 B2 | 2/2015 | Baker et al. |
| 9,155,484 B2 | 10/2015 | Baker et al. |
| 9,237,848 B2 | 1/2016 | Russell |
| 2001/0023315 A1 | 9/2001 | Flach et al. |
| 2002/0055671 A1 * | 5/2002 | Wu et al. .................. 600/310 |
| 2002/0091785 A1 | 7/2002 | Ohlenbusch et al. |
| 2002/0106709 A1 | 8/2002 | Potts et al. |
| 2002/0122519 A1 | 9/2002 | Douglas et al. |
| 2003/0001742 A1 | 1/2003 | Eshelman et al. |
| 2003/0004549 A1 * | 1/2003 | Hill et al. .................. 607/9 |
| 2003/0055460 A1 | 3/2003 | Owen et al. |
| 2003/0149349 A1 | 8/2003 | Jensen |
| 2003/0208113 A1 * | 11/2003 | Mault et al. .................. 600/316 |
| 2003/0208335 A1 | 11/2003 | Unuma et al. |
| 2003/0236452 A1 * | 12/2003 | Melker et al. .................. 600/323 |

(56) References Cited

U.S. PATENT DOCUMENTS

| | | |
|---|---|---|
| 2004/0030258 A1 | 2/2004 | Williams et al. |
| 2004/0034293 A1* | 2/2004 | Kimball ............ A61B 5/14551 600/323 |
| 2004/0113806 A1 | 6/2004 | Neykov |
| 2004/0242976 A1 | 12/2004 | Abreu |
| 2004/0252031 A1 | 12/2004 | Taylor |
| 2005/0116820 A1 | 6/2005 | Goldreich |
| 2005/0137489 A1 | 6/2005 | Jackson et al. |
| 2005/0206518 A1 | 9/2005 | Welch et al. |
| 2005/0216334 A1 | 9/2005 | Mehrabani-Farsi |
| 2005/0234314 A1 | 10/2005 | Suzuki |
| 2005/0245839 A1 | 11/2005 | Stivoric et al. |
| 2006/0044856 A1 | 3/2006 | Bird et al. |
| 2006/0063980 A1 | 3/2006 | Hwang et al. |
| 2006/0074284 A1 | 4/2006 | Juola et al. |
| 2006/0136001 A1 | 6/2006 | Ortega et al. |
| 2006/0183434 A1 | 8/2006 | Westra et al. |
| 2006/0189976 A1 | 8/2006 | Karni et al. |
| 2006/0205171 A1 | 9/2006 | Tsukada |
| 2006/0238333 A1 | 10/2006 | Welch et al. |
| 2007/0013511 A1 | 1/2007 | Weiner et al. |
| 2007/0069887 A1 | 3/2007 | Welch et al. |
| 2007/0073132 A1 | 3/2007 | Vosch |
| 2007/0073178 A1 | 3/2007 | Browning et al. |
| 2007/0073514 A1 | 3/2007 | Nogimori et al. |
| 2007/0191728 A1 | 8/2007 | Shennib |
| 2007/0197920 A1 | 8/2007 | Adams |
| 2007/0270678 A1 | 11/2007 | Fadem et al. |
| 2007/0285226 A1* | 12/2007 | Yi ................................ 600/300 |
| 2007/0288265 A1 | 12/2007 | Quinian et al. |
| 2007/0293781 A1 | 12/2007 | Sims et al. |
| 2008/0079589 A1 | 4/2008 | Blackadar |
| 2008/0139953 A1 | 6/2008 | Baker et al. |
| 2008/0140338 A1 | 6/2008 | No et al. |
| 2008/0275317 A1* | 11/2008 | Cho et al. ..................... 600/310 |
| 2008/0275327 A1 | 11/2008 | Faarbaek et al. |
| 2009/0018409 A1 | 1/2009 | Banet et al. |
| 2009/0043185 A1 | 2/2009 | McAdams et al. |
| 2009/0047645 A1 | 2/2009 | DiBenedetto et al. |
| 2009/0131759 A1 | 5/2009 | Sims et al. |
| 2009/0132197 A1 | 5/2009 | Rubin et al. |
| 2009/0192391 A1 | 7/2009 | Lovitt et al. |
| 2009/0259265 A1 | 10/2009 | Stevenson et al. |
| 2009/0264337 A1* | 10/2009 | Angelides ...................... 435/14 |
| 2009/0319221 A1 | 12/2009 | Kahn et al. |
| 2010/0145202 A1 | 6/2010 | McLaughlin et al. |
| 2010/0160762 A1 | 6/2010 | McLaughlin et al. |
| 2010/0217533 A1 | 8/2010 | Nadkarni et al. |
| 2010/0256947 A1 | 10/2010 | Kim et al. |
| 2010/0298653 A1 | 11/2010 | McCombie et al. |
| 2010/0298661 A1* | 11/2010 | McCombie et al. .......... 600/301 |
| 2010/0324390 A1 | 12/2010 | McLaughlin et al. |
| 2011/0054290 A1* | 3/2011 | Derchak ....................... 600/388 |
| 2011/0054359 A1 | 3/2011 | Sazonov et al. |
| 2011/0066053 A1 | 3/2011 | Yazicioglu |
| 2011/0066064 A1 | 3/2011 | Jangle et al. |
| 2011/0066383 A1 | 3/2011 | Jangle et al. |
| 2011/0191158 A1 | 8/2011 | Kateraas et al. |
| 2011/0288379 A1* | 11/2011 | Wu ................................ 600/301 |
| 2012/0071770 A1 | 3/2012 | Grey et al. |
| 2012/0083714 A1 | 4/2012 | Yuen et al. |
| 2012/0108920 A1 | 5/2012 | Bly et al. |
| 2012/0226117 A1* | 9/2012 | Lamego et al. ............... 600/316 |
| 2012/0245439 A1* | 9/2012 | Andre ................... A61B 5/0205 600/310 |
| 2013/0006125 A1 | 1/2013 | Kroll et al. |
| 2013/0009993 A1 | 1/2013 | Horseman |
| 2013/0060115 A1 | 3/2013 | Gehman et al. |
| 2013/0096843 A1 | 4/2013 | Yuen et al. |
| 2013/0116533 A1 | 5/2013 | Lian et al. |
| 2013/0158686 A1 | 6/2013 | Zhang et al. |
| 2013/0190903 A1 | 7/2013 | Balakrishnan et al. |
| 2013/0261422 A1 | 10/2013 | Gilmore et al. |
| 2014/0100432 A1 | 4/2014 | Golda et al. |
| 2014/0156043 A1 | 6/2014 | Blackadar et al. |
| 2014/0206976 A1 | 7/2014 | Thompson et al. |
| 2014/0275932 A1 | 9/2014 | Zadig |
| 2015/0073231 A1 | 3/2015 | Beck et al. |
| 2015/0119728 A1 | 4/2015 | Blackadar et al. |
| 2015/0148637 A1 | 5/2015 | Golda et al. |
| 2015/0265173 A1 | 9/2015 | Datovech et al. |
| 2016/0029917 A1 | 2/2016 | Baker et al. |
| 2016/0029918 A1 | 2/2016 | Baker et al. |
| 2016/0128598 A1 | 5/2016 | Takizawa et al. |
| 2016/0242654 A1 | 8/2016 | Quinlan et al. |
| 2017/0000371 A1 | 1/2017 | Quinlan et al. |
| 2017/0000372 A1 | 1/2017 | Quinlan et al. |

FOREIGN PATENT DOCUMENTS

| | | |
|---|---|---|
| EP | 0 665 584 B1 | 4/1999 |
| EP | 0 910 985 A1 | 4/1999 |
| JP | 11-088546 A2 | 3/1990 |
| JP | 11-042214 A2 | 2/1999 |
| WO | WO 96/20641 A1 | 7/1996 |
| WO | WO 96/29005 A1 | 9/1996 |
| WO | WO 97/46156 A1 | 12/1997 |
| WO | WO 99/59460 A2 | 11/1999 |
| WO | WO 01/89362 A2 | 11/2001 |
| WO | WO 01/97686 A1 | 12/2001 |
| WO | WO 01/89362 A3 | 2/2004 |
| WO | WO 2008/057884 A2 | 5/2008 |
| WO | WO 2008/142365 A1 | 11/2008 |
| WO | WO 2009/056859 A1 | 5/2009 |
| WO | WO 2009/083032 A1 | 7/2009 |
| WO | WO 2012/127370 A1 | 9/2012 |
| WO | WO 2012/140322 A1 | 10/2012 |

OTHER PUBLICATIONS

Fimbel et al., "Event identification in movement recordings by means of qualitative patterns," Neuroinformatics, Sep. 2003;1(3):239-57.

Boyd, Jeffrey and Sundaram, Hari, "A Framework to Detect and Classify Activity Transitions in Low-Power Applications," ICME'09: Proceedings of the 2009 IEEE International Conference on Multimedia and Expo, Jun. 2009.

Kawahara, Y., Ryu, N., and Asami, T., "Monitoring Daily Energy Expenditure Using a 3-Axis Accelerometer with a Low-Power Microprocessor," Int J Hum-Comput Interact 1(5): 145-154 (Mar. 2009).

Lee, M.-H., Kim, J., Kim, K., Lee, I., Jee, S.H., and Yoo, S.K.: "Physical Activity Recognition Using a Single Tri-Axis Accelerometer." In: Proceedings of the World Congress on Engineering and Computer Science (WCECS 2009), San Francisco, USA, vol. 1, pp. 14-17 (Oct. 2009).

Khan, A.M., Lee, Y.K., and Lee, S.Y., "Accelerometer's Position Free Human Activity Recognition Using a Hierarchical Recognition Model," e-Health Networking Applications and Services (Healthcom), 2010 12th IEEE International Conference, pp. 296-301, Jul. 1-3, 2010.

Bassett et al., Accelerometer-Based Physical Activity: Total Volume per Day and Standardized Measures. Med Sci Sports Exerc. Aug. 6, 2014. [Epub ahead of print].

Weyand et al., Ambulatory estimates of maximal aerobic power from foot-ground contact times and heart rates in running humans. J Appl Physiol (1985). Jul. 2001;91(1):451-8.

[No Author Listed] U.S. Department of Health and Human Services (2006). General Physical Activities Defined by Level of Intensity. Physical activity for everyone: measuring physical activity intensity: metabolic equivalent (MET) level. Retrieved from http://www.cdc.gov/nccdphp/dnpa/physical/pdf/PA_Intensity_table_2_1.pdf; pp. 1-5.

Casale et al., Personalization and user verification in wearable systems using biometric walking patterns. Pers Ubiquit Comput. Jul. 2011:18pgs.

International Search Report and Written Opinion for PCT/US2014/056532 mailed Dec. 29, 2014.

(56) References Cited

OTHER PUBLICATIONS

Extended European Search Report for European Application No. 14769534.0 dated Oct. 18, 2016.
International Preliminary Report on Patentability for PCT/US2014/022624 mailed Sep. 24, 2015.
International Preliminary Report on Patentability for PCT/US2014/056532 mailed Sep. 1, 2016.
International Search Report and Written Opinion for International Application No. PCT/EP2016/069546 dated Oct. 31, 2016.
Friel, Efficiency Factor and Decoupling. TrainingPeaks. http://home.trainingpeaks.com/blog/article/efficiency-factor-and-decoupling Dec. 7, 2011[1ast accessed Oct. 25, 2016].
Hanalainen et al., Jerk-based feature extraction for robust activity recognition from acceleration data. 11th Intl. Conf. on Intelligent Sys. Design and App. 2011:831-6.
Helmi et al., Human activity recognition using a fuzzy inference system. Fuzzy Systensm 2009. Fuzz-IEEE 2009. IEEE International Conference.
Mohammad et al., Human activity recognition using a fuzzy inference system. Fuzzy Systems, 2009. Fuzz-IEEE 2009. IEEE International conference on IEEE, 2009.

* cited by examiner

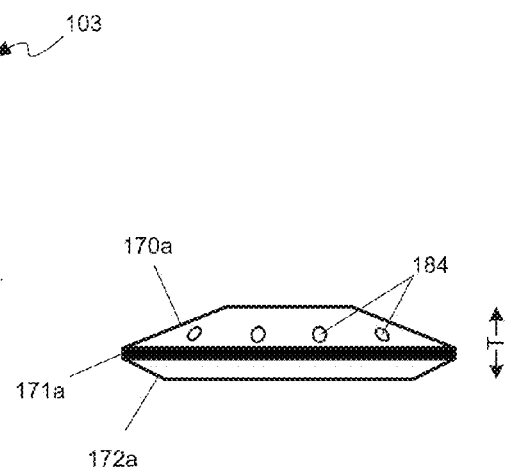
FIG. 1D
FIG. 1E
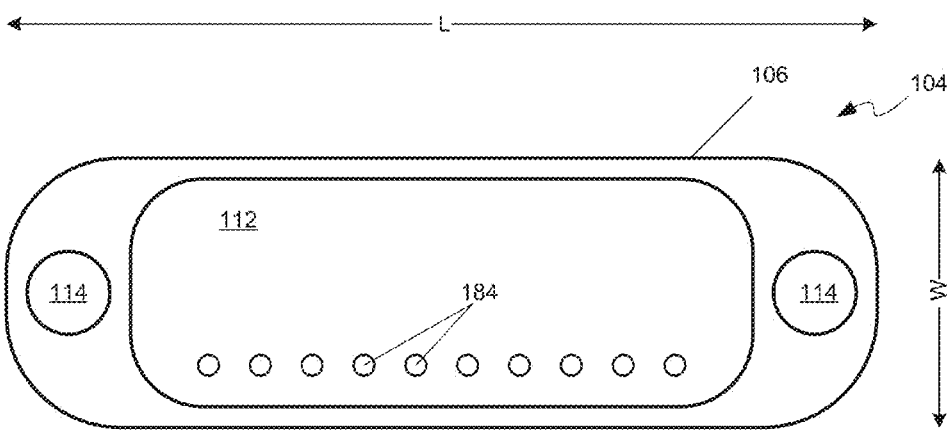
FIG. 1F

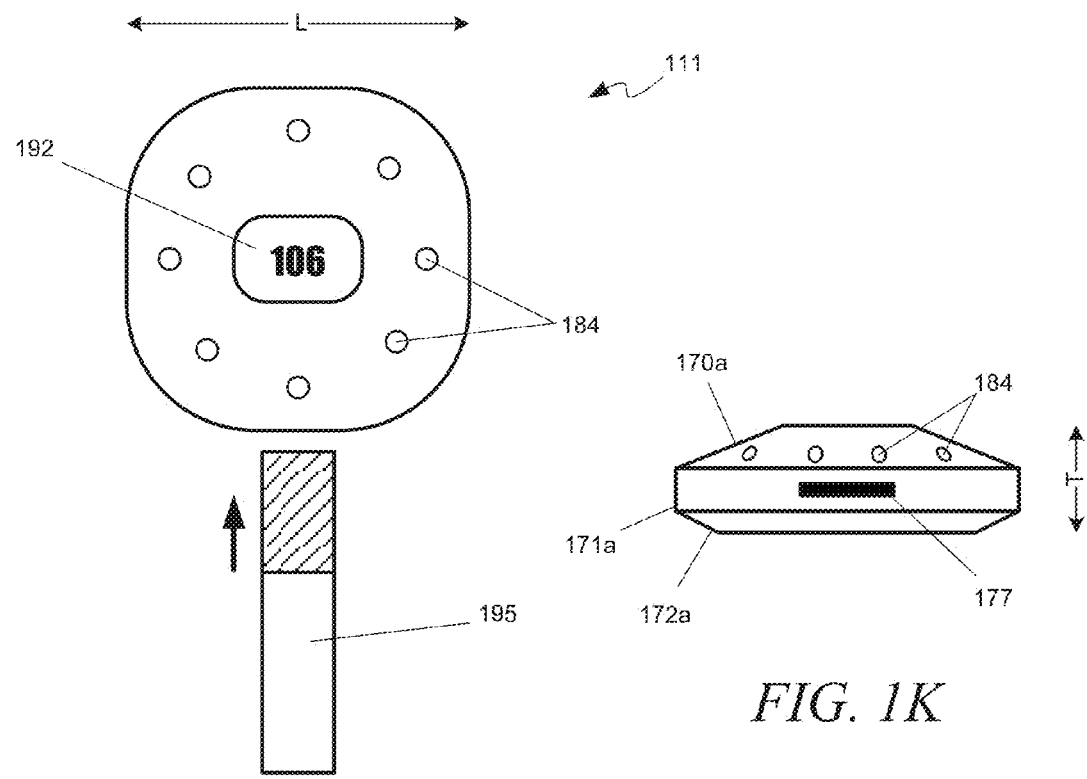
FIG. 1J
FIG. 1K
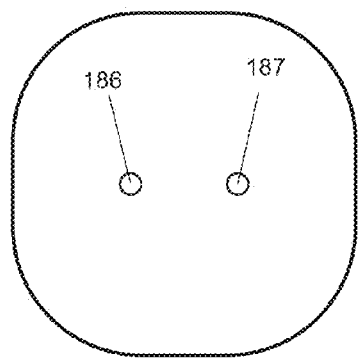
FIG. 1L

VERSATILE SENSORS WITH DATA FUSION FUNCTIONALITY

RELATED APPLICATIONS

This application is a continuation-in-part of U.S. application Ser. No. 13/690,313, titled "Intelligent Activity Monitoring," filed on Nov. 30, 2012, and now pending, which claims the benefit of U.S. provisional application Ser. No. 61/566,528, titled "Intelligent Activity Monitoring," filed on Dec. 2, 2011. The entire disclosures of both of the foregoing applications are incorporated herein by reference.

FIELD

This disclosure relates generally to apparatuses and methods for dynamically detecting and identifying one or more of various types of sensors configured to sense one or more parameters of an entity, organizing the sensors into a network controlled by a central hub, and selectively analyzing data from one or more of the sensors. In some embodiments, motion and physiological data are obtained from one or more fitness/health sensors and processed to provide a fitness/health metric or diagnosis for a subject.

BACKGROUND

There currently exist small sensors that can be worn by a user to monitor an activity or two similar types of user activity. As an example, the FitLinxx® ActiPed+ (available from FitLinxx, Shelton, Conn., USA) is a small device that can be clipped to a shoe and used to monitor walking and running activities by the user. When a user walks or runs, an on-board accelerometer outputs data that is stored on the device for subsequent transmission to a computer system. The computer system can analyze the data to determine activity type, and calculate various activity parameters (e.g., duration of activity, total steps, distance traveled, and calories burned). Results of the data analysis may be presented on the computer's display, so that a user may review details of his or her activity. The results may be stored, so that the user can maintain a record of exercise regimens and track progress toward exercise goals or track recovery from an illness or injury.

SUMMARY OF EXAMPLE EMBODIMENTS

Some embodiments described herein relate to various types of sensors, including at least one versatile sensor, that are configured to be used alone or in combination in a flexible network to monitor at least one fitness or health parameter of a subject. An intelligent activity monitor may identify a particular type of activity from among a plurality of different activities. A versatile sensor may, for example, participate in an ad hoc network that includes an intelligent activity monitor, receive supplemental physiological data, and compute fitness/health metrics or diagnoses pertinent to the subject. In some implementations, various types of sensors may be combined into a fitness sensing system. Examples of fitness/health metrics that may be computed in some embodiments include cardiovascular efficiency, activity-moderated blood glucose level, activity-moderated cardiac functioning, activity-moderated respiration, etc. The fitness/health metrics may be used as diagnostics in athletic (e.g., fitness training, athlete performance) and medical (e.g., patient evaluation, patient recovery) settings.

Some embodiments relate to the use of various types of sensors, including at least one versatile sensor, that are configured to be used alone or in combination in a flexible network to monitor at least one parameter for industrial or machinery applications. For example, intelligent sensors may be used in combination to monitor several parameters of a facility or machine. A versatile sensor may organize the intelligent sensors into an ad hoc network, analyze data from the sensors, and provide diagnostic data relevant to the performance of the facility or machine.

The terms "fitness" and "health" may be used interchangeably throughout this disclosure when referring to fitness or health of a subject. It will be understood that "fitness" may be a more relevant term when referring to healthy subjects partaking in exercise for the purpose of health maintenance or athletic improvement. "Health" may be a more relevant term when referring to ailing subjects partaking in exercise for the purpose of improving health, e.g., recovering from an ailment.

The terms "sensor" or "monitor" may be used when referring to a small electronic device configured to sense at least one parameter of an entity. A sensor may have limited processing power. A sensor may be configured to transmit data wirelessly or via a wired link to a second device. "Sensor" or "monitor" may also be used as shorthand when referring to an intelligent sensor and versatile sensor, the intended meaning being clear from the context.

The terms "intelligent sensor" or "intelligent monitor" may be used when referring to a small electronic device configured to sense at least one parameter of an entity, and to process received data. An intelligent sensor has greater processing power than a sensor, and may include at least one microcontroller or microprocessor. An intelligent sensor may be configured to transmit data wirelessly or via a wired link to a second device.

The terms "versatile sensor" or "versatile monitor" may be used when referring to a small electronic device configured to sense at least one parameter of an entity, to process received data, and to flexibly participate in a small-area network. A versatile sensor may be configured to transmit data wirelessly or via a wired link to a plurality of devices.

The terms "fitness sensing system," "health sensing system," or "sensing system" may be used to refer to a network of sensors that may include at least one versatile sensor or at least one intelligent activity monitor.

The term "processor" may be used to refer to more than one processor. For example, a fitness sensing system may have more than one processor configured to operate in a network to provide various functionalities for the fitness sensing system. The multiple processors may be referred to as a processor of the system.

Configurations and operation of local area networks (LANs) that include one or more versatile sensors are described. Fitness sensing systems may, for example, include at least one low-power, versatile sensor that may flexibly function as a slave device to a central hub in one network, and in some embodiments may also temporarily operate effectively as a master to one or more sensors within the network. In some implementations, a versatile sensor may configure itself to act as a central hub in a LAN. In some instances, for example, a versatile sensor may be adapted to receive data from a proximal sensor belonging to another local area network. In some embodiments, a versatile sensor may change its configuration within a network based upon data "overheard" from one or more intranetwork and/or internetwork sensors. When the overheard data comprises actionable data, a versatile sensor may, for example, receive and process data from one or more sensors and alter its mode of operation. In some embodiments, data processed from another sensor may be used, for example, to enrich the informational content of data produced by the versatile sensor, and computed results obtained from the combined data may be sent to a central hub of a sensing system, or other destination, for further processing and/or recording.

In some cases, a versatile sensor may alter the mode of operation of another sensor from which it receives data.

According to some embodiments, a fitness sensing system may comprise at least one versatile sensor and at least one sensor or intelligent sensor, wherein each sensor in the sensing system may sense at least one parameter of a subject. The versatile sensor may, for example, be configured to receive data from the at least one sensor or intelligent sensor, and process the data in combination with additional data representative of the subject to compute a fitness metric or diagnosis of the subject. In some embodiments, a versatile sensor may organize all sensors in the system into a LAN, and may control one or more sensors in the network. A versatile sensor may, for example, issue commands to other sensors in the LAN and set communication protocols so as to establish and improve low-power operation.

In some embodiments, a fitness sensing system may be configured to be supported by a subject, e.g., attached to at least a subject's wrist, ankle, arm, torso, or leg. The fitness sensing system may comprise a processor, at least one display, a non-invasive blood glucose monitor, and an intelligent activity monitor. The intelligent activity monitor may include at least one accelerometer. The processor may be configured to process data received from the accelerometer so as to identify, from among a plurality of different activities, an activity performed by the subject. The activity may be any one of the plurality of different activities. The processor may be further configured to compute at least one metric representative of the identified activity, e.g., a duration of the activity, a pace of the activity, calories burned during the activity. The processor may be further configured to process data from the blood glucose monitor in combination with the data received from the accelerometer and to determine an operational mode, from among a plurality of operational modes, for the blood glucose monitor. For example, the processor may be configured to place the blood glucose monitor in a selected mode of the plurality of operational modes based upon the processed data from the blood glucose monitor and the data received from the accelerometer.

In some implementations, a fitness sensing system may be configured to be supported by a subject. The fitness sensing system may comprise a processor, at least one display, a blood glucose monitor that is configured to read disposable test strips, and an intelligent activity monitor. The intelligent activity monitor may include at least one accelerometer. The processor may be configured to process data received from the accelerometer so as to identify, from among a plurality of different activities, an activity performed by the subject. The activity may be any one of the plurality of different activities. The processor may be further configured to compute at least one metric representative of the identified activity. The processor may be further configured to process data from the blood glucose monitor in combination with the data received from the accelerometer and to determine an operational mode for the blood glucose monitor based upon the results of processing data from the blood glucose monitor in combination with the data received from the accelerometer. For example, the processor may be configured to place the blood glucose monitor in an active state for making a blood glucose reading, and/or in a reduced-power or no-power state for a selected period of time. The processor may determine the selected period of time based upon the processed data from the blood glucose monitor and the data received from the accelerometer.

Various methods for operating fitness sensing systems configured to be supported by a subject are also described. An example method for operating a fitness sensing system may comprise acts of processing, by a processor adapted to control the fitness sensing system, first data received from an accelerometer of the fitness sensing system to identify, from among a plurality of different activities, an activity performed by the subject. The method may further include computing, by the processor, at least one metric representative of the identified activity, and processing, by the processor, second data received from a non-invasive blood glucose monitor of the fitness sensing system. Processing of the second data may provide at least a blood glucose level reading for a subject. According to some embodiments, the method may further comprise determining, by the processor, an operational mode, from among a plurality of operational modes, for the blood glucose monitor based upon the results of the at least one metric and the processing of the second data.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIGS. 1D-1E depict an intelligent activity monitor that includes an LED display for communicating information to a user, according to some embodiments;

FIGS. 1F-1H illustrates a fitness/health sensing system, according to some embodiments;

FIGS. 1J-1L illustrate a fitness/health sensing system that includes activity and blood glucose monitoring functionality, according to some embodiments;

Figure 1A:
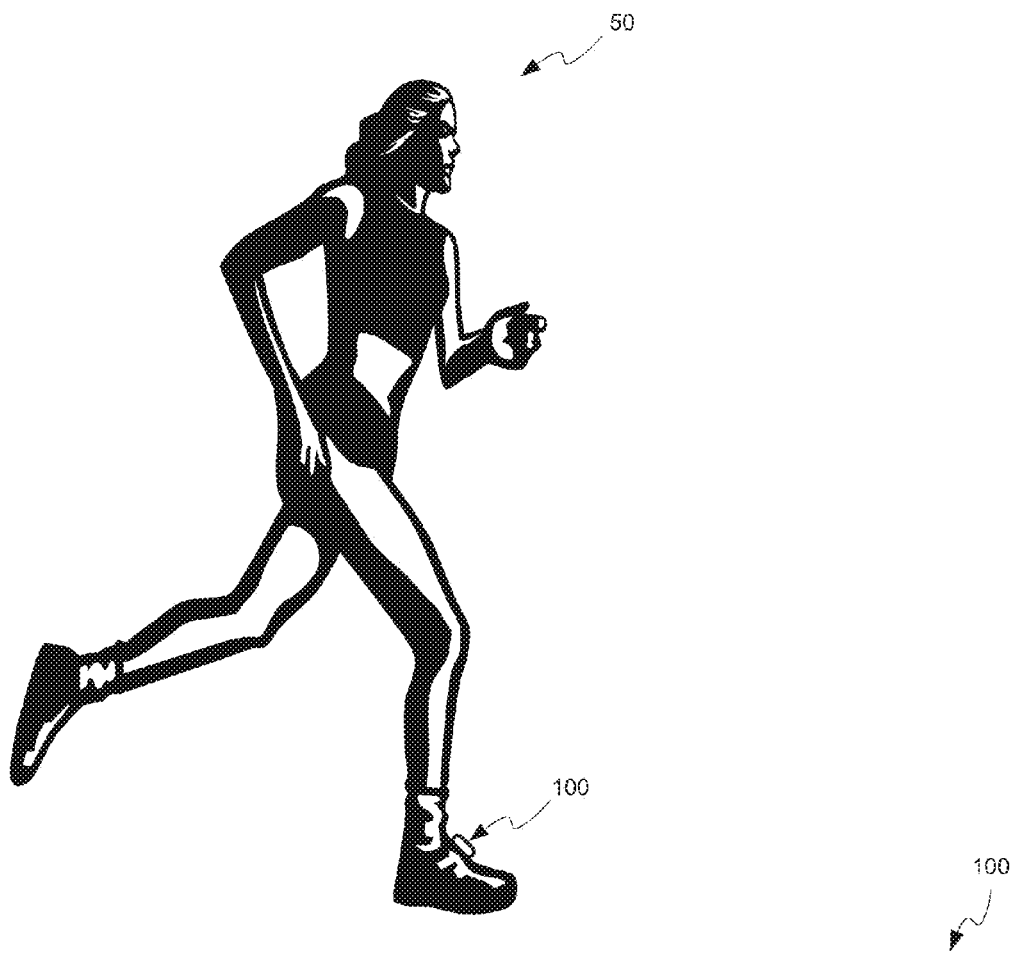
FIG. 1A depicts an illustrative example of an intelligent activity monitor 100 supported by a subject 50. In some embodiments, the activity monitor may be supported at locations on the subject other than the foot or ankle.

The features and advantages of the present invention will become more apparent from the detailed description set forth below when taken in conjunction with the drawings.

DETAILED DESCRIPTION OF EXAMPLE EMBODIMENTS

I. Overview

We have recognized there currently exists no commercial product for detecting, identifying, and analyzing, in a small single unit, different types of human activities (e.g., running, swimming, biking, etc.), as well as for detecting and identifying non-human activities. We have appreciated, moreover, that there has been significant research and development in the areas of pattern matching, neural networks, and gesture recognition in recent years. Such technology may be used for image recognition, speech recognition, etc., and may find applications in activity recognition by a machine. We have recognized, however, that in a vast majority of these "machine recognition" cases, the algorithms can be computationally expensive and may require advanced signal processing methods which would be difficult to implement on a small processor that could be incorporated in a small package worn by a user, such as a package sized and configured to be worn on a user's wrist. One approach to reducing computational burden is to use integer math at the expense of accuracy for pattern matching calculations. However, the energy consumption requirements by a processor configured to carry out such recognition algorithms using integer math still may be prohibitively large and require a user to either frequently recharge the device or replace its batteries.

In part, this disclosure relates to a small, low-power, electronic intelligent activity monitor that may be attached to a user, and that may, for example, be configured to detect and identify a specific activity type from among a plurality of different activity types. Also disclosed are data-processing architectures and algorithms that may be used, for example, to process data generated by such an intelligent activity monitor, as well as low-power operation paradigms for an intelligent activity monitor. In certain embodiments, an on-board microcontroller may, for example, receive and process data from a tri-axis accelerometer by employing a data-reduction algorithm that combines outputs from multiple axes of the accelerometer to identify a specific type of activity, including both human and non-human activities, from among a plurality of activities. In some implementations, the data-reduction algorithm that is employed may, for example, reduce the computational load on the processor and reduce overall power consumption of an intelligent activity monitor when identifying activity types and/or analyzing data from an identified activity.

We have recognized that a small, intelligent activity monitor that is configured, for example, to distinguish between a plurality of different user activities may be useful for a wide variety of applications including, but not limited to, fitness monitoring and evaluation, health and medical applications (e.g., patient monitoring or tracking rehabilitation progress), validating fitness-based health-insurance discounts, monitoring animal activity, monitoring human special service activities (e.g., monitoring activities of fire, rescue, or police personnel). We have also recognized that for some applications, for such a device to be widely adopted, it is preferable that the device not be overly cumbersome or hindering when attached to a user, that it have a long battery life, and that it be able to distinguish between a plurality of human as well as non-human activities. Further, we have determined that it may be advantageous for some applications for the data reported by the activity monitor to be accompanied by a measure of quality or confidence of the data, so that partial credit may be given for an activity rather than an all-or-nothing approach.

We have also recognized that in at least some circumstances useful results may be obtained from an intelligent activity monitor when it is worn or supported at any of various locations on a person (e.g., on the leg, below the knee, on the shoe, on the belt, in pants pockets, in shirt pockets, and clipped to chest straps or women's undergarments, etc.) and that the data signals produced by such a sensor may vary considerably depending upon the location of the device on the person. Locations at which an intelligent activity monitor may be worn may affect the measured signals, for example, both in shape and amplitude. We have realized that signals received from an accelerometer in an intelligent activity monitor may be processed, for example, to determine where on the body the device is being worn in addition to determining the type of activity. By knowing where the device is located on the person's body, the quality or usefulness of the measured data may, for example, be improved algorithmically.

The constraints of a small yet sophisticated device with a long battery life may pose difficult technical challenges for an intelligent activity monitor. For example, sophisticated hardware and computational power to distinguish between similar and different types of activities via machine recognition, small size (e.g., size of a wristwatch or smaller), and low power consumption may be considerations for certain applications. In order to meet these challenges, an illustrative embodiment of an intelligent activity monitor described herein employs a combination of low-power techniques, a small on-board and variable clock-rate processor, and specially developed data-processing algorithms, and is thus suitable for a wide variety of applications as described above.

Various embodiments of apparatuses, methods, and systems for an intelligent activity monitor are described in further detail in the following sections of the specification. In overview and with reference to FIG. 1A, an intelligent activity monitor 100 may, as shown, comprise a small electronic device that can be attached to or supported by a subject 50, and that may be configured to identify a type of activity from among a plurality of different activities that may be performed by the subject, and to process data received during an identified activity to calculate one or more parameters representative of the activity. In various embodiments, the subject 50 may be human or non-human, animate or inanimate. In certain embodiments, an intelligent activity monitor 100 may be supported by a subject 50 in any suitable manner (e.g., strapped to an ankle or wrist like a watch, or attached to an article of clothing worn by the subject, clipped to a spoke on a wheel) at any suitable location on a subject. There may, in some embodiments, be a wide variety of different activities that can be identified by the activity monitor (e.g., walking, running, biking, swimming, using an elliptical workout machine, rowing, cross-country skiing, performing jumping jacks, performing athletic drills, and/or jumping rope). In some embodiments, an intelligent activity monitor 100 may additionally or alternatively be configured to identify "fake" or falsified activities, e.g., activities alleged to be human activities that are not common to or not capable of being performed by a human subject 50.

In some embodiments, an intelligent activity monitor may, for example, comprise an accelerometer capable of generating one or more data streams representative of motion of the activity monitor and a programmable microprocessor along with machine-readable instructions adapted to analyze the one or more data streams to identify the type of activity performed by the subject 50 as well as identify a fake activity, and to process data received during an identified activity. In certain embodiments, an intelligent activity monitor 100 may further be configured to communicate (e.g., exchange data wirelessly or via a wired communication port) with a remote device such as a computer, smart phone, or other data-processing device in a network. In some embodiments, an intelligent activity monitor may additionally be adapted for low-power operation such that it can operate for days in some embodiments, months in some embodiments, or even years in some embodiments, between times of recharging or replacement of its power source.

There are a wide variety of applications for which various embodiments of an intelligent activity monitor may be useful. Examples of such applications include, but are not limited to, a monitor for general health and fitness purposes, monitoring rehabilitation activities of a human or animal subject, an aide to monitor training regimens for competitive and/or elite athletes, an aide to monitor training regimens for animals trained for competition, a monitor for exercise validation in incentive-based health-insurance discount programs, a motion monitor for inanimate moving objects, gait analysis, and workplace occupational conformance.

II. Example Apparatus

Figure 1B:
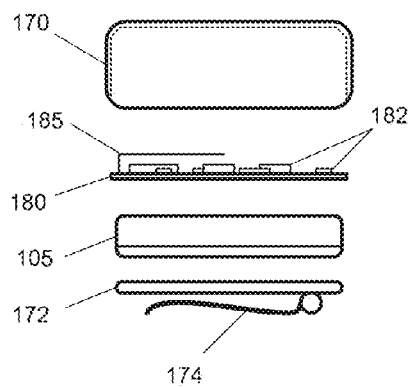
FIG. 1B depicts examples of components that may be included in an activity monitor such as that shown in FIG. 1A.

Referring now to FIG. 1B, an exploded view of an illustrative example of an intelligent activity monitor 100 that may be employed in certain embodiments is illustrated. As shown, an intelligent activity monitor 100 may, for example, comprise an enclosure that includes a first cover 170 and second cover 172. The first and second covers may be formed from any suitable materials including, but not limited to, metals and plastics or combinations thereof. As one example, the first cover 170 may be a molded plastic and the second cover 172 a corrosion-resistant metal. The first and second covers may be fastened together by any suitable means to form a water-tight seal and to enclose a power source 105 and electronic circuitry 180 of the activity monitor. A clip or strap 174 may be disposed on or attached to a surface of one of the covers so that the activity monitor 100 may be attached to or supported by a subject or machine (e.g., strapped to a wrist, ankle, or appendage, clipped to an article of clothing, strapped or clipped to a movable portion of a machine.)

As shown, the electronic circuitry 180 may, for example, comprise a combination of circuit elements 182 disposed on a printed circuit board. In various embodiments, the circuit elements 182 may, for example, include a selected combination of integrated circuit (IC) chips, application-specific integrated circuit (ASIC) chips, at least one microcontroller or microprocessor, micro-electrical-mechanical system (MEMS) devices, resistors, capacitors, inductors, diodes, light-emitting diodes, transistors, and/or conductive circuit traces, etc. A microcontroller or microprocessor may, for example, coordinate and manage operation of the intelligent monitor's electronic circuitry. In some embodiments, the electronic circuitry 180 may further include at least one radio-frequency (RF) antenna 185 for use in sending and receiving RF communication signals.

Figure 1C:
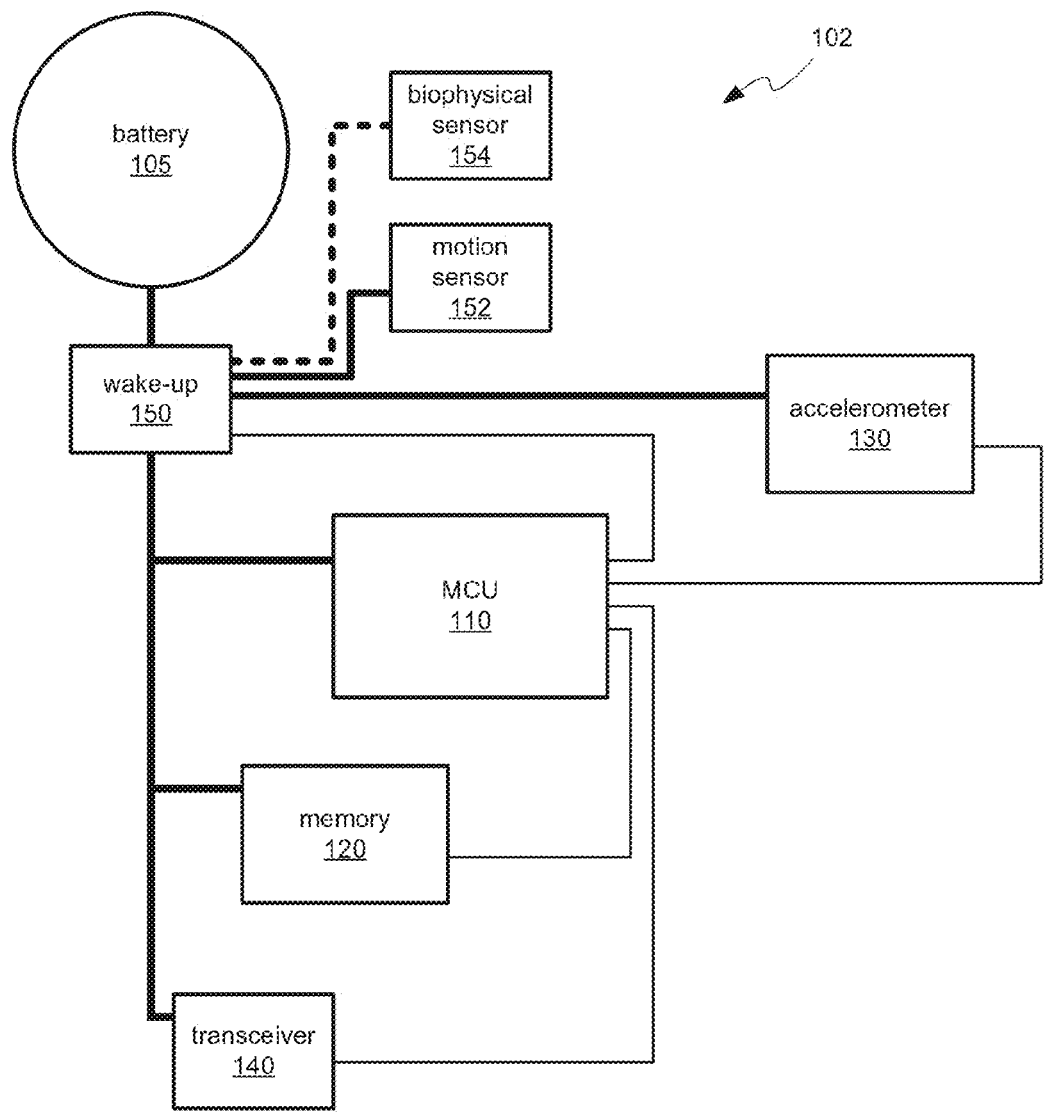
FIG. 1C is a block diagram illustrating examples of selected electrical components that may be included in an activity monitor such as that shown in FIGS. 1A-B.

FIG. 1C depicts an example embodiment of internal circuitry 102 that may be used in an intelligent activity monitor 100 in further detail. As shown, the monitor's circuitry may, for example, comprise a source of power 105, e.g., a battery or energy-scavenging chip and a wake-up and power-management circuit 150, that provide and manage power to an accelerometer 130, a microprocessor or microcontroller 110, memory 120, and a transceiver 140. The microcontroller 110 may be coupled to the wake-up circuit, the accelerometer, memory, and the transceiver. The microcontroller may be configured to receive and process acceleration data from the accelerometer 130, to read and write data to memory 120, and to send and receive data from transceiver 140. The wake-up circuit 150 may be adapted to sense when the activity monitor 100 is not in use, and in response, reduce power consumption of the internal circuitry 102. The wake-up circuit may be further adapted to sense when the activity monitor 100 is placed in use, and in response, activate one or more elements of the internal circuitry 102.

In some embodiments, the microprocessor or microcontroller 110 may, for example, comprise a low-power, 8-bit microcontroller configured to draw low power in sleep-mode operation, and capable of operating at multiple millions of instructions per second (MIPS) when activated. One example of a suitable microcontroller is the 8051F931 microcontroller available from Silicon Laboratories Inc. of Austin, Tex., though any other suitable microcontroller or microprocessor may alternatively be employed in other embodiments. The microcontroller 110 may, for example, include various types of on-board memory (e.g., flash memory, SRAM, and XRAM) for storing data and/or machine-readable instructions, and may be clocked by an internal oscillator or external oscillator. In some embodiments, the microcontroller may, for example, be clocked by an internal high-frequency oscillator (e.g., an oscillator operating at about 25 MHz or higher) when the microcontroller is active and processing data, and alternatively clocked by a low-frequency external oscillator when the microcontroller is substantially inactive and in sleep mode. The clocking of the microcontroller at low frequency may, for example, reduce power consumption by the microcontroller during sleep mode. The low-frequency clocking may be at a frequency that is less than 50% of the high-frequency clocking in some embodiments, less than 20% of the high-frequency clocking in some embodiments, less than 10% of the high-frequency clocking in some embodiments, less than 5% of the high-frequency clocking in some embodiments, less than 2% of the high-frequency clocking in some embodiments, less than 1% of the high-frequency clocking in some embodiments, and yet less than 0.1% in some embodiments.

In various embodiments, the microcontroller 110 may be configured to receive acceleration data from accelerometer 130 and process the received data according to pre-programmed machine-readable instructions that are loaded onto and execute on the microcontroller. The microcontroller 110 may, for example, be configured to receive analog and/or digital input data, and may include on-board analog-to-digital and digital-to-analog converters and on-board timers or clocks. In some embodiments, the microcontroller may be further configured to receive power through wake-up and power management circuitry 150. The microcontroller may, for example, cooperatively operate with or comprise a portion of power management circuitry 150, and assist in the activating and deactivating of one or more circuit elements within the activity monitor.

In some embodiments, the microcontroller 110 may be configured to be operable at a number of different clock frequencies. When operating at a low clock frequency, the microcontroller will typically consume less power than when operating at a high clock frequency. In some embodiments, the microcontroller may, for example, be configured to be in a "sleep" mode and operating at a low clock frequency when there is no motion of intelligent activity monitor 100, and to be cycled through several operating states when motion of the activity monitor 100 is detected. An example of how a microcontroller may be cycled in such manner will be described below in reference to FIG. 2. As one example, when in sleep mode, the microcontroller may sample data at a rate less than 10 Hz and draw less than about 30 microamps.

In some embodiments, accelerometer 130 may, for example, comprise a multi-axis accelerometer configured to sense acceleration along at least two substantially orthogonal spatial directions. The accelerometer 130 may, for example, comprise a three-axis accelerometer based on micro-electro-mechanical systems (MEMS) technology. In some implementations, one or more single-axis accelerometers may additionally or alternatively be used. In some embodiments, the accelerometer 130 may be configured to provide one or more analog data-stream outputs (e.g., X, Y, Z data outputs corresponding to each axis of the accelerometer) that are each representative of a magnitude and direction of acceleration along a respective axis. One example of a suitable accelerometer is the Kionix model KXSC7 accelerometer available from Kionix Inc., Ithica, N.Y. The accelerometer 130 may, for example, provide analog output data, that may later be converted to digital data, or may provide digital output data representative of acceleration values.

The accelerometer 130 may be characterized by several parameters. Among these parameters may, for example, be a sensitivity value and a sampling rate value. As examples, the accelerometer's analog sensitivity may be between about 100 millivolts (mV) per gravitational value (100 mV/G) and about 200 mV/G in some embodiments, between about 200 mV/G and about 400 mV/G in some embodiments, between about 400 mV/G and about 800 mV/G in some embodiments, and yet between about 800 mV/G and about 1600 mV/G in some embodiments. When configured to provide a digital output, the sampling rate of the accelerometer may, for example, be between about 10 samples per second per axis (10 S/sec-A) and about 20 S/sec-A in some embodiments, between about 20 S/sec-A and about 40 S/sec-A in some embodiments, between about 40 S/sec-A and about 80 S/sec-A in some embodiments, between about 80 S/sec-A and about 160 S/sec-A in some embodiments, between about 160 S/sec-A and about 320 S/sec-A in some embodiments, and yet between about 320 S/sec-A and about 640 S/sec-A in some embodiments. It will be appreciated that in some embodiments the higher sampling rates may improve the quality of the measured accelerations.

It will be appreciated that, in some embodiments, an accelerometer 130 may be combined with one or more analog-to-digital converters to provide digital output data representative of acceleration values at sampling rates described above. When digital output data is provided by an accelerometer, the accelerometer's sensitivity may be expressed in units of bits per gravitational constant (b/G). As examples, an accelerometer providing digital output data may have a sensitivity of more than about 2 b/G in some embodiments, more than about 4 b/G in some embodiments, more than about 6 b/G in some embodiments, more than about 8 b/G in some embodiments, more than about 10 b/G in some embodiments, more than about 12 b/G in some embodiments, or even higher values in some embodiments.

According to some embodiments, an intelligent activity monitor 100 may include one or more sensors in addition to motion sensor 152 and accelerometer 130. For example, an intelligent activity monitor may include a physiological sensor 154 configured to sense at least one physiological parameter of a subject. Examples of physiological parameters that may be sensed in some embodiments include, but are not limited to, heart rate, skin temperature, core temperature, respiration rate, pleth waveform, EKG waveform, blood oxygenation level, blood glucose level, hydration, blood pressure, etc. Physiological sensor 154 may be disposed in a same package with an intelligent activity monitor in some implementations, or may be formed as a separate monitor to be attached to the subject at a separate location and wirelessly transmit data to the intelligent activity monitor according to a predetermined communication protocol. When receiving data from additional sensors, an intelligent activity monitor may be functioning as a versatile sensor.

In some embodiments, an intelligent activity monitor 100 may include memory 120 that is external to and accessible to the microcontroller 110. The memory 120 may be any one of or combination of the following types of memory: RAM, SRAM, DRAM, ROM, flash memory. The memory 120 may, for example, be used to store and/or buffer raw data from accelerometer 130, machine-readable instructions for microcontroller 110, program data used by the microcontroller for processing accelerometer data, and/or activity data resulting from the processing of accelerometer data. In some embodiments, the memory 120 may additionally or alternatively be used to store diagnostic information about the health of the activity monitor, e.g., battery life, error status, etc., and/or physical parameters about the device, e.g., memory size, gravitational sensitivity, weight, battery model, processor speed, version of operating software, user interface requirements, etc. In some embodiments, the memory may also be used to store information pertinent to a user, e.g., user weight, height, gender, age, training goals, specific workout plans, activity-specific data for a user that may be used to identify an activity performed by the user or process data representative of an identified activity.

In some embodiments, the memory 120 may additionally or alternatively be used to store data structures and/or code received from an external device, e.g., via a wired or wireless link. The data structures and/or code may, for example, be used to update one or more data processing applications used by the activity monitor. For example, one type of data structure may be data representative of an acceleration data pattern that may be used to identify a specific type of activity not previously recognized by the activity monitor, e.g., a new activity or an activity that is specific to an individual user of the activity monitor. As another example, a data structure may comprise a membership function, described below, defined for a new activity or redefined for an identifiable activity. The data structure may, for example, include one or more sample accelerometer traces obtained from the activity and/or may comprise identification data (e.g., membership functions) resulting from the processing of the accelerometer traces that may be used in an algorithm executed by the activity monitor 100 to identify the activity. Further, in some embodiments, the memory 120 may be used to store updates and/or replacements to algorithms executed by the activity monitor. The stored data structures and algorithms may, for example, be used to reprogram and/or expand the functionality of the activity monitor 100 to identify new activities or activities not previously recognized by the activity monitor and/or improve the accuracy or confidence of results calculated for identified activities.

In some embodiments, the memory 120 may also be used to store calibration and/or conversion data that is used by the microcontroller 110 to characterize detected activities. Calibration data may, for example, be used to improve the accuracy of detected activity parameters, e.g., stride length, speed. Conversion data may, for example, be used to convert a detected activity into an amount of expended human energy, e.g., calories burned, metabolic equivalents, etc.

In some embodiments, an intelligent activity monitor 100 may include a transceiver 140 and/or one or more data communication ports (e.g., a USB port, an RF communication port, a Bluetooth port) for communicating data between the activity monitor and one or more external devices such as a computer, tablet, cell phone, portable communication device, data processor, a sensor, another intelligent sensor, or a versatile sensor, any of which may be configured to communicate with other similar devices in a network such as the world-wide web or a local area network. An intelligent activity monitor 100 may, for example, be configured to communicate via the transceiver 140 through a wired or wireless port to any device or combination or devices selected from the following list: a personal computer, laptop computer, tablet computer, PDA, a watch, an MP3 player, an iPod, a mobile phone, a medical device such as a blood glucose meter, blood pressure monitor, or InR meter, an electronic interactive gaming apparatus, intelligent training equipment, and an automobile system. Data retrieved from the memory 120 or to be stored in memory 120 may, for example, be communicated between the activity monitor 100 and an external device via the transceiver 140. In some embodiments, data transmitted from the activity monitor 100 may be configured for routing to a data service device adapted to process data from an intelligent activity monitor.

In some embodiments, power for the internal electronics of an intelligent activity monitor 100 may be provided by a battery 105 and managed by a wake-up and power-management circuit 150. The battery may, for example, comprise one or more lithium-type batteries that may be rechargeable or replaceable. As an example, a single lithium coin or button cell 3-volt battery having a capacity of about 230 mAh may be used (model CR2032 available from Renata SA of Itingen, Switzerland), though any suitable type of battery may alternatively be used in other embodiments. In some embodiments, an intelligent activity monitor may include power-generation or energy-harvesting hardware (e.g., a piezo-electric material or electric generator configured to convert mechanical motion into electric current, a solar cell, an RF or thermal converter) that may be stored in a battery or charge storage component such as a super capacitor. In some implementations, generated electrical current may be provided to a storage component via a diode bridge. One example of a suitable energy harvesting device is a microenergy cell MEC225 available from Infinite Power Solutions, Inc. of Littleton, Colo. In some embodiments, power generation components may be used in combination with a rechargeable battery as a source of power for an intelligent activity monitor 100.

In some embodiments, wake-up and power-management circuitry 150 may include a motion sensor 152 that, in combination with the wake-up and power-management circuitry 150, identifies when an intelligent activity monitor 100 is being moved in a manner that may be representative of an activity to be monitored. The wake-up and power-management circuitry 150 may, for example, comprise logic and control circuitry to enable, disable, reduce and/or increase power to various circuit elements shown in FIG. 1C. Logic and control circuitry for the wake-up and power-management circuitry may, for example, comprise machine-readable instructions and utilized hardware of the microcontroller 110, or may comprise machine-readable instructions and utilized hardware of an application specific integrated circuit.

In some embodiments, the motion sensor 152 may comprise one or more force sensitive switches, e.g., a piezo element configured to generate an electric signal representative of an amount of acceleration that an intelligent activity monitor experiences. In other embodiments, the motion sensor 152 may additionally or alternatively comprise one or more contact switches that close a circuit, or open a circuit, when the activity monitor is subjected to an acceleration, e.g., a "ball-in-tube" switch that is not force sensitive. Wake-up may, for example, be initiated when a frequency of switch closures exceeds a pre-selected value. In other embodiments, the sensor 152 may additionally or alternatively comprise one or more force-sensitive contact switches that close only when an intelligent activity monitor undergoes acceleration in excess of a pre-selected value.

FIGS. 1D-1E illustrate an example embodiment of an intelligent activity monitor 103 that includes light-emitting diodes (LEDs) 184 for communicating information to a user. The illustrations show the device in plan view (FIG. 1D) and elevation view (FIG. 1E). An intelligent activity monitor may be substantially round, rectangular, square, or be in the form of a multi-sided polygon. An intelligent activity monitor may have a largest dimension D that is between about 5 mm and about 40 mm in some embodiments, and a thickness T that is between about 1 mm and about 10 mm in some embodiments. The size of the intelligent monitor 103 may be largely determined by its power source, e.g., the size of its battery. The intelligent monitor may have a form factor that matches a form of the power source as near as possible. The LEDs may be disposed in a line, a circle, an ellipse, or any other shape. A first cover 170a and second cover 172a may snap or be screwed together, so as to form a seal with a polymer gasket 171a. In some embodiments, a clip or strap may include the polymer gasket 171a, so that the device could be easily changed from a clip-on device to a strap-on device. In some implementations, a clip or strap may removably attach to the first or second covers. In yet other embodiments, a clip or strap may cradle the intelligent activity monitor.

According to some embodiments, an intelligent activity monitor 100 may be configured to recognize one or more tapping sequences and/or motion gestures (e.g., moving the device in a FIG. 8 pattern, a circle pattern, a back-and-forth linear pattern), and activate the LEDs to communicate information responsive to the detected tapping sequence or gesture. A tapping sequence or gesture may correspond to a particular information query, to which the intelligent activity monitor may respond with the appropriate information. According to one embodiment, the intelligent activity monitor may be tapped in a particular manner, and in response activate a number of LEDs to indicate that a user has reached an approximate percentage of an activity goal (e.g., 8 of 10 LEDs to signal approximately 80%). Information about progress toward one or more activity goals can be communicated by the device (e.g., walked 30% of a goal of 3 miles, run 60% of a goal of 8 miles, swam 90% of a goal of 60 laps, etc.) The LEDs may also be used to communicate other information responsive to particular tapping sequences or gestures, e.g., battery life, pace comparison (ahead of, or behind, best pace for an activity), heart rate, calories burned, etc.

Figure 1G:
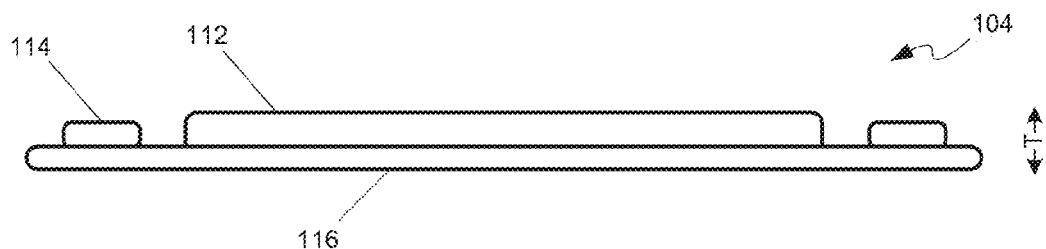
Figure 1H:
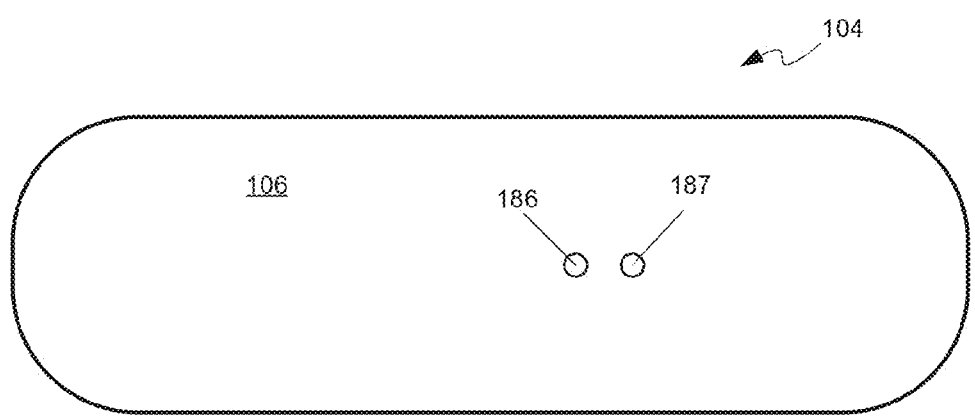

FIGS. 1F-1H illustrate an example embodiment of a fitness sensing system 104. In some implementations, a fitness sensing system may be formed in the shape of a band having a central compartment 112 and fastening features 114. The central compartment 112 may, for example, be attached to a flexible band 106 that can be strapped around a limb of a subject or attached to a subject in any suitable manner (e.g., strapped around an ankle region, a wrist, or an arm). The central compartment may house electronic components 180, 185, 182 (see FIG. 1B) of the fitness sensing system. In some embodiments, the fitness sensing system 104 may include one or more LEDs 184 for conveying information to a user, as described above. In some embodiments, the central compartment may be flexible (e.g., formed of a polymer or elastomer), and electronic components of the monitor may be mounted on a flexible substrate having flexible interconnects. In some embodiments, the central compartment 112 and band 106 are semi-rigid, and the fastening features 114 attach to flexible bands that are used to strap the device to a limb. The fastening features may be holes, button snaps, clasps, or any other suitable fastening feature. The fitness sensing system 104 may, for example, have a length L between about 10 mm and about 50 mm, a width W between about 5 mm and about 30 mm, and a thickness T between about 1 mm, and about 10 mm. Although the fitness sensing system 104 is shown as a substantially flat structure in FIG. 1G, the device may have a curved profile along its length so that is may better conform to the contour of a limb.

According to some embodiments, the fitness sensing system 104 may include at least one light source 186 and at least one photodetector 187. The at least one light source and photodetector may be used, for example, for sensing one or more physiological parameters of a subject, e.g., blood oxygenation level, plethysmography waveforms, blood glucose level, etc. In some embodiments, the light source 186 may comprise a high-brightness infrared (IR) photodiode and a shorter wavelength photodiode. In recent years, progress in indium-gallium-nitride LED technology has yielded devices with both lowered junction voltage and increased radiated intensity. Using InGaN technology, and applying power management techniques described below, may provide a versatile, multi-function heart rate monitor that can run for multiple months on small silver-oxide batteries, fitting a form-factor as that of a typical bandage. The photodetector 187 may be any suitable photodetector, and may be mounted to detect light from the light source that is scattered or reflected from the subject.

Figure 1I:
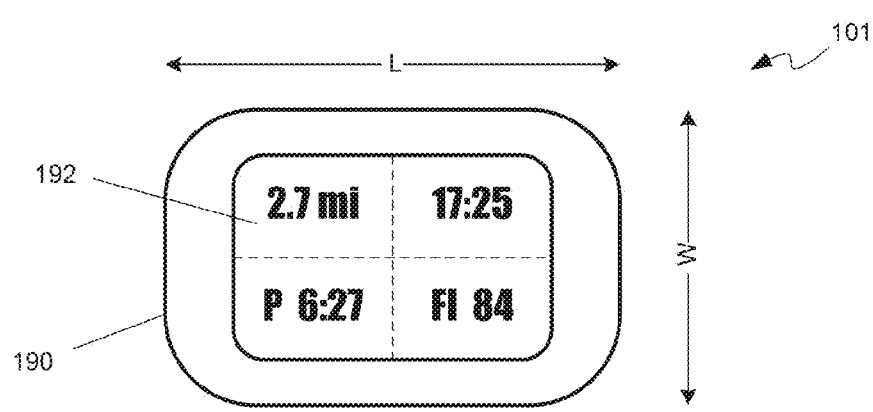
FIG. 1I depicts a versatile display, according to some embodiments.

FIG. 1I depicts an embodiment of a versatile display 101 that may be used in combination with one or more sensors, intelligent sensors, and/or versatile sensors. The versatile display may be used primarily to display data for a use received from one or more sensors in a LAN. The versatile display 101 may include a casing 190 and a display screen 192. The versatile display may include all the electronic components of an intelligent monitor, but may not include sensors of any type in some embodiments. According to some embodiments, a versatile display may establish a LAN and/or participate in a LAN, identify at least one relevant parameter to be displayed, obtain data for the parameter from one or more sensors in the LAN, and configure its display to display at least the one relevant parameter (e.g., provide text or an icon identifying a displayed value).

The versatile display 101 may be useful when a user wishes to view fitness or health data in real time, rather than waiting for a subsequent upload from an intelligent monitor or versatile sensor to a computing device having a display screen. Additionally, the versatile display 101 can be small and light weight and may be worn on the wrist, like a wristwatch. It may have a length L between about 10 mm and about 50 mm, and may have a width W between about 10 mm and about 30 mm. Its small size would be advantageous for a user who does not wish to carry a smart phone, or does not have a smart phone, when exercising.

According to some embodiments, the display screen 192 may provide medium to high resolution for displayed data, e.g., greater than 150 pixels per inch. In some implementations, the resolution may be lower. In various embodiments, the display screen may include touch sensitivity, e.g., a touch-sensitive capacitive matrix having N×M pixels. The touch-sensitive matrix may be low resolution, e.g., N, M<10. In some embodiments, N=M=2, and the display screen 192 may be divided into four touch-sensitive quadrants, as depicted in FIG. 1I. Each touch-sensitive quadrant may be configured to scroll or toggle to a new displayed value or function upon touch. It will be appreciated that a significant number of functions and values may be displayed by simple touching methods, e.g., touching one quadrant may toggle the display in that quadrant to a new parameter or function for execution, touching combinations of two quadrants simultaneously may execute predetermined functions such as "start," "stop," "split time," "upload data," etc.

FIGS. 1J-1K depict an example embodiment of a fitness sensing system 111 that may include at least one versatile sensor, which may comprise an intelligent activity monitor, and include blood glucose monitoring functionality. The sensing system may further include a plethysmogram functionality, in some embodiments. The fitness sensing system 111 may include at least one display, e.g., an arrangement of LEDs 184, a liquid crystal display 192. In some embodiments, a display may comprise a vibration device or acoustic transducer to provide a tactile or auditory notification to a user. According to some embodiments, the fitness sensing system may further include a blood glucose reader (not shown) configured to determine a blood glucose level from a blood sample on a disposable test strip 195. The blood glucose reader may be located internal to the device casing, and test strips with blood samples obtained from a finger prick may be inserted into a slot 177 in the device casing. The blood glucose reader may then read the strip and provide a blood glucose reading. In some implementations, a fitness sensing system may include at least one light source 186 and at least one photodetector 187, as described above in connection with FIG. 1H. The at least one light source may be located to interrogate a region of a subject when the fitness sensing system is attached to or supported by the subject.

According to some embodiments, blood glucose, plethysmography, blood oxygenation levels, and/or heart-rate measurement functionality may be implemented using the at least one light source 186 and the at least one photodetector 187, according to some embodiments. Heart-rate measurements may be made by analyzing plethysmography waveforms in some implementations. Multiple light sources and photodetectors may be used to obtain, non-invasively, blood glucose readings and blood oxygenation levels. Examples of light-source-based blood glucose meters, plethysmograms, and blood oxygenation sensors are described in U.S. Pat. Nos. 5,910,109 and 6,018,673 (the entire disclosures of both patents are incorporated herein by reference). However, any suitable light-source-based sensor may be used. Although the above-referenced patents describe light-based sensors configured to be applied to an earlobe or fingernail, the use of current high-intensity LEDs or laser diodes may enable placement of the at least one light source 186 and at least one photodetector 187 at other locations on a subject, e.g., a wrist, an ankle, an arm, attached to the torso, etc.

According to some embodiments, a non-invasive blood glucose monitor may be controlled to function as a heart rate monitor in one mode of operation. For example, when making a blood glucose reading, multiple (more than two) light sources emitting radiation at multiple wavelengths may be used to probe a region of a subject. In a second mode of operation, a fewer number of light sources (e.g., one or two) may be used to probe the region of the subject to obtain a plethysmography waveform, from which heart rate may be determined.

Although the sensing systems described in FIGS. 1F-1H and FIGS. 1J-1L are depicted as single device in a single package devices, they may take other forms in other embodiments. For example, a fitness/health sensing system may be formed as separately packaged sensors. One package of a fitness sensing system may comprise an intelligent activity monitor (possibly configured as a versatile sensor) that may be supported at a first location on a subject. A second package of the sensing system may comprise a blood glucose monitor (possibly configured as a versatile sensor) that may be supported at a second location on a subject. A third package of the sensing system may comprise a respiratory sensor that may be supported on a torso or neck of a subject. Electronics of the separate packages may communicate to share and process sensed data.

Figure 2:
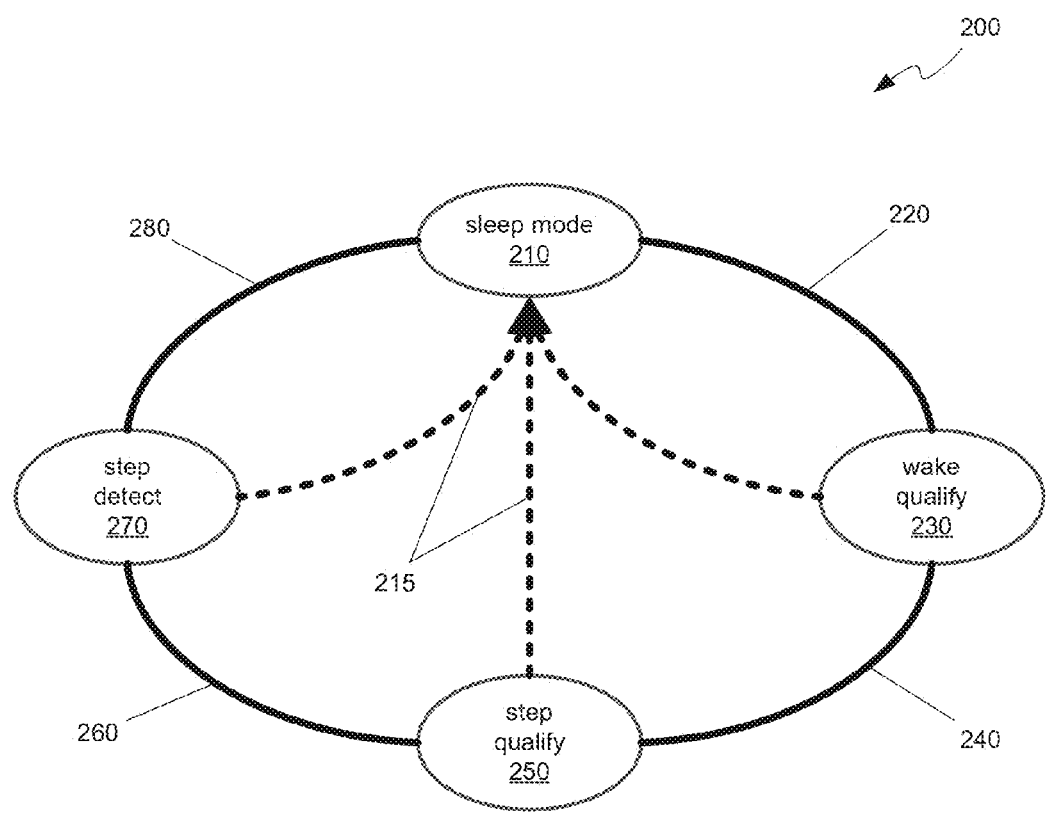
FIG. 2 is an illustrative example of a state diagram for low-energy operation.

Referring now to FIG. 2, in some embodiments, the wake-up and power-management circuitry 150 for an intelligent monitor, versatile sensor, or versatile display may be configured to cycle the device monitor through a plurality of operational states, as shown in the drawing for example. The operational state to which the device is cycled may, for example, depend upon motion detected by the wake-up and power-management circuitry, or data received from another sensor in a LAN. Some of the operational states may, for example, be power-conserving or low-power states.

According to some embodiments, there may be one low-power or no-power state 210 and one or more powered operational states 230, 250, 270. The powered operational states may, for example, include low- or power-conserving states. As illustrated, the activity monitor 100 may move from any one state to any other state along paths 220, 240, 260, 280, 215. In some embodiments, there may be paths in addition to or in lieu of those shown in FIG. 2, e.g., directly from step detect state 270 to wake qualify state 230.

In some embodiments, when an intelligent activity monitor 100 is inactive (exhibiting no motion or motion less than a first pre-selected limit or threshold), the intelligent monitor may operate in sleep mode 210. In some embodiments, sleep mode may consume no power. In other implementations, however, sleep mode may consume low power, e.g., about 1 microamp or less. The low power may, for example, be provided to the motion sensor 152 for detecting a motion of an intelligent activity monitor 100. In some embodiments, no power is provided to any combination of or all of the accelerometer 130, the microcontroller 110, memory 120, and transceiver 140 while in sleep mode. When sufficient motion has been detected via the motion sensor 152, the activity monitor 100 may be moved to a wake qualify state 230.

In some embodiments, sufficient motion for moving the intelligent monitor out of the sleep state 210 may be detected via motion sensor 152 according to an amplitude and/or frequency of a signal from the motion sensor. For example, when the motion sensor comprises one or more piezoelectric elements, a signal greater than a pre-defined signal value may be used to identify sufficient motion of the intelligent activity monitor 100 and move the monitor to wake qualify state 230. In another example, the motion sensor 152 may comprise one or more contact switches, and a pre-defined number of switch openings, or closings, per pre-defined time interval may be used to identify sufficient motion of the activity monitor and move the intelligent monitor to wake qualify state 230.

In some embodiments, when in the wake qualify state 230, low levels of power (e.g., less than about 30 microamps) may be consumed by an intelligent activity monitor 100. Power may, for example, be provided to the accelerometer and to the microcontroller so that data from the accelerometer may be processed while in the wake qualify state 230. Power may, in some embodiments, also be provided to memory 120 while in the wake qualify state. In some embodiments, when in the wake qualify state 230, the system may be clocked at a low rate to conserve power. For example, the microcontroller 110 may be clocked at a low frequency and/or the accelerometer sampled at a low frequency (e.g., less than about 10 Hz) to obtain and process data from the accelerometer. The data may, for example, be processed to determine whether a predefined second threshold has been exceeded. In some embodiments, the second threshold may comprise a pre-defined amount of force or acceleration that an intelligent activity monitor 100 is subjected to, and may include a further parameter, e.g., a frequency of occurrence of measured values exceeding the pre-defined amount of acceleration. When the second threshold is crossed, the activity monitor may, for example, be moved to a step qualify state 250. If the second threshold is not crossed within a pre-defined period of time, the activity monitor may, for example, return to sleep mode 210.

In some embodiments, when in a step qualify state 250, more power is provided to the accelerometer 130 and/or microcontroller 110, so that a greater amount of data processing can occur. The accelerometer and/or microcontroller may, for example, be operated at a higher clock frequency so that a greater amount of data may be obtained from the accelerometer and processed by the microcontroller for a given time interval, as compared with the wake qualify state 230. The power consumed by an intelligent activity monitor in step qualify mode may be on the order of a few hundred microamps, e.g. between about 100 microamps and about 500 microamps in some embodiments. The data-collection rate may, for example, be increased to a normal operating rate in step qualify mode 250. The accelerometer data may, for example, be sampled at several hundred Hertz (e.g., 256 Hz) or higher values. In some embodiments, when in the step qualify mode 250, an intelligent activity monitor 100 may analyze detected acceleration data to determine whether the data is representative of an activity that may be a recognizable activity for the monitor 110, e.g., walking, running, swimming, jumping rope, etc. In some embodiments, if it is determined by the microcontroller that the activity may be recognizable, the intelligent activity monitor may be moved to a step detect state 270. In some embodiments, if it is determined that there is insufficient activity in a pre-defined amount of time to be recognizable by the microcontroller, then the activity monitor may return to wake qualify mode 230.

In some embodiments, when in step detect mode 270, an intelligent activity monitor may be placed in full operation. In this mode, power may, for example, be provided to transceiver 140, in addition to the other operational components so that communications with an external device may be carried out. In some embodiments, normal operating clock frequencies and sampling rates may be used for operating the accelerometer and microcontroller, so that activity detection and full data processing may be carried out. Power consumption in step detect mode 270 may, for example, be several hundred microamps, e.g., between about 200 microamps and about 600 microamps.

In some embodiments, each operational state other than sleep mode 210 may include a provision for returning an intelligent activity monitor directly to sleep mode, e.g., along state paths 215 as indicated in FIG. 2. For example, each operational state 230, 250, 270 may be configured to return an intelligent activity monitor 100 to sleep mode 210 if there is a termination of incoming data or of processed data parameters associated with incoming data. In some embodiments, the activity monitor may additionally or alternatively be configured to return to sleep mode upon a system glitch or crash, e.g., a freezing of the microcontroller. A return to sleep mode may, for example, be used to reset an intelligent activity monitor.

III. Overview of Data Processing

This section provides an overview of example data handling and data processing architectures that may be implemented with various embodiments of a fitness sensing system. The data processing may be carried out on an intelligent monitor or a versatile sensor. Although the following discussion of data processing is directed primarily to an intelligent activity monitor, the data processing may be carried out on a versatile sensor in some applications. With reference to the block diagram of FIG. 3A, an illustrative example of a data handling and processing architecture 300 is shown. Another example of such an architecture is depicted in FIG. 3B. It should be appreciated that other embodiments may include fewer, additional, or different elements than those shown in FIGS. 3A-3B. Moreover, it should be appreciated that, in some embodiments, one or more depicted elements may be combined into a single unit providing equivalent functionality of both units depicted separately.

Figure 3A:
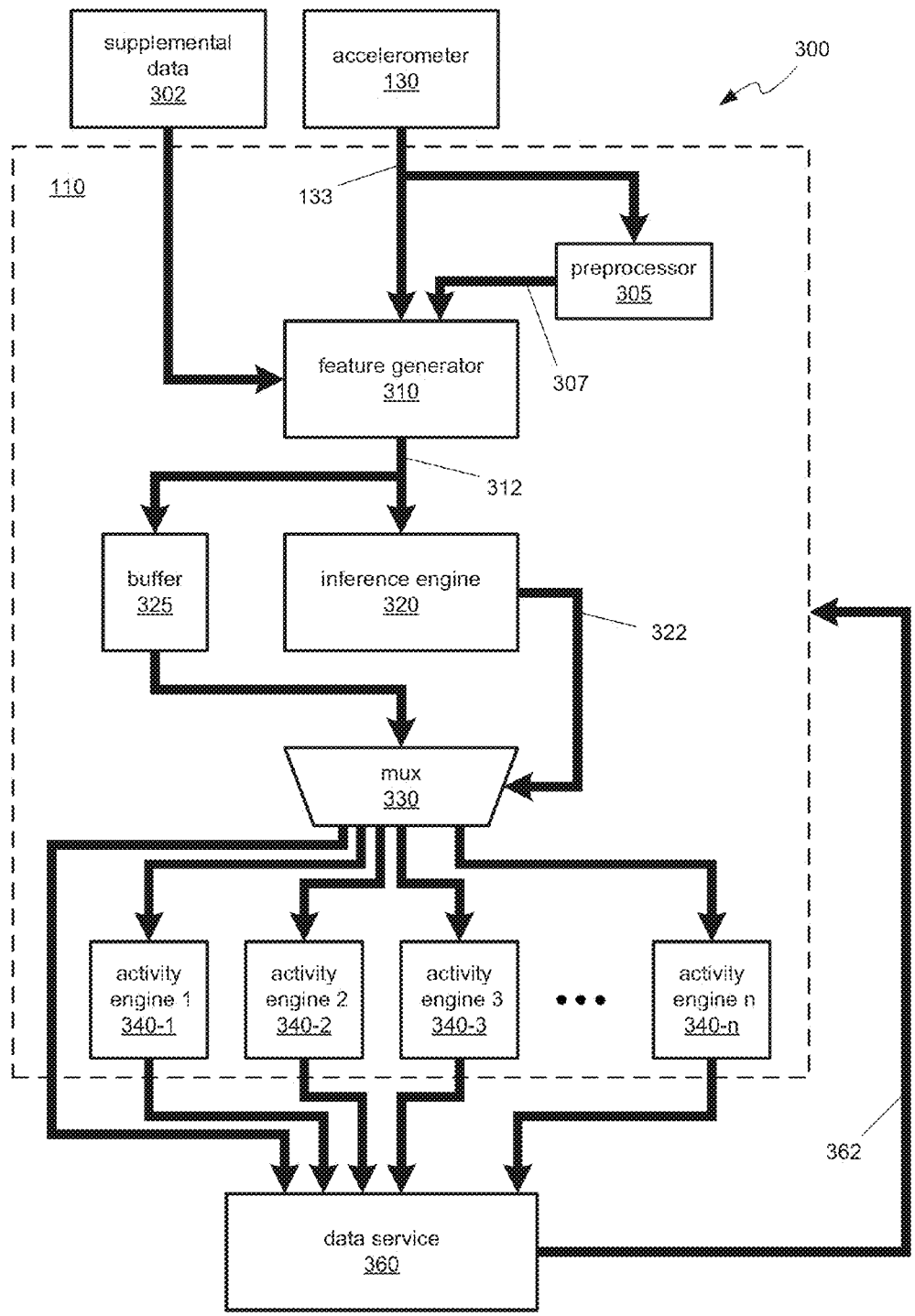
FIG. 3A depicts an example of an architecture for data flow and data handling elements of a versatile sensor, according to some embodiments.
Figure 3B:
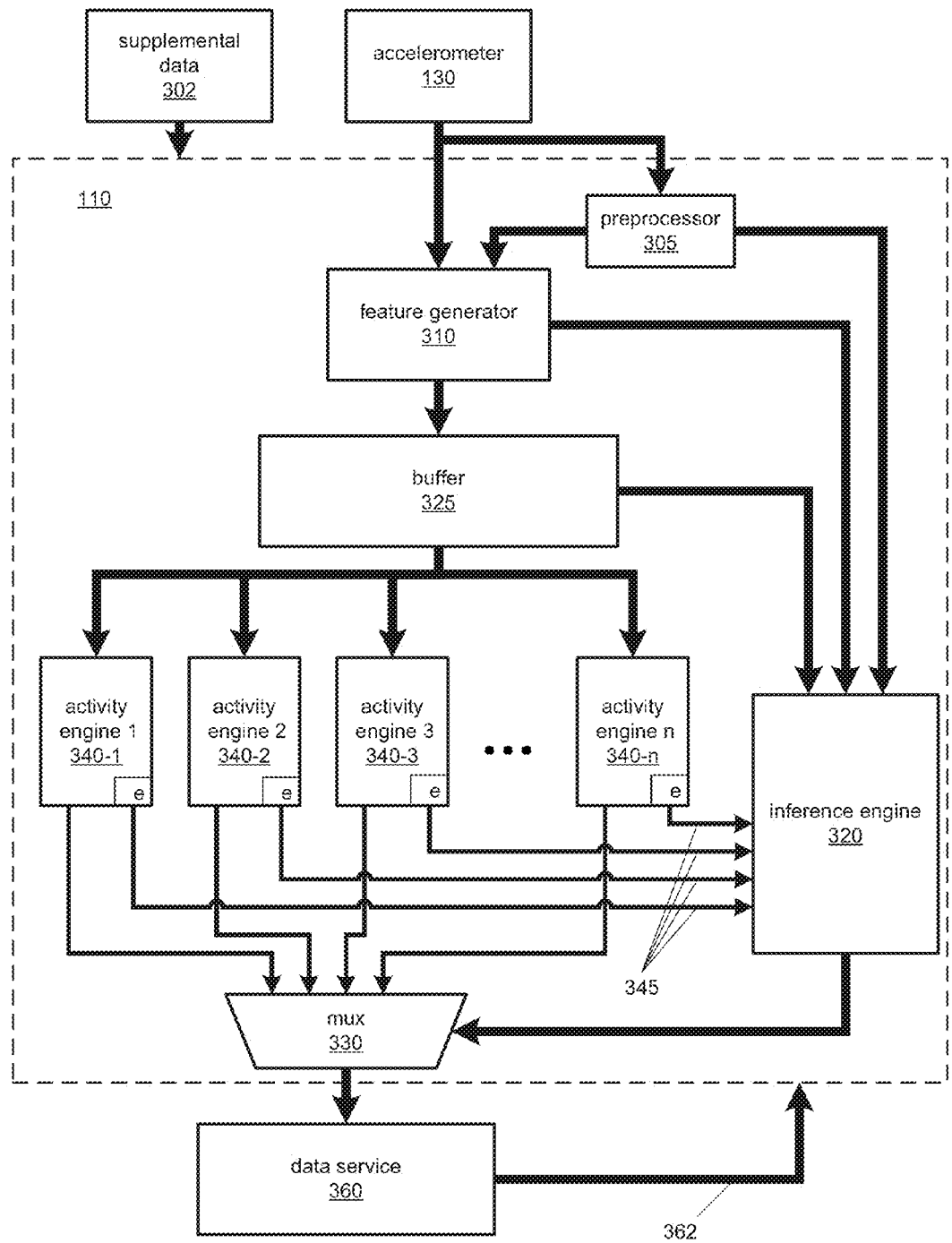
FIG. 3B depicts another example of an architecture for data flow and data handling elements of an activity monitor.

As illustrated in FIG. 3A, in some embodiments, the accelerometer 130 may be configured to output a data stream 133 of values representative of acceleration detected by the accelerometer along at least one direction of motion. The data stream 133 may, for example, comprise acceleration values representative of acceleration measured along respective X-, Y-, and Z-axes of motion defined by the accelerometer 130. In some embodiments, the data stream 133 of acceleration values may be provided to both a feature generator 310 and a preprocessor 305. In some implementations, supplemental data 302, received from physiological sensors, may be provided to the feature generator 310 and/or preprocessor 305. The preprocessor 305 may, for example, pre-process the data stream 133 from the accelerometer, as described in the following section, to produce a stream of acceleration-derivative values 307 that is provided to the feature generator 310.

In certain embodiments, the feature generator 310 may process the received data stream 133 of acceleration values, supplemental data, and the stream of acceleration-derivative values 307 to produce one or more characteristic features 312 that may be provided to an inference engine 320 and optionally to a buffer 325. The characteristic features may, for example, be used by the inference engine 320 to identify a type of activity sensed by the accelerometer 130 from among a plurality of types of activities when the accelerometer is supported by a subject in motion. In some embodiments, upon the identification of activity, the inference engine 320 may provide a control signal 322 to a multiplexor 330 to route the characteristic features 312 to an appropriate activity engine 340-1, 340-2, . . . , 340-n for further data analysis. Each activity engine may, for example, be configured to process received characteristic features according to activity-specific (e.g., running, walking, swimming, biking, etc.) algorithms to calculate one or more parameters descriptive of the activity. Illustrative examples of the one or more parameters include, but are not limited to, a measure of intensity or pace of the activity, a measure of energy expended during the activity, a measure of distance traveled during the activity, and a duration of the activity.

In some embodiments, parameters characteristic of the activity may be provided to and handled by data service 360. The data service 360 may, for example, comprise an on-board data store, e.g., memory 120, and a transceiver 140 for transmitting the data to a remote device, such as a computer. In some embodiments, data service may additionally or alternatively include an application in operation on a remote computer or a remote server configured to receive data from the activity monitor and record and/or further process the received data.

In some embodiments, any of the preprocessor 305, feature generator 310, inference engine 320, multiplexor 330, and activity engines 340-1-340-n may be embodied in whole or in part as machine-readable instructions operable on microcontroller or microprocessor 110 to adapt the microcontroller to perform a respective functionality as described above or in the following sections. Further, any of the preprocessor 305, feature generator 310, inference engine 320, multiplexor 330, and activity engines 340-1-340-n may additionally or alternatively be embodied in whole or in part as hardware configured to perform a respective functionality.

According to some implementations, inference engine 320 may be additionally or alternatively be configured to identify non-recognized activities as well as activities that are not performed by a human. For example, inference engine may receive a set of characteristic features 312 that cannot be identified as corresponding to any one of a plurality of activities recognizable by the inference engine. In this case, the data-handling architecture may, for example, be configured to provide the characteristic feature set data 312 directly to data service 360 for subsequent analysis and determination of a type of activity associated with the feature set. For example, the feature set data 312 may be routed by the multiplexor 330 from the buffer 325 to data service 360. Further, the data-handling architecture may be additionally or alternatively configured to receive machine-readable instructions and reconfiguration data 362 back from data service 360 suitable to reconfigure inference engine 320 to subsequently identify a type of activity corresponding to the previously non-recognizable feature set. In this manner, activity recognition by the activity monitor 100 may, for example, be upgraded or reconfigured at any time.

In some embodiments, a non-recognized activity may be reported to a user at a later time for subsequent identification by the user. For example, a non-recognized activity may be reported when the user is reviewing a record of monitored activities via a computer. The user may, for example, be notified that a non-recognizable activity occurred at a specific date and time and for a duration, and then the user may be queried to identify the activity. In some embodiments, the user may then identify the activity, which will in turn associate a set of characteristic features 312 with the previously non-recognized activity. In some embodiments, the system may be adapted to learn from the user identification that the previously non-recognized set of characteristic features 312 are now recognizable, and subsequently update inference engine 320 to recognize any subsequent activity exhibiting a same or similar set of characteristic features. The updating of the inference engine 320 may, for example, comprise transmitting new data structures and/or code to the microprocessor 110 for use in recognizing the new activity.

In some implementations, inference engine 320 may be configured to recognize one or more activities that are not performed by a human. One example of such an activity might be cyclic motion of a fan, wherein the activity monitor 100 may be strapped to the blade of a fan. Another example might be motion of an automobile or motorized vehicle. Another example might be motion of a bicycle wheel, e.g., monitor attached to spokes of a wheel. Other examples of activities not performed by a human might be motion in a clothes drying or clothes washing machine. Another example may include walking or running motion of a dog or horse. In some cases, the activities not performed by a human may, for example, be recognized to aid in preventing mis-recording of data generated to falsify human activity, e.g., in connection with health insurance incentive programs.

According to some embodiments, the inference engine 320 may be configured to further qualify data based on the combined activity and physiological features. For example, a versatile sensor comprising a heart rate monitor, respiratory monitor, blood oxygenation monitor, or blood glucose monitor, or any combination thereof, may detect a significant change in a subject's physiological parameter that might indicate an alarm condition. The versatile sensor may then request data from the activity monitor, and the inference engine 320 process features of the activity data to determine whether the subject has changed their activity level, e.g., from a resting state to an active state.

Another illustrative embodiment of a data flow and data handling architecture 301 is shown in FIG. 3B. The front end of the data processing is similar to that shown in FIG. 3A, however, in the embodiment of FIG. 3B, the inference engine 320 is configured to further receive data from preprocessor 305 and buffer 325, as well as error signal indication 345 from each activity engine 340-1 . . . 340-n. The error signal may, for example, represent a confidence level of an activity processed by an activity engine. For example, a first activity engine 340-1 may be an activity engine for walking, and a second engine 340-2 an engine for running. When the user is walking, for example, a step cadence may be below a threshold criterion for running, and an output error signal from the running activity engine 340-2 might be high. The output error signal may, for example, be used by inference engine 320 to aid in identifying an activity. In some embodiments (e.g., the embodiment of FIG. 3B), all activity engines may substantially simultaneously process feature data, whereas in other embodiments (e.g., the embodiment of FIG. 3A) only one activity engine or a selected number of activity engines may be selected to process feature data.

In some implementations, supplemental data 302 may be provided to one or more processing devices of the microcontroller or microprocessor 110. For example, supplemental data 302 may be provided to any one or combination of preprocessor 305, feature generator 310, and inference engine 320. Supplemental data 302 may also be provided to buffer 325, in some embodiments.

It should be appreciated that error signaling from activity engines may, for some applications, also be employed in the embodiment shown in FIG. 3A. For example, error signals from activity engines 340-1 . . . 340-n may be fed back to inference engine 320. The presence of a large error signal for a currently identified activity may, for example, cause inference engine 320 to re-identify an activity for newly received data.

In some embodiments, the buffer 325 may be used in various embodiments to temporarily retain data representative of an activity while inference engine 320 identifies an activity. For example, once an activity has been identified, data may be routed from the buffer to the appropriate activity engine or engines. Such temporary buffering of data prevents loss of activity data during initial identification of an activity or transitions from one activity to another.

IV. Pre-Processing of Accelerometer Data

Referring again to FIGS. 3A and 3B, it should be appreciated that, in some embodiments, data handling and processing architecture 300, 301 may include a data preprocessor 305 and a feature generator 310. In some implementations, preprocessor 305 may, for example, filter acceleration values received from at least one axis of the accelerometer 130 to reduce noise in the data. In some embodiments, the preprocessor 305 may additionally or alternatively calculate derivatives of values from the acceleration values received from at least one axis of the accelerometer 130. Furthermore, in some embodiments, the preprocessor 305 may additionally or alternatively parse the received data stream into blocks of data for subsequent data processing. As described above, in some embodiments, the feature generator 320 may generate a set of characteristic features 312 that are representative of the received signals from the accelerometer 130 and preprocessor 305, and the features may subsequently be used to identify a particular activity from among a plurality of different activities as well as identify a location at which an intelligent activity monitor may be worn.

In certain embodiments, the preprocessor 305 may compute derivatives of acceleration values (also referred to herein as "acceleration-derivative values") by calculating changes in acceleration values with respect to time according to the relation $$D_{i,n} = \frac{a_{i,n} - a_{i,n-1}}{dt} \quad (1)$$

where $D_{i,n}$ is an $n^{th}$ computed acceleration-derivative value along an $i^{th}$ directional axis in a data stream of acceleration-derivative values, $a_{i,n}$ represents an $n^{th}$ acceleration value detected by the accelerometer along an $i^{th}$ axis of the accelerometer (e.g., an X axis), and dt is a time difference between the detected acceleration values $a_{i,n}$ and $a_{i,n-1}$. The sensed acceleration values $a_{i,n}$ and $a_{i,n-1}$ may, for example, be samples of acceleration values obtained via analog-to-digital conversion. In some embodiments, the acceleration values $a_{i,n}$ may be obtained at regular intervals (e.g., all values of dt are equivalent between successive values of $a_{i,n}$) and the derivative of EQ. 1 may be expressed as $$D_{i,n} = a_{i,n} - a_{i,n-1} \quad (2)$$

wherein the derivative with respect to time is implicit. Regular intervals of sampling may, for example, result from analog-to-digital conversion of the analog output of acceleration values from the accelerometer.

In some embodiments, computed acceleration-derivative values for multiple axes of the accelerometer 130 may be combined by preprocessor 305 for each time sample, e.g., summed together. In some implementations, an absolute value of the sum, or a squared value of the sum in some embodiments, may be computed after combining the values. In some embodiments, acceleration-derivative values for multiple axes of the accelerometer 130 may be combined according to the following relation $$D_n = \sum_{i=1}^{m} |D_{i,n}| \quad (3)$$

where $D_n$ represents an $n^{th}$ combined acceleration-derivative value in a data stream of combined acceleration-derivative values, and m represents a number of axes for which acceleration-derivative values are combined. For some embodiments employing EQ. 3, the absolute value of acceleration-derivative values $D_{i,n}$ may, for example, be taken prior to combining the acceleration-derivative values. It should be appreciated that a stream of values $D_n$ may, for example, be produced as new acceleration values 133 are received and processed by the preprocessor 305.

In some embodiments, similar approaches for computing and combining acceleration-derivative values like the approaches shown in EQS. 1-3 may additionally or alternatively be employed. Such approaches may, for example, include computing acceleration-derivative values using different acceleration values (e.g., $[a_{i,n+1}-a_{i,n}]$), using a greater number of consecutive acceleration values to compute an average acceleration-derivative value, and squaring acceleration-derivative values when combining the values (e.g., $[D_{i,n}]^2$) rather than taking an absolute value. In some cases, the absolute value may not need to be taken when summing derivative values. Also, in some embodiments, raw accelerometer data may be smoothed, averaged, up-sampled, or down-sampled prior to computing combined acceleration-derivative values.

Additional embodiments of computing combined acceleration-derivative values are also contemplated. First derivative values may, for example, be computed in accordance with EQ. 2 above, or approximated in accordance with the following expression.

$$D_{i,n} = a_{i,n} - a_{i,n-m} \quad (4)$$

where m may be an integer greater than 1, e.g., 2, 3, 4, or greater.

In some embodiments, second derivative values may be computed in addition to, or instead of, first derivative values. The second derivative values $C_n$ may be computed from the $D_n$ values, e.g., $$C_{i,n} = D_{i,n} - D_{i,n-m} \quad (5)$$

where m may be an integer greater than or equal to 1, and $D_{i,n}$ is an $n^{th}$ computed acceleration-derivative value along an $i^{th}$ directional axis. The values $C_{i,n}$ may be combined in any manner as described above in connection with the combination of the $D_{i,n}$ values.

In some embodiments, the stream of acceleration-derivative values $D_n$ may be used by inference engine, alone or in combination with other data values, to identify activities detected by activity monitor 100. In some implementations, for example, the stream of acceleration-derivative values $D_n$ may be used by an activity engine, alone or in combination with other data values, to compute parameters characterizing a recognized activity.

By combining and computing the acceleration-derivative values $D_n$ as described above, a strategy for identifying activities and/or analyzing activity-generated data that can reduce the computational load on the microcontroller may be employed in some embodiments. Further, it may not be necessary for the microcontroller to determine which axis of the accelerometer provides the most relevant data, nor to track an orientation of the accelerometer during operation to analyze activity-generated data since the acceleration-derivative values tend to emphasize high-frequency variations. The computation of acceleration-derivative values $D_n$ as described above may, for example, provide a more stable activity analysis algorithm across various types of activities.

In some embodiments, the stream of acceleration-derivative values $D_n$ may provide better data and less data for identifying activities and/or analyzing activity-generated data than one or more data streams of raw acceleration data 133. The stream of acceleration-derivative values $D_n$ may, for example, accentuate higher frequency components of a raw acceleration data stream that are useful in identifying and/or analyzing an activity and suppress low frequency components of raw acceleration data streams that contribute to noise or are less useful in identifying or analyzing an activity. Additionally, in some embodiments, by combining the raw data to produce the stream of acceleration-derivative values $D_n$, there may be less data-processing burden on inference engine 320, e.g., it may receive one data stream of acceleration-derivative values $D_n$ rather than three data streams of raw acceleration data from each axis of accelerometer 130. The stream of acceleration-derivative values $D_n$ may, for example, be passed by feature generator 310 to inference engine 320 in some embodiments.

In some embodiments, the feature generator 310 may receive raw data from the accelerometer 133 and data from the preprocessor 305 to produce one or more features to include in a set of characteristic features 312 that are provided to inference engine 320. It should be appreciated that sets of characteristic features 312 may, for example, be provided to inference engine 320 on a periodic or semi-periodic basis as new data is received by feature generator 310. Such a set of characteristic features 312 may, for example, comprise a data structure that includes one or more data entries representative of a detected activity. Examples of such data entries include, but are not limited to, any of the following or combination thereof: an array of acceleration-derivative values $D_n$ for a pre-selected time interval, one or more arrays of raw acceleration data corresponding to the same time interval, a maximum and/or minimum value of the acceleration-derivative values $D_n$ within the time interval, a maximum and/or minimum value of the raw acceleration data within the time interval, phase shifts between two or more cyclic patterns of the raw acceleration data, a number of peaks of the acceleration-derivative values $D_n$ within the time interval, a distance between peaks, a width of at least one peak, a maximum rate of signal change at the onset of a peak. It should be appreciated that other aspects of received signals may additionally or alternatively be included in a set of characteristic features 312 that is constructed to represent a detected activity.

In some embodiments, a set $F_n$ of characteristic features $f_n$ may be represented symbolically, according to one example and for teaching purposes only, as follows $$F_n = \{f_1, f_2, f_3 \ldots f_n\} \quad (6)$$
$$= \{(D_n, D_{n+1}, \ldots D_{n+m}), P_1, \Delta P_1, P_2, \Delta P_2, dP_{12}\}$$

where $f_n$ represents an $n^{th}$ feature in the set, m represents a number of acceleration-derivative values $D_n$ calculated within a pre-selected time interval, $P_1$ represents a largest peak value of the acceleration-derivative value array ($D_n$, $D_{n+1}, \ldots D_{n+m}$), $P_2$ represents a second largest peak value of the acceleration-derivative value array ($D_n$, $D_{n+1}, \ldots D_{n+m}$), $\Delta P_n$ represents a width of the $n^{th}$ peak, and $dP_{12}$ represents a distance between peaks $P_1$ and $P_2$. Each set $F_n$ of characteristic features may, for example, be operated on by inference engine 320 to identify an activity type. In some embodiments, such a feature set may additionally or alternatively include a number of raw acceleration values from one or more axes of the accelerometer. In some implementations, a feature set may, for example, be treated as a vector for calculation purposes.

In some embodiments, data received from the accelerometer 120 may also be compressed and/or filtered by preprocessor 305 or feature generator 310. For example, data from the accelerometer may be streamed to preprocessor at a rate of P samples per second per axis. (P may be any value such as 64, 100, 128, 200, 256, 300, 400, 500, 512, 1024, for example.) Preprocessor may, for example, compress the data streams by averaging q values and outputting one averaged value for each q values. (q may be any integer value, e.g., 2, 4, 5, 8, 10.) In some embodiments, filtering may additionally or alternatively be employed by preprocessor or feature generator to smooth a data stream.

In some implementations, data may be scaled by preprocessor 305 or feature generator 310. For example, an autogain algorithm may be used to adjust accelerometer signal levels to utilize a full range, or near full range, of bits in an A-to-D converter when the raw signal level is too strong or too week. This may, for example, allow for a better capture of a waveform with higher resolution. When gain is adjusted automatically, in some embodiments, the system may be configured to provide a gain setting or scaling value along with the data, so that absolute values of the data may be determined.

In some embodiments, data reduction may occur along the direction of flow of data within the data handling architecture. For example, the raw data 133 (e.g., three acceleration data streams) from the accelerometer may be preprocessed as described above to pass only a compressed and combined acceleration-derivative data stream and/or several features to the inference engine 320 or an activity engine 340-m.

V. Identification of Activities

As noted above, in some embodiments, data generated by the accelerometer 130 may be processed by preprocessor 305 to produce acceleration-derivative data $D_n$ and processed by feature generator to produce characteristic features $f_n$ that are provided to the inference engine 320. In some embodiments, raw acceleration data may additionally or alternatively be provided to inference engine. The Inference engine 320 may, for example, be configured to receive processed data, and in some cases raw data, and further process the received data to identify an activity sensed by the accelerometer. In some embodiments, the activity identified may be one activity from among a plurality of different activities that include activities performed by a human as well as activities that are not performed by a human.

In some implementations, the inference engine 320 may identify an activity using acceleration-derivative data $D_n$ only, or a combination of acceleration-derivative data and a limited set of additional characteristic features. In some embodiments, the inference engine 320 may identify an activity using one or more raw accelerometer traces and/or characteristic features generated from the one or more raw traces. Further, in some embodiments, the inference engine may additionally or alternatively qualify (e.g., identify a level of quality of the recognized activity's data or identify an aspect of the recognized activity such as a location of the activity monitor on the subject) using any combination of acceleration-derivative data $D_n$, raw accelerometer data, and related characteristic features.

In some embodiments, the inference engine 320 may employ one or more identification algorithms to identify or distinguish activities. For example, in some embodiments, the inference engine 320 may employ a pattern recognition algorithm to recognize an activity based upon a waveform defined by acceleration-derivative data $D_n$ and/or one or more raw accelerometer traces. In some embodiments, the inference engine 320 may additionally or alternatively employ fuzzy logic to identify an activity based upon a number of values in characteristic feature sets $F_n$. The inference engine 320 may thus, in some embodiments, employ a combination of pattern recognition and fuzzy logic to identify an activity. It should be appreciated that other "recognition" algorithms or combinations of such algorithms may additionally or alternatively be used.

In some embodiments, for fuzzy logic recognition, membership functions specific to different activities may be defined and downloaded to the activity monitor 100. For example, data received by inference engine 320 that has a predetermined number of values falling within a membership function range may be identified by inference engine as an activity associated with that membership function. For some implementations, fuzzy logic may be suitable for recognizing a large variety of different activities without placing a heavy data-processing burden on microcontroller 110. For example, fuzzy logic may, in some embodiments, require only determining whether a plurality of characteristic features from feature data $F_n$ fall within certain ranges of values. In other embodiments, fuzzy logic may additionally or alternatively evaluate a cost factor for each candidate activity and identify an activity based upon a maximal value of the cost factor.

Figure 4A:
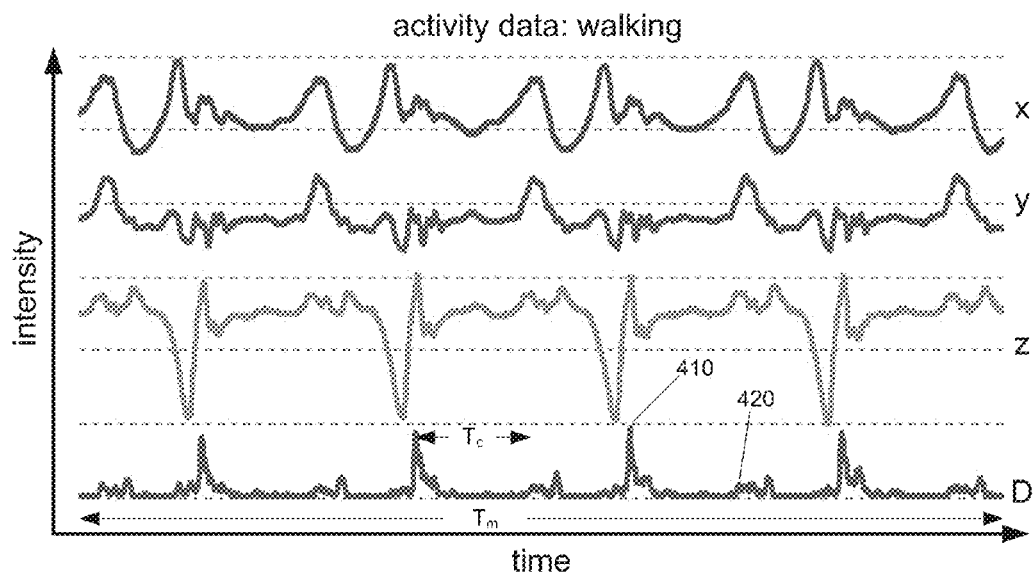
FIGS. 4A-4E depict illustrative examples of multi-axis accelerometer data and combined acceleration-derivative data for various types of activities.
Figure 4B:
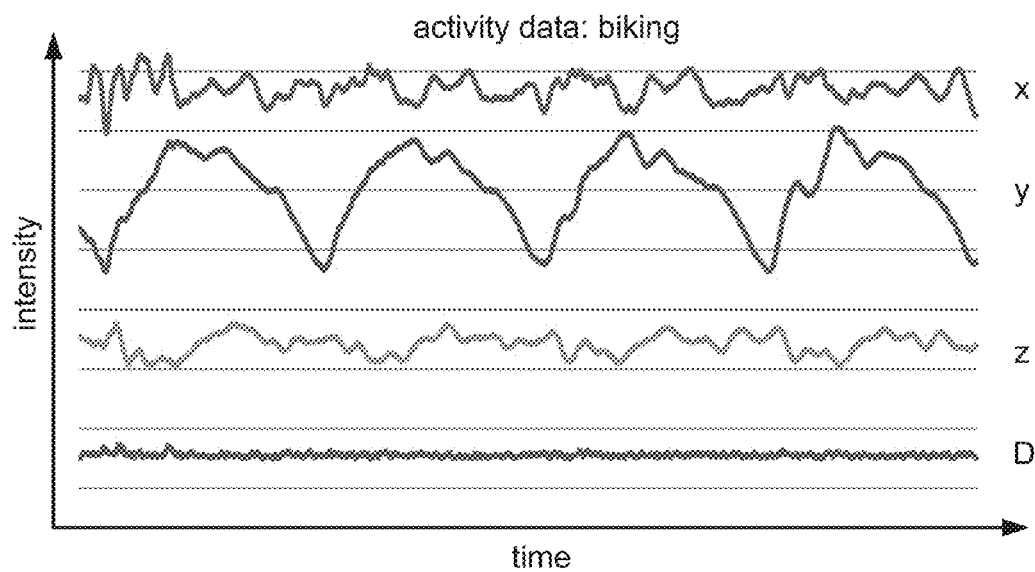
Figure 4C:
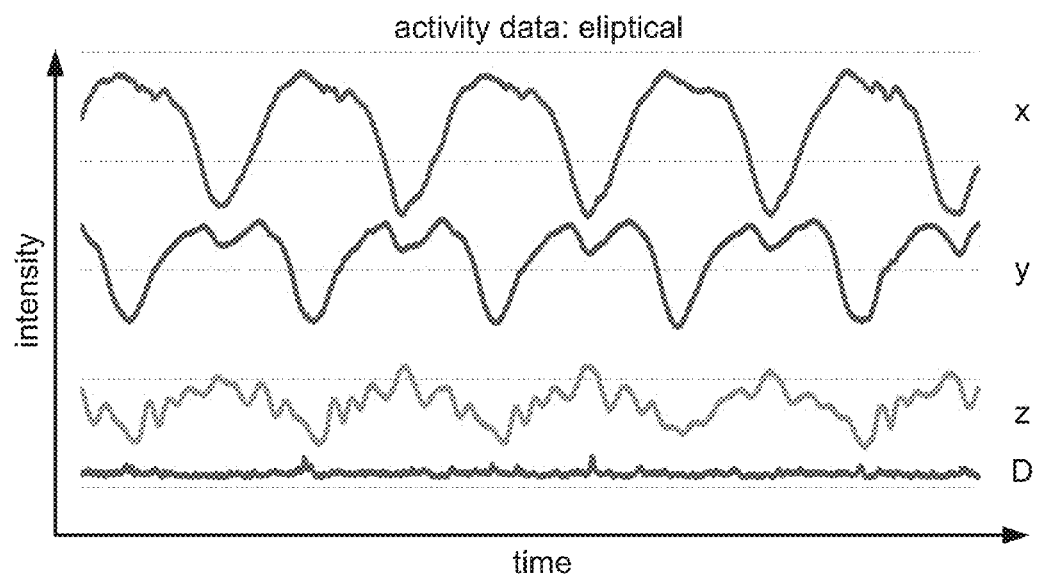
Figure 4D:
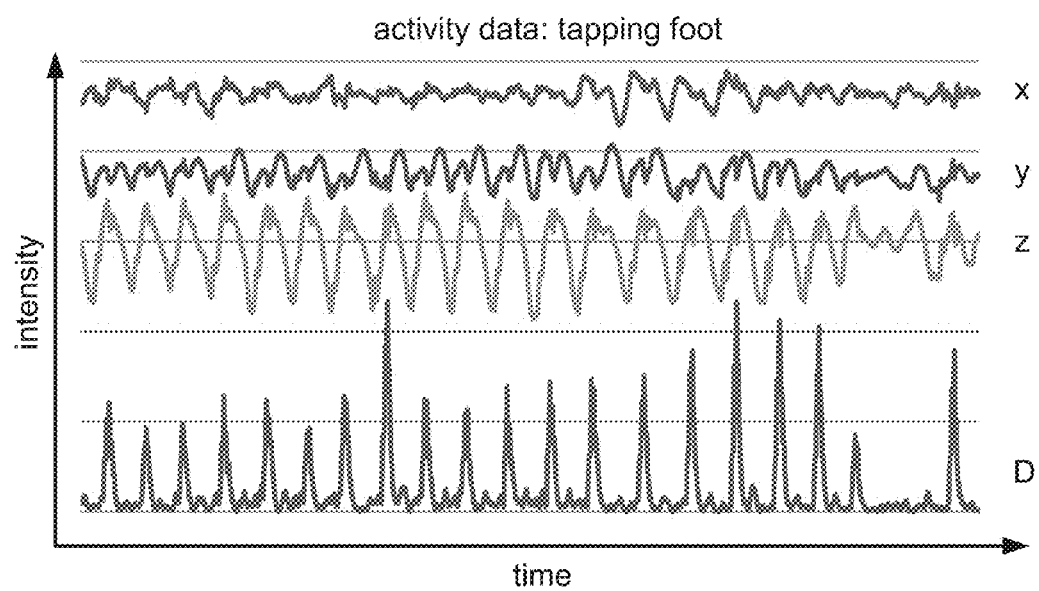
Figure 4E:
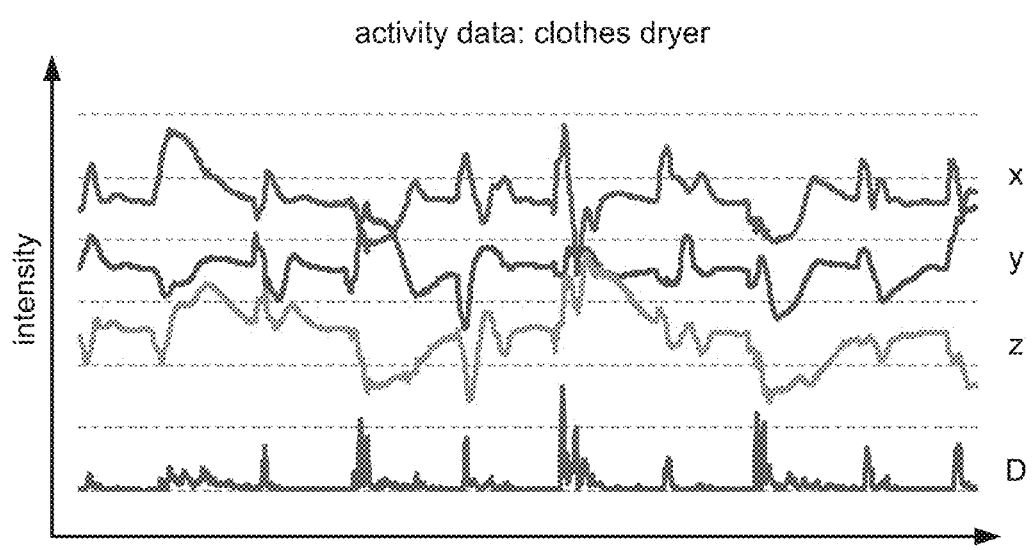

For purposes of understanding only, and without limiting the invention, one example of activity identification is described with reference to FIGS. 4A-4E. FIG. 4A represents three traces (x, y, z: top three) of raw acceleration data from a first type of activity (walking in this example). The lower trace D in FIG. 4A represents acceleration-derivative data computed from the upper traces in accordance with EQ. 3. FIG. 4B represents corresponding traces of data obtained from a second type of activity (biking in this example). FIG. 4C represents three traces of raw acceleration data and acceleration-derivative data from a third type of activity (elliptical training). FIG. 4D represents three traces of raw acceleration data and acceleration-derivative data from a fourth type of activity (tapping foot). FIG. 4E represents three traces of raw acceleration data and acceleration-derivative data from a fourth type of activity (motion in a clothes dryer). For all data shown in FIGS. 4A-4D the activity monitor 100 was supported either on the user's foot or ankle.

In some embodiments, an intelligent activity monitor or versatile sensor may receive physiological data from one or more additional sensors. As an example, the intelligent monitor 100 may receive pleth data, depicted in FIG. 4F, and/or respiratory data, depicted in FIG. 4G. In some implementations, the intelligent monitor or versatile sensor may analyze the received physiological data to determine the data type in the same manner that motion data is analyzed to determine an activity type. In some cases, the physiological data may be identified when provided to the intelligent monitor or versatile sensor, e.g., identified in a header associated with the data, or by an identification number or tag associated with the physiological sensor. An intelligent activity monitor or versatile sensor may process the physiological data in combination with the activity data to enhance information about a subject.

As can be seen from the traces of FIGS. 4A-4G, there are a number of differences in the traces. The differences include maximum and minimum values of acceleration, periodicity of the traces, number and shapes of peaks in the traces, width of peaks, and distances between peaks, among other things. The differences may, for example, be captured in characteristic feature sets $F_n$ for each trace.

Continuing with the above example, in some embodiments, a characteristic feature set for each trace within a measurement interval $T_m$ may be constructed with the following entries:

$F_n$={max value of trace (max); min value of trace (min); number of peaks with a width less than $m_1$ samples ($N_p$); number of valleys with a width less than $m_2$ samples (N); average rate of change of the trace at half-maximum of peaks ($R_{1/2}$); average distance between peaks ($\Delta P$)}. It should be appreciated that a wide variety of characteristic features may be generated and used to identify the different activities. As can be understood from this example, the differences in the traces of FIGS. 4A-4E may, for example, be captured as numerical differences in the characteristic feature sets. In some embodiments, the inference engine 320 may then distinguish between the activities based upon such numerical differences. A judicious choice of values to include in feature sets may, in some embodiments, reduce the computational burden on inference engine 320 and enable rapid identification of different types of activities.

In some implementations, by sampling a large number of trials for each activity, variations in each of the characteristic feature values may be observed and statistics regarding the variations may be determined. The statistical results may, for example, be used to construct membership functions for fuzzy-logic activity identification. For example, it may be observed that a maximum value of acceleration-derivative trace D for running has a 2-sigma variation of 5 measurement units. A membership function for running may, for example, include the specification {(120−5)≤max value of D≤(120+5)}, where 120 measurement units is determined to be an average of the maximum value for trace D for the running activity. Continuing with the example above, a membership function for each of the activities may, for example, be defined as follows:

$$M_{activity} = \begin{cases} (\max_{avg} - \partial \max) \leq \max \leq (\max_{avg} + \partial \max); \\ (\min_{avg} - \partial \min) \leq \min \leq (\max_{avg} + \partial \max); \\ (N_{p,avg} - \partial N_p) \leq N_p \leq (N_{p,avg} + \partial N_p); \\ (N_{v,avg} - \partial N_v) \leq N_v \leq (N_{v,avg} + \partial N_v); \\ \left(R_{\frac{1}{2},avg} - \partial R_{\frac{1}{2}}\right) \leq R_{\frac{1}{2}} \leq \left(R_{\frac{1}{2},avg} + \partial R_{\frac{1}{2}}\right); \\ (\Delta P_{avg} - \partial \Delta P) \leq \Delta P \leq (R\Delta P_{avg} + \partial \Delta P) \end{cases} \quad (7)$$

where the subscript "avg" designates an average or expected value, and the quantities ±∂[ ] identify a pre-defined range within which a measured value would be considered to qualify as belonging to the membership function. In some embodiments, when characteristic features are received by the inference engine 320, for which all values qualify as belonging to the membership function, then the detected activity may be identified by the inference engine. The inference engine may then, for example, route the data from the feature generator, using multiplexor 330 to an appropriate activity engine for further analysis.

In some instances, there may be partial overlap of membership functions. For example, one or more ranges for characteristic features in one membership function may overlap or be coincident with corresponding ranges in a second membership function. Even though there may be partial overlap of membership functions, in some implementations, an activity may be identified based on non-overlapping characteristic features. For example, each activity may receive a score (e.g., a value of 1) for each feature that falls within the membership function for that activity. In some embodiments, after scores have been tallied for each activity, the one receiving the highest score may be selected as the identified activity.

Figure 5A:
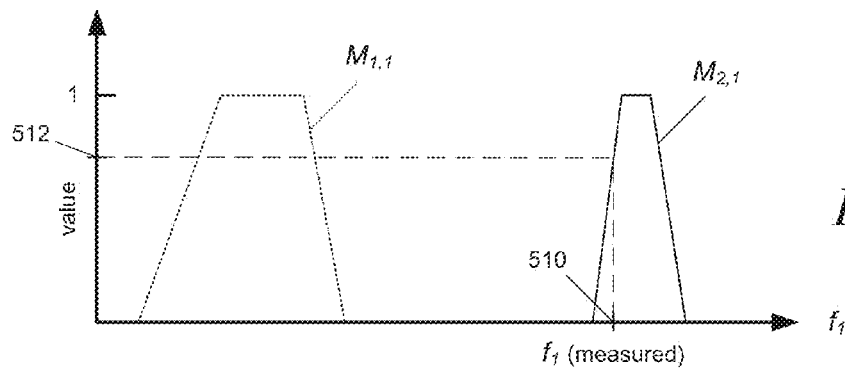
FIGS. 5A-5C illustrate examples of membership functions that may be used in fuzzy-logic identification of activities.
Figure 5B:
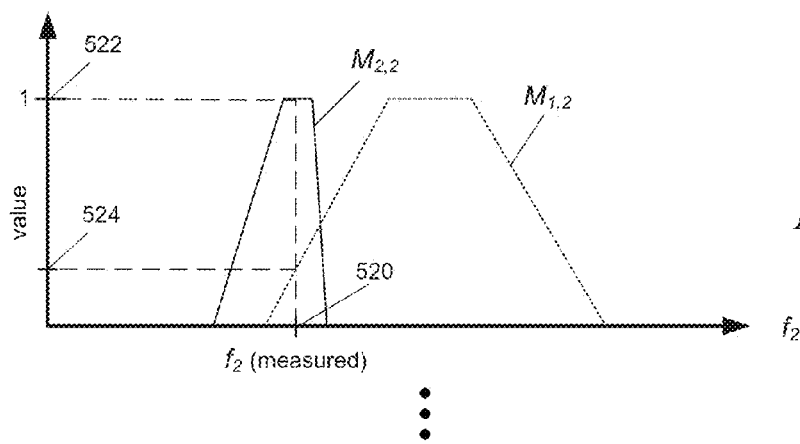
Figure 5C:
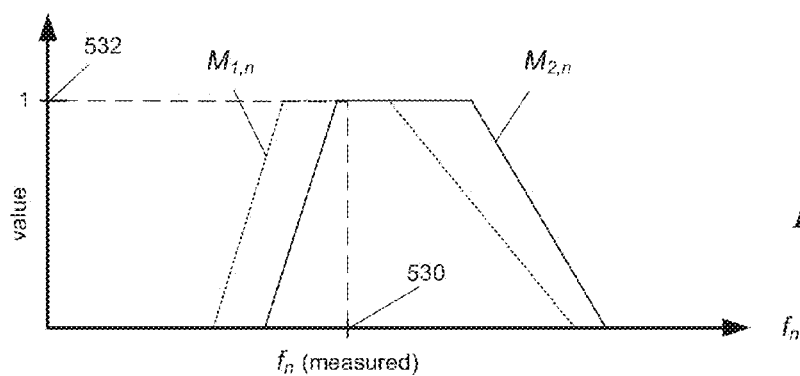

In some embodiments, scores based on the described membership functions may be all-or-nothing, e.g., either a feature $f_n$ is measured and determined to be within the bounds of its corresponding membership function and contribute a score, or may be outside the bounds and contribute nothing. Other embodiments may additionally or alternatively employ membership functions such as those as depicted in FIGS. 5A-5C. The graphs show membership functions $M_{i,j}$ that have been constructed for n characteristic features (denoted by the "j" subscript) and for two activities (denoted by the "i" subscript). The membership functions $M_{i,j}$ may, for example, be constructed from statistical analysis of many measurements, as described above. Though the membership functions are shown as trapezoidal, they may take any suitable shape, e.g., round top, semi-circular, semi-ellipse, Gaussian, parabolic, etc.

In some implementations, when a characteristic feature is measured, e.g., $f_1$ 510, a corresponding value for each activity's membership function for that feature may be determined. For the case shown in FIG. 5A, for example, the second activity's membership function $M_{2,1}$ contributes a value 512 where the first activity's membership function contributes no value. For a second measured feature 520 shown in FIG. 5B, both membership functions may, for example, contribute different values 522, 524. For another measured feature 530 shown in FIG. 5C, both membership functions may, for example, contribute identical values.

In some embodiments, a cost factor $C_i$ may be computed for each candidate activity (denoted by the "i" subscript) based upon detected feature values 510, 520, 530 and the predetermined membership functions $M_{i,j}$ according to the following relation:

$$C_i = \frac{\sum_{j=1}^{n} W_{ij} M_{i,j}(f_j)}{\sum_{j=1}^{n} W_{ij}} \qquad (8)$$

where $W_{i,j}$ represents a weighting factor for the $j^{th}$ feature of the $i^{th}$ activity. The weighting factor may, for example, be selected to emphasize some features and de-emphasize other features for purposes of identifying an activity. In some embodiments, an activity with the highest cost factor $C_i$ may be selected as the identified activity. For example, with reference to FIGS. 5A-5C and considering only the membership functions shown and the measured feature characteristics 510, 520, 530, the second activity $M_2$ would be selected as the identified activity in such embodiments.

In some cases, membership functions may overlap entirely, such that it would not be possible for the inference engine 320 to identify an activity between the two membership functions. This situation might occur, for example, when a new membership function is added to the inference engine 320 for recognition of a new activity not previously recognizable by the inference engine. For example, if the activity monitor 100 is configured to identify biking and is later updated to identify elliptical training activity, a new membership function for identifying elliptical training may entirely overlap with the pre-defined membership function for biking since the two activities are similar.

In some embodiments, membership functions and characteristic features used by the inference engine 320 may be expandable, so that additional characteristic features and associated membership functions can be added to the system. The additional characteristic features and revised membership functions may, for example, be added to distinguish two activities that previously had substantially overlapping membership functions. The addition and updating of membership functions and features can be accomplished, for example, via communication between an intelligent activity monitor 100 with an external device, e.g., a personal computer or computer connected to the internet.

In some embodiments, in addition to or in lieu of recognizing human activities, an intelligent activity monitor 100 may be configured to recognize activities that are not performed by a human, e.g., motion in a clothes dryer (see FIG. 4E), or activities that may be detected when the activity monitor is not supported by a human but is supported by a machine or animal. Such activities may, for example, be detected as an attempt to falsify human activity, and may be referred to herein as "fake" activities, or may be useful in analyzing certain activities such as riding a bicycle when the monitor is place on a wheel of the bike. In some embodiments, inference engine 320 may additionally or alternatively be configured to recognize patterns (e.g., pattern recognition) and/or evaluate membership functions (e.g., fuzzy logic recognition) to identify non-human activities such as motion on a ceiling fan, motion on a wheel of a bicycle or motorized bike, motion in a drying or washing machine. In some instances, an acceleration contribution from gravity may, for example, be tracked to deduce a fake or non-human activity, e.g., the gravitational acceleration contribution changes rapidly from axis to axis. In some implementations, a frequency of cyclic motion may additionally or alternatively be used to deduce a fake or non-human activity, e.g., by determining that the frequency is at a rate higher than humanly possible.

VI. Activity-Specific Data-Processing Engines and Calculation of METS

In some embodiments, once an activity has been identified, data from the feature generator 310, which may include raw accelerometer data, may be routed to an appropriate activity engine 340-m (m corresponding to the value of a selected engine 1, 2, 3, ... n). Each of the activity-specific data processing engines may, for example, use any instance or combination of acceleration-derivative data $D_n$, one or more accelerometer trace data, and characteristic feature data to determine a value of one or more parameters associated with the activity (e.g., speed, distance, number of steps, etc.). In some embodiments, the acceleration-derivative data $D_n$ may additionally or alternatively be used to determine an intensity of the activity (e.g., walking speed, running speed, cadence) and/or other parameters associated with the activity.

As one example and referring to FIG. 4A, the inference engine 320 may identify the activity represented by the data in the figure as walking. Accordingly, multiplexor may, for example, be configured to forward only acceleration-derivative data $D_n$ to a walking activity engine 340-1. Walking activity engine 340-1 may, for example, be configured to determine a distance $T_c$ between a large peak 410, which corresponds to a heel strike, and a successive smaller peak 420, which corresponds to a toe-off in a step. The distance $T_c$ may, for example, represent the contact time of the foot with the ground, from which a walking speed can be determined. An example of a method of determining walking speed from foot contact time is disclosed in U.S. Pat. No. 4,578,769, which in hereby incorporated by reference in its entirety.

In some embodiments, after determining an intensity for an activity, the selected activity engine may additionally or alternatively determine an energy expenditure (e.g., calorie burning rate) for the activity. The energy expenditure may, for example, be determined from a look-up table of metabolic equivalents (METs) for the activity. The look-up table may, for example, comprise a list of metabolic expenditures where each entry may be associated with one or more activity intensity parameters, e.g., step rate, speed, heart rate, etc. A look-up table for each activity that may be performed by a human may, for example, be stored in memory 120 of the activity monitor. In some embodiments, look-up tables for METs may be user-specific, e.g., specific to a user's sex, weight, and height. In some embodiments, over the course of an activity session, an intelligent activity monitor may record calorie burn rates as a function of time and also compute a total number of calories burned as a function of time of the activity. In some embodiments, the activity engine may additionally or alternatively compute other data, e.g., METs/sec, maximum speed, average speed, distance traveled, number of steps, maximum calorie burn rate, time of day etc.

In some embodiments, any data computed by the activity engine 340-m may be provided to data service 360 for subsequent presentation to the user and/or storage in a remote storage device. Additional data may also be stored with data from the activity engine in some embodiments. For example, data identifying the type, date, time, and duration of the activity may be stored in association with the data from the activity engine. In some embodiments, identifying data may be stored as a header associated with a data structure provided by the activity engine.

In some embodiments, an intelligent activity monitor 100 may additionally or alternatively be configured to store in memory user goals (e.g., number of steps per day, distance traveled, an exercise duration for a specific activity). The intelligent activity monitor may, for example, be further configured to provide an audible, visible, or tactile indication to the user when the goal is reached. For example, an intelligent activity monitor may flash LEDs, beep or vibrate when a user has reached a goal of a walking distance within a time interval of a day.

In some embodiments, an intelligent activity monitor 100 may additionally or alternatively be configured to recognize specific motion gestures that a user may execute (e.g., shaking the activity monitor, moving it in a circle with the hand, spinning the activity monitor). An intelligent activity monitor may, for example, include one or more activity engines adapted to recognize such gestures. The recognized gestures may, for example, be used as an interface method for executing specific functions on the activity monitor (e.g., power up, power down, clear data, set a goal, display progress toward one or more goals).

VII. Calibration and Quality of Activity Data

Determining parameters for a motion sensing device that accurately reflect an activity associated with the sensed motion, such as distance and speed of a walking or running person, may be difficult without proper calibration techniques. Thus, in some embodiments, to ensure that an intelligent activity monitor 100 provides data that accurately reflects various parameters associated with the activity, activity-dependent calibration factors may be employed, e.g., such factors may be used by an activity engine 340-m when computing activity-related data from data received from motion detection and preprocessing circuitry. Activity-dependent calibration factors for each activity may, for example, be maintained and updated in memory 120.

In some implementations, calibration factors may be used in one or more equations used by an activity engine 340-m to compute a measure of intensity of the activity. An example of such an implementation is disclosed, for example, in U.S. Pat. No. 4,578,769 (incorporated by reference above) which describes deducing a runner's speed based upon foot contact time that is detected by a sensor placed in footwear. In some embodiments, there may be a number of different calibration factors needed for an activity monitor configured to recognize a number of different activities. Such calibration factors may, for example, be determined ahead of time, e.g., through laboratory testing and experimentation, and then loaded into memory 120 of an intelligent activity monitor 100 prior to its use.

In some embodiments, calibration may be performed in conjunction with a user's review of the data and user input. For example, a user may jog for 2.0 miles and record a time, 14 minutes, 0 seconds (14:00), that it took to jog the two miles. An intelligent activity monitor may, for example, use a pre-defined calibration technique to identify the activity as running and the activity engine 340-m may compute a running pace of 6:50 minutes/mile. In such an implementation, the user may then, via a computer-based interface with the activity monitor, execute a calibration routine wherein the user may first select the identified activity and computed pace, and then enter a known pace for the activity. The system may then adjust or replace an internal calibration factor used by the intelligent activity monitor 100 with a new calibration value for that activity. In this manner, calibrations for various activities can be made specific to individual users of the activity monitor, which may improve the accuracy of the activity monitor for each user.

In some embodiments, an intelligent activity monitor 100 may be additionally or alternatively configured for automatic calibration or self-calibration. Such calibration routines may be executed for one or more recognizable activities. In some implementations, an intelligent activity monitor may be configured for self-calibration for one or more activities. As one example, self-calibration for running will be described. When an intelligent activity monitor is placed on the foot or ankle, the activity monitor will temporarily come to rest along the direction of running (taken as x-directed in this example) as the foot plants on the ground. When the foot is planted, the x-directed velocity of the accelerometer is zero, and this can serve as a reference point for calibration. When the foot next plants, the x-directed velocity returns again to zero. By integrating the x-directed acceleration data twice, a distance between the two successive foot plants can be determined. The distance may be corrected using y- and z-directed acceleration values, since the orientation of the accelerometer changes as the foot moves forward. Once the distance is determined, a time between the foot plants may be determined from an internal clock of the intelligent activity monitor. The time and distance may then be used to calculate a velocity of the runner, or walker. The velocity may be determined from two successive foot plants, or more, to obtain an averaged value, and the process of determining velocity may be repeated at separated intervals of time. In some embodiments, the calculated velocity may be used to update or correct internal calibration values used by an intelligent activity monitor 100. For example, the calculated velocity may be used to correct a calibration value used for estimating running speed based on foot contact time.

Figure 6A:
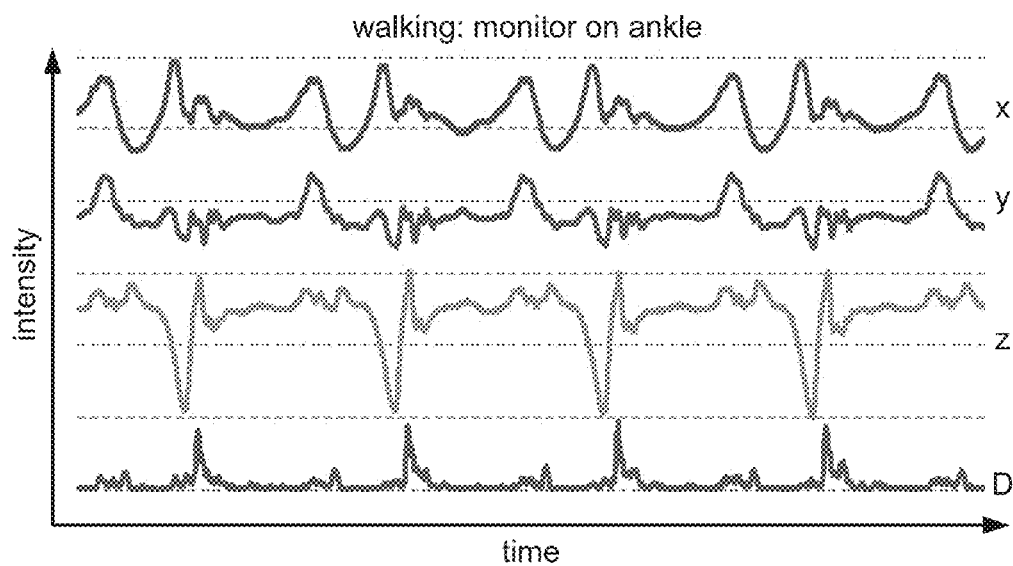
FIGS. 6A-6C depict illustrative examples of multi-axis accelerometer data and combined acceleration-derivative data for a walking activity with the monitor supported at different locations on a subject.
Figure 6B:
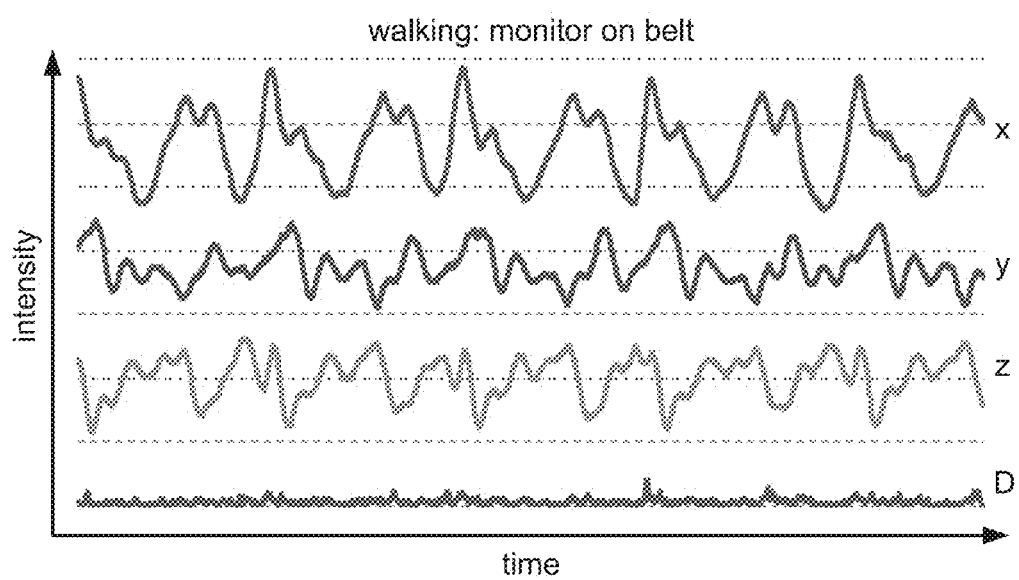

Calibrations may additionally or alternatively be used by the activity monitor in a different manner, and such calibrations may be referred to as location-dependent calibrations. For example and with regard to running or walking without being limited to only these activities, when an intelligent activity monitor 100 is placed on the ankle or foot, for example, a more precise measurement can be made of the activity than if the monitor were worn on the belt or placed in a trouser pocket. This can be seen, for example, in the raw accelerometer data traces of FIGS. 6A-6C. When the monitor is worn on the ankle (FIG. 6A), the z and x waveforms are more pronounced than when the monitor is worn on the belt (FIG. 6B). The timing of the foot strike and/or foot contact time can be determined more accurately using the data from a intelligent monitor worn on the ankle or foot.

In various embodiments, an intelligent activity monitor may additionally or alternatively be configured to recognize a type of activity independent of the location of where the intelligent monitor is worn, and is further configured to identify where the monitor is worn for the activity. Just as the data traces of FIG. 6A can be identified as walking by inference engine 320 as described above, the traces of FIG.

Figure 6C:
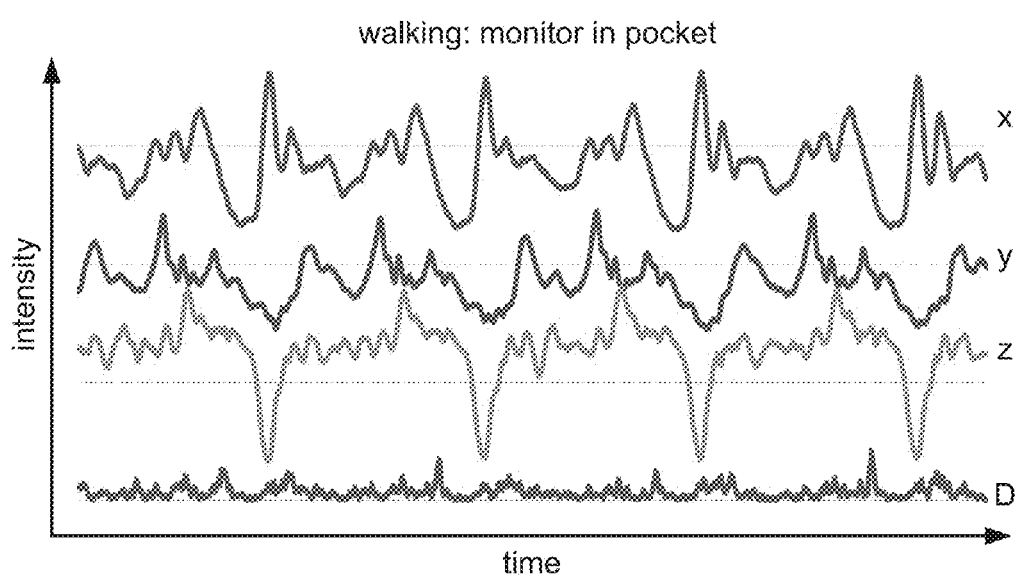

6B may be identified as walking where the monitor is worn on a belt, and the traces of FIG. 6C may be identified as walking where the monitor is located in a pocket. For example, the traces of FIG. 6B may generate characteristic features $f_n$ belonging most closely to one or more membership functions that would identify the activity as "walking, monitor on belt."

In some embodiments, when an activity is identified where an intelligent activity monitor is mounted in a non-optimal location, a different calibration value, or values, may be used by activity engine 340-m to compute an intensity of the activity, according to some embodiments. For example, different calibration values may be associated with each identifiable activity and monitor location. In other embodiments, when an activity is identified where the intelligent activity monitor is mounted in a non-optimal location, information that was gathered from prior use of the intelligent activity monitor in a more optimal location may additionally or alternatively be used to infer or estimate parameters of the activity with the monitor in the non-optimal location. For example, walking data gathered when the activity monitor is worn on an ankle may be used to determine stride lengths that correspond to different walking step frequencies or cadences. Then, when the intelligent activity monitor is worn at a non-optimal location (e.g., a belt or pocket), a detected cyclic frequency or cadence may, for example, be used in conjunction with the previously-obtained data to infer or estimate a stride length for the activity. The estimated stride length may be user-specific. In some implementations, different calibration techniques and/or calibration values may be associated with each identifiable activity and monitor location.

In some embodiments, an activity may additionally or alternatively be identified using the accelerometer traces and/or characteristic features generated from these traces. Once identified, the data may, for example, be qualified or the location of an intelligent activity monitor 100 may be identified using acceleration-derivative data $D_n$. With reference to FIG. 6A, it should be appreciated that, in some embodiments, feature characteristics may be generated from the acceleration-derivative data trace D (e.g., peak values, number of peaks in measurement interval $T_m$) and may be used to identify that the intelligent activity monitor is worn on the foot or ankle and therefore qualify the data as being of high quality. The same feature characteristics generated from the acceleration-derivative data trace D of FIG. 6B may, for example, be used to determine that the intelligent activity monitor is not worn on the foot or ankle and therefore qualify the data as being of low quality. In some embodiments, feature characteristics generated from the acceleration-derivative data alone, or in combination with feature characteristics generated from accelerometer data traces, may be used to identify a particular location of the activity monitor (e.g., belt, trouser pocket, shirt pocket, arm, wrist).

In some embodiments, an intensity value or credit for an activity may additionally or alternatively be reduced by a preselected value when it is recognized that an intelligent activity monitor is located in a non-optimal location. For example and returning to the example of FIGS. 6A-6C, the system may compute an intensity for the activity (walking in this case) in a standard way, but then de-rate the computed intensity (e.g., multiply the computed intensity by a preselected value that would lower the energy expenditure of the user) since the quality of the data is less than optimal. The devaluing of the data may, for example, depend upon the location of the activity monitor, e.g., one value used for a belt location, another value used for a pants pocket location, etc.

In some embodiments, characteristics of an activity may additionally or alternatively be inferred by an intelligent activity monitor from prior high quality data, and an intensity for the activity may be computed accordingly. Returning again to the example of FIGS. 6A-6C, the intelligent activity monitor 100 may, for example, store in memory 120 or provide for storage in an external memory device one or more samples of high quality data (FIG. 6A) when such data is collected and the monitor is worn in an optimal or near optimal location for characterizing the activity. In some embodiments, when the activity is repeated and the inference engine identifies the activity but with the monitor worn in a non-optimal location (FIG. 6B or 6C), the intelligent activity monitor may recall from memory, higher quality data with a cadence that matches the currently sensed activity. The higher quality data may, for example, be repeatedly provided to activity engine 340-m for subsequent processing. As the currently sensed cadence changes, different samples may, for example, be retrieved from storage. In some embodiments, the samples retrieved from storage may depend on additional values of the currently sensed signals other than cadence, e.g., peak values, widths of peaks, minimum values.

In some embodiments, an intelligent activity monitor may additionally or alternatively provide a measure of confidence along with data output by an activity engine 340-m. For example, the monitor may indicate a confidence level in the recognition of the activity (e.g., >90% confidence, >75% confidence, >95% confidence), and may also indicate a level of quality of the data (e.g., best, fair, poor). Confidence may be determined, for example, by how central each measured feature characteristic falls within a membership function, or based upon a calculated value of the cost factor (e.g., value calculated in accordance with EQ. 8) for an activity, or how well a measured pattern matches a reference patter. Quality of the data may be determined, for example, based upon an identified location of the activity monitor when worn by the user during the identified activity. Another form of calibration may additionally or alternatively be implemented in some embodiments, and is referred to herein as "step conversion." Step conversion between different activities based on metabolic equivalents has been studied previously. By way of example, if one were to ride a bicycle there would be no steps, but rather a cadence. Cadence in biking may, for example, be converted to an equivalent number of walking steps through the use of MET equivalents. The concept of MET equivalents for various activities is described, for example, in Ainsworth, B, et al., 2011 *Compendium of Physical Activities: A Second Update of Codes and MET Values*, Medicine & Science in Sports & Exercise, August 2011, which is hereby incorporated by reference in its entirety.

In some embodiments, using the value of the measured activity parameter and a calculated intensity value from the specific exercise, the METs that are calculated for the measured activity (e.g., bicycling) may be translated to an equivalent value (e.g., a number of steps) for another activity (e.g., walking). Furthermore, in some embodiments, the steps and intensity that are so determined may also be translated into relative speed and distance. In some embodiments, such calculations may be performed for any activity where the intensity can be determined by the activity monitor 100. Accordingly, in some embodiments, detection of one activity may be converted to equivalent efforts for other activities.

As described above, in some embodiments, the calibration values, characteristic features, membership functions, and/or computation algorithms used by an intelligent activity monitor 100 may be added and/or revised when the device is interfaced with a computer via transceiver 140. It should thus be appreciated that in such embodiments the intelligent activity monitor may be personalized to become more accurate for a given activity, for a given location of being worn, and/or for a particular user. For example, when the device detects accelerometer data that cannot be recognized by the inference engine 320, the device can log the data along with any related characteristic features generated from the data, the time, and duration of the non-recognized activity. In some embodiments, when subsequently in communication with an external device having a user interface, such as a computer, smart phone, PDA, or similar device, the user may, for example, be queried to identify the intensity, activity, and/or location of the monitor. In such embodiments, the information may, for example, be returned to the device, and a new membership function, features, and/or identification algorithm may be defined for the activity. The membership function and/or identification algorithm may, in some embodiments, be produced external to the activity monitor and downloaded. In some embodiments, one or more new activity engines 340-m may additionally or alternatively be added for the purpose of personalizing an intelligent activity monitor 100.

In some embodiments, an intelligent activity monitor 100 may collect quantifiable information about one's activity, and can identify any one of a plurality of different activities being performed by the user. In some implementations, the intelligent activity monitor may, for example, identify an activity independently of where the activity monitor is worn, and also identify where the monitor is worn for the activity. Further, in some embodiments, the intelligent activity monitor 100 may additionally or alternatively provide quality metrics associated with the sensed data. In some embodiments, the data collection and processing may, for example, be done at low power using data reduction techniques, a variable clock rate microcontroller, and fuzzy logic data processing.

In some embodiments, an intelligent activity monitor 100 may be useful for broad community challenges, allowing for users to be able to readily compare themselves to each other. An intelligent activity monitor may, for example, be used for more accurately handicapping users of different performance capabilities. Some embodiments of the intelligent activity monitor 100 may, for example, allow healthcare providers, insurance companies and employers to more accurately assess fitness levels and exercise regimens of individuals and provide appropriate incentives accordingly.

VIII. Versatile Sensor and Versatile Display Overview

In overview, a versatile sensor may include one or more sensors and be configured to flexibly participate in at least one local area network (LAN). In some embodiments, a versatile sensor may passively participate in a LAN, e.g., eavesdropping to collect data from other sensors in the LAN. In some implementations, a versatile sensor may actively participate in a network, (e.g., forming an ad hoc LAN with one or more sensors, intelligent sensors, and/or versatile sensors), or assume responsibility for and/or control of at least one other sensing device in a network. A versatile display, as depicted in FIG. 1I for example, may include the network functionality of a versatile sensor, but may not include an on-board sensor. A versatile sensor may include all the functionality of an intelligent monitor. In some embodiments, an intelligent monitor may be transformed into a versatile sensor by loading machine-readable instructions onto a microcontroller or microprocessor of the intelligent monitor, wherein the machine-readable instructions adapt the intelligent monitor to perform networking functionality of a versatile sensor.

A versatile sensor may take the physical form of any of the intelligent monitors shown in FIGS. 1B-1H. Accordingly, details of the physical structure of a versatile sensor will not be repeated here. A distinguishing feature of a versatile sensor, or a versatile display, is that the device exhibits greater networking functionality than an intelligent monitor. For example, a versatile sensor may detect other sensors in a network, communicate with other sensors in a network, control at least one other sensor in a network, form an ad hoc network, and/or alter a topology of a network into which the versatile sensor is introduced. A versatile sensor may be configured to sense any one or combination of, but without being limited to, the following types of conditions or parameters: thermal, motion (acceleration, rotation, velocity along or about any of three orthogonal axes), optical, infrared, ultraviolet, environmental (ambient temperature, humidity, atmospheric pressure, wind velocity, ambient light), acoustic, RF signal level, ion, chemical, biological, nuclear radiation, particle, magnetic field, and electric field. A versatile sensor may comprise a sensor component that is configured to output a signal representative of a sensed parameter.

In various embodiments, a versatile sensor may receive data from one or more proximal sensors and process the received data in combination with its own sensor data to provide results that are enriched in informational content and that may more accurately represent a sensed event. The one or more proximal sensors may be in a same network as the versatile sensor, or at least one may be in a different network. A versatile sensor may be added into a network of sensors, and may be configured, in some embodiments, to alter the network topology, e.g., assume control of one or more sensors or become a central hub for the sensors. In some implementations, a versatile sensor may alter its own operation based upon data received from one or more proximal sensors. Versatile sensors, according to some embodiments described below, may be used in industrial settings (e.g., monitoring of a physical plant), automotive or vehicle applications, household applications, medical settings, emergency response settings, and personal health applications.

VIII-A: Network Configurations

According to some embodiments, intelligent sensors, sensors, versatile displays, and versatile sensors may be configured to operate as slave devices in a local area network. In some cases, the local area network may be small, e.g., a piconet, and in some instances the network may be substantially limited to the immediate vicinity of a user or a central hub of the network. A network that is limited in geographic extent to an immediate vicinity of a user is sometimes referred to as a personal local area network (PLAN) or body area network (BAN or body-LAN).

Figure 7:
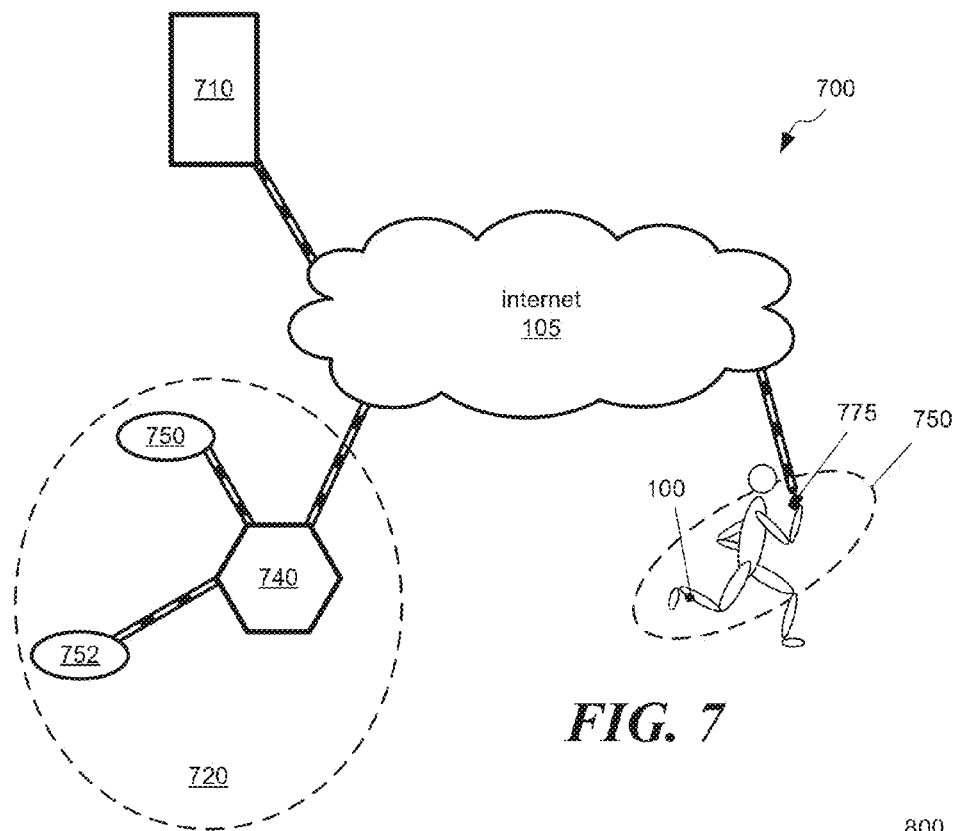
FIG. 7 depicts two examples of small local area networks, each having an optional link to a larger network 105. Each small local area network includes at least one sensor that provides data to a central hub, and may include at least one versatile sensor.

Examples of a piconet 720 and BAN 750 are depicted in FIG. 7. A piconet 720, according to one embodiment, might include a plurality of sensors 750, 752 in a physical plant that are connected within the piconet in a star network configuration with a central hub 740. The central hub 740 may be a computer or microprocessor that is connected to a larger network, e.g., the internet 105, to which is connected one or more servers 710.

An example of a BAN is also depicted in FIG. 7. According to some embodiments, a BAN 750 may comprise an at least one intelligent sensor 100 or versatile sensor supported on a user, and a smartphone 775. In some embodiments, the smartphone 775 may be linked to a larger network, e.g., internet 105. In some implementations, a BAN may comprise a versatile sensor and an intelligent sensor 100 or other sensor. In some embodiments, a BAN may comprise a versatile display 101 and an intelligent sensor 100 or other sensor. It will be appreciated that a BAN may be formed in various ways with a versatile sensor and/or a versatile display.

In some implementations of a piconet or BAN, the sensing devices may be configured as slave devices that report data to a network master or central hub. For example, an intelligent sensor 100 may be a slave to smartphone 775 or a versatile display 101 and regularly or intermittently report data to the smartphone or versatile display.

Figure 8:
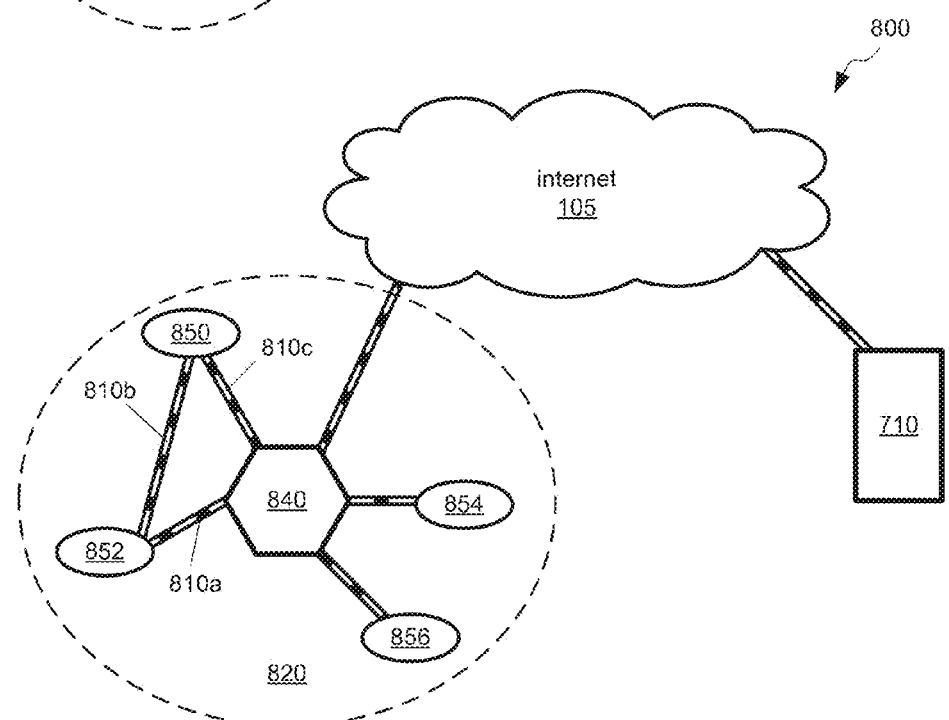
FIG. 8 depicts a small local area network that may contain a versatile sensor and an optional link to a larger network 105, according to some embodiments.

FIG. 8 depicts a small local area network 820 that contains at least one versatile sensor 852, according to an embodiment. The small LAN may be a piconet or a body-area network, and may include a central hub 840 and one or more sensors 850, 854, 856 of various types. Any one or all of sensors 850, 854, 856 may be intelligent or versatile sensors according to some embodiments. The central hub 840 may be a device of higher intelligence than a versatile sensor 852 (e.g., a device having greater processing power) in some embodiments. For example, central hub 840 may be a personal computer, tablet computer, personal digital assistant (PDA), smartphone, or an electronic device with greater processing power than versatile sensor 852. In some implementations, the central hub may be a versatile sensor or a versatile display. In some applications, the small LAN 820 may or may not be connected to a larger or wide area network, e.g., connected to the internet 105 at selected times or substantially all the time. Any of the connections shown in FIG. 8 and the other drawings may be wired or wireless connections.

According to some embodiments, a versatile sensor 852 may be configured, under selected conditions, to communicate with at least one sensor 850 within a network 820. For example, versatile sensor 852 may receive data from sensor 850 and transmit data to sensor 850. Communication may be carried out over a link 810b established between the versatile sensor 852 and sensor 850. The versatile sensor 852 may establish the link after discovering sensor 850 in the network. In some embodiments, the received data may be processed by the versatile sensor 852 and results provided to the central hub 840. In some embodiments, the received data may be processed in combination with data from the versatile sensor so as to enrich the informational content of data provided by the versatile sensor to the central hub, or to affect an operational mode of the versatile sensor and/or an operational mode of sensor 850.

When participating in a network, a versatile sensor 852 may participate as a passive device, e.g., eavesdropping on data communications to obtain additional data), or may be an active participant (e.g., issuing commands to at least one other sensing device in the network). When operating in an eavesdropping manner according to some implementations, a versatile sensor or versatile display may be a passive participant in the network with respect to the sensor 850. Sensor 850 may be completely unaware that another sensor is receiving and acting on data transmitted from the sensor 850. Versatile sensor 852 may receive and process data from sensor 850 so as to enrich the informational content of data provided by versatile sensor 852 to the central hub 840, and yet versatile sensor 852 may not transmit any instructions or data to sensor 850. In such a configuration, versatile sensor 852 may be an eavesdropping peer to sensor 850 and both sensors 850, 852 may be slaves to central hub 840.

Figure 9:
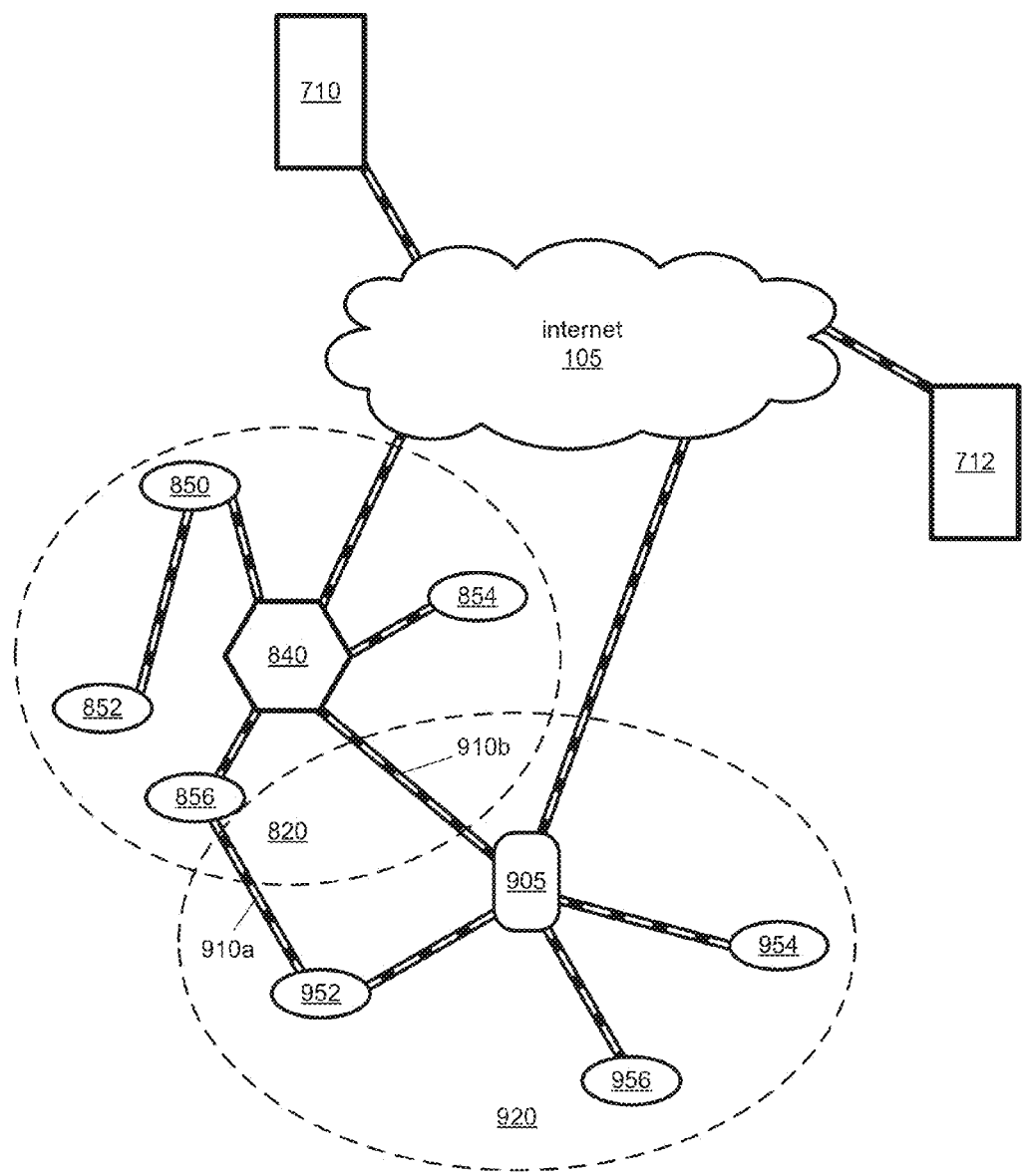
FIG. 9 depicts a versatile sensor in a first network adapted to receive data from a proximal sensor belonging to a second network, according to one embodiment.

FIG. 9 depicts an embodiment in which a versatile sensor 952 belonging to a first network 920 may be configured to receive data from a sensor 856 belonging to a second network 820. As one example, the versatile sensor 952 may comprise an activity monitor that senses motion. In the illustrated example, the first network 920 may be a body area network for which a portable electronic device 905 (e.g., a cell phone, versatile display, PDA, or versatile sensor) serves as a central hub. The BAN 920 may include additional sensors 954, 956 (e.g., a heart-rate sensor, a spirometer, a thermometer, a glucose meter). The second network 820 may be any type of network. As one example, the second network 820 may be a local network for a house or a medical facility. For example, sensor 856 may be a temperature sensor for the local environment. As another example, network 820 may be a piconet for an exercise apparatus or medical equipment. For example, sensor 856 may sense revolutions per minute on an exercise cycle, or may sense blood oxygenation levels. The second network 820 may or may not have a central hub 840, e.g., a personal computer, a microprocessor, a tablet computer, a PDA, that may or may not be configured to communicate directly with central hub 905 of the first network 920 via link 910b.

In some embodiments, versatile sensor 952 or central hub 905 may detect the presence of second network 820 when BAN 920 comes within a communications range of the second network. According to other embodiments, a user may instruct central hub 905 when the BAN 920 is within a range of the second network 820. Central hub 905 may be preprogrammed with information about sensors 850, 852, 854, 856 of the second network or otherwise be adapted to receive user-input information about sensors 850, 852, 854, 856 of the second network. According to some embodiments, versatile sensor 952 may detect information about sensors 850, 852, 854, 856 of the second network, e.g., detect sensor type through identification information included in a data transmission. Regardless of the manner, versatile sensor 952, optionally in combination with central hub 905, may obtain communications protocol information relevant to sensors 850, 852, 854, 856 in the second network 820. The versatile sensor 952 may then listen in, or eavesdrop, to obtain data from at least one sensor 856 in the second network. According to some embodiments, the central hub 905 may instruct versatile sensor 952 to receive information from at least one sensor 856 of the second network 820 via link 910a. Link 910a may be unidirectional in that versatile sensor 952 only receives data from sensor 856. Alternatively, the versatile sensor 952 may elect to receive information from at least one sensor of the second network to enhance its own data.

Versatile sensor 952 may receive and process data from a sensor 856 of the second network. According to some embodiments, versatile sensor 952 may be a passive listener to data transmitted from a sensor of the second network. For example, versatile sensor 952 may not control actions of sensor 856, and control of sensor 856 may remain with the central hub 840 of the second network. It will be appreciated that data received from sensor 856 may be processed by versatile sensor to enrich the informational content of data provided by versatile sensor 952. For example, versatile sensor 952 may comprise an intelligent activity monitor that calculates a caloric burn rate, and sensor 856 may sense ambient temperature. Versatile sensor 952 may compute a high caloric burn rate and receive information that the ambient temperature is high, e.g., greater than 90 F. Versatile sensor may then signal the user to hydrate at a predetermined rate of liquid intake.

In some embodiments, either one or both of LAN 820 and BAN 920 central hub 840 may be in communication with a server 710 on the network. Server 710 may maintain or have access to a list of networks to which it provides services and lists of sensors within each of the networks. Alternatively or in addition, a central hub for a network may provide information about sensors within its network to the server 710 on a periodic basis or as requested by server. In some implementations, a central hub 905 may obtain network and device information about other devices in other networks from a server 710.

There may be one or more servers connected to the internet 105. An internet server 710 may be managed by an organization that provides web-based services to a user of one or more of the sensors in the network 820. For example, in the case of an intelligent activity monitor or versatile sensor, internet server 710 may provide data storage and analysis services, e.g., maintain a log of activities or sensed parameters, process data further to determine additional fitness or health parameters, compare logged data with others or with a user's historical data.

As noted above, a central hub 840, 905 may be a device of higher electronic intelligence (e.g., greater processing power, more memory) than versatile sensor 852. However, in some embodiments, a central hub 840, 905 may comprise a versatile sensor 852, 952. In some implementations, a central hub may have lesser intelligence than a versatile sensor and may comprise a relay device, intermediary, or router that routes data between the network and a server 710. In some implementations, server 710 may comprise hardware and software configured to manage and control sensors within a LAN. In some embodiments, functionality of the central hub may be incorporated on a versatile sensor, and such sensor may manage or control other sensors in the network and effectively act as a central hub for the network.

Additional embodiments of networks and data communications are also possible with the versatile sensors. In another example, there may be multiple versatile sensors in two or more networks. The versatile sensors may be configured to transmit or broadcast data to other versatile sensors in each network that may then receive and process the data.

VIII-B. Network Protocols and Data Handling

Referring again to FIG. 9, in some configurations, data from each sensor 850, 852, 854, and 856 may be supplied to the central hub, and the central hub 840 may transmit data to each of the sensors over links configured in a star network, for example. Data provided to the central hub 840 in a small network may be provided serially to avoid data collisions within the network. In some embodiments, data from the central hub may be broadcast simultaneously to the sensors or may be sent to each sensor separately and serially, e.g., at different points in time. Methods for communicating data between sensors and a central hub are described in further detail in U.S. Pat. No. 7,187,924 filed Feb. 8, 2001, in U.S. patent application Ser. No. 11/799,033 filed Apr. 30, 2007, and in U.S. patent application No. 61/602,819 filed Feb. 24, 2012, each of which are incorporated herein by reference in their entirety.

Communications between any one or combination of sensors 850, 852, 854, 856 and the central hub 840 may be encrypted in some embodiments for security purposes. For example, data may be encrypted prior to transmission using public and private key encryption techniques, Chinese remainder theorem, digital signature, or any other suitable encryption techniques. Received data may be unencrypted by central hub 840, or may be further encrypted by central hub 840 prior to transmission to a server 710. In some embodiments, data within a local network 820 may not be encrypted, and the central hub may encrypt data prior to transmission to a server 710.

The central hub 840 may process data received from one or more sensors, and transmit or store results of the data processing. In some embodiments, central hub 840 may transmit the results via internet 105 to a data server 710 that may store the data and/or provide services back to the central hub and/or a user based on the received data. For example, the user may be a user of an activity monitor, and the server 710 may provide data handling services (e.g., logs, processing of data, etc.). The user may then access the data handling services via the internet using a personal computer or smartphone. In some implementations, the central hub may comprise a smart phone, PDA, tablet computer, personal computer, versatile sensor, or versatile display and may store the results locally for a user's later review or offloading for subsequent data processing.

Figure 10:
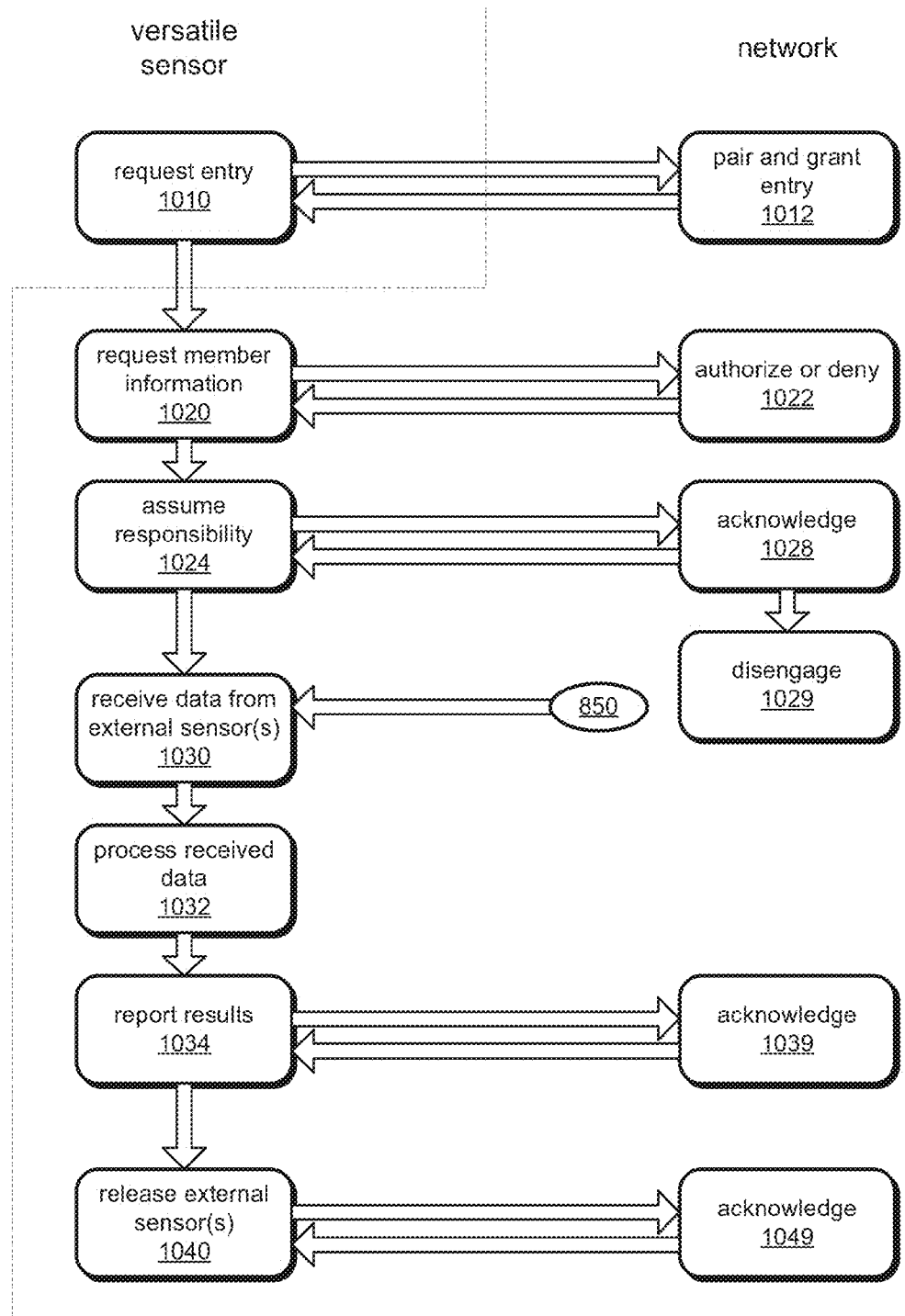
FIG. 10 depicts communication protocols for operation of a versatile sensor within a network, according to some embodiments.

An example of networking protocols and operation of a versatile sensor or versatile display within a network is illustrated in FIG. 10, which may be understood in connection with FIG. 8. The example shown in FIG. 10 is for instructional purposes only, and is not intended to limit the networking functionality of a versatile sensor to only the illustrated acts. In other embodiments, additional or fewer acts of networking may be implemented. The network 820 may be a piconet or body-area network. For purposes of this teaching example and without any intent to limit the type of versatile sensor, the versatile sensor 852 might comprise a heart monitor that is configured to monitor a cardiac pulse and/or electrical activity of a subject's heart. The subject may be an individual in a medical setting or exercise setting. There may be additional sensors in the network 820.

One sensor 850 in the network might be an intelligent activity monitor, as described above in connection with FIGS. 1-3. An intelligent activity monitor may be configured to detect and analyze motion of the subject, e.g., walking, running, biking, and swimming. Another sensor 856 in the network might be an ambient temperature sensor, configured to sense the temperature of the living environment in which the subject is located. Initially, the network 820 may be configured in a star configuration, where activity monitor 850 is only linked to a central hub 840 via link 810c.

According to one embodiment, a versatile sensor 852 may be added to or brought within a network area of piconet or BAN 820. Versatile sensor 852 may request entry 1010 to the network 820. The request may be transmitted to a central hub 840 or an intermediary (not shown) authorized to admit members to the network 820. In some embodiments, the central hub or intermediary may pair 1012 with the versatile sensor (e.g., negotiate communication link protocols) and grant the versatile sensor 852 access to the network 820. A link or channel 810a may be established between the versatile sensor 852 and central hub 840. In some implementations, the central hub or intermediary may deny the versatile sensor 852 access to the network, e.g., if the network is full and cannot handle additional data, or if the versatile sensor fails to provide recognizable data, authorization, and/or interpretable data to the central hub or intermediary.

After admission into the network 820, the versatile sensor 852 may issue a request for member information 1020, e.g., identification of the types of sensors belonging to the network. The central hub 840 or an intermediary may maintain a list of active network members that identifies the type of each device, current communications information that may be used to communicate with each device, and security information that may be used for data encryption and/or decryption when communicating with each device. If the versatile sensor 852 is a trusted device, the central hub or intermediary may authorize 1022 the versatile sensor to obtain greater access to the network, and return all or some of the requested member information to the versatile sensor. The membership information may allow privileged access to information flowing within the network. In some implementations, the central hub 840 or intermediary may deny the versatile sensor privileged access to the network 820 and not return requested membership information.

In some embodiments, a versatile sensor or a versatile display may issue the request directly to one or more sensors in a network, e.g., a broadcast request or an addressed request. Each sensing device in the network may or may not respond to the request. According to some embodiments, a sensing device may respond and provide communications information to the versatile sensor or versatile display, allowing the versatile sensor or versatile display to communicate with and/or control the sensing device.

A versatile sensor 852 or versatile display 101 may review any received member information and make a determination as to whether the versatile sensor or display will receive data from one or more sensors within the network 820, and/or assume control of one or more sensors in the network. Continuing with the example above wherein the versatile sensor comprises a heart monitor, the versatile sensor may elect to receive data from one or both of an intelligent activity monitor 850 and temperature sensor 856 in the network 820. The versatile sensor 852 may be pre-programmed to select certain types of sensors from which to receive data, or may be programmed by a user, or may be instructed by the central hub 840 in some embodiments. Once the versatile sensor has identified the sensor(s) in the network 820 from which to receive data, the versatile sensor 852 may begin receiving data from the identified sensor(s). The versatile sensor may then operate in an eavesdropping manner in which it may monitor data that is being transmitted from the identified sensor(s) to the central hub 840.

According to some embodiments, the versatile sensor 852 may elect to assume responsibility 1024 for one or more sensors within the network. A sensor for which a versatile sensor assumes responsibility may be referred to as a "dependent" sensor herein. Referring to FIG. 8 and continuing with the example above, the versatile sensor may elect to assume responsibility for data from an intelligent activity monitor 850. In some embodiments, the versatile sensor may establish a two-way data link 810b with the dependent intelligent activity monitor and receive all data transmitted from the activity monitor originally intended to be transmitted to the central hub 840. In such a configuration, the versatile sensor may become a master to the activity monitor or sensor 850, and yet remain a slave to central hub 840. Sensor 850 may become a slave to versatile sensor 852, and may temporarily be suspended from a network relationship with central hub 840. Accordingly, a versatile sensor 852 may change its own configuration within a network as well as change the configuration of its dependent sensors. Changes in sensor configurations may be negotiated with a central hub 840 of the network or a server 710.

The versatile sensor 852 may process 1032 the received data (activity data) along with processing its own data (cardiac data), and subsequently transmit 1034 resulting data to the central hub 840. The central hub may acknowledge 1039 receipt of the data. In some cases, the resulting data may include original data received from activity monitor 850 that is effectively passed along by the versatile sensor 852 to the central hub along with any results from processing of the data. The central hub may then process the original data as it normally would have.

In some embodiments, the central hub may pass data processing algorithms to the versatile sensor 852, so that the versatile sensor processes the data from a dependent activity monitor as the central hub would have processed the data. Versatile sensor 852 may then transmit the results of data processing rather than the data as received from the activity monitor. This may alleviate data-processing demands of the central hub 840. Regardless of where the data is processed, the results may comprise information that was obtained based upon a combined processing of the activity data and cardiac data, in some embodiments. For example, results may indicate that a subject's heart rate elevated for a finite period of time due to a transition from a resting and inactive state to a walking or running state.

Responsive to a versatile sensor 852 assuming responsibility for one or more sensors within the network 820, the central hub 840 or an intermediary may acknowledge 1028 the versatile sensor's intentions and, in some embodiments, disengage 1029 from a previously established link with the one or more sensors for which the versatile sensor assumes responsibility. For example and referring to FIG. 8, the central hub 840 may disengage from link 810c. By disengaging from link 810c, the central hub or intermediary may have increased capacity to establish a new data link with another sensor that may be added to the network.

At any time, the versatile sensor 852 may be configured to request a release 1040 of the one or more sensor(s) for which it has assumed responsibility. The release of a sensor may be negotiated with the central hub 840 or intermediary, in some embodiments. For example, the versatile sensor may signal the central hub of its intention to release an intelligent activity monitor 850. The versatile sensor may provide to the central hub any information necessary for central hub 840 to resume a communication link 810c with the activity monitor 850. Once the central hub resumes communications with the activity monitor 850, the central hub may acknowledge 1049 the request to release the monitor after which the versatile sensor 852 may disengage from its data link 810b with the activity monitor 850.

In some implementations, the central hub may not have sufficient capacity to resume communications with a sensor for which the versatile sensor 852 assumed responsibility. The central hub may then be required to terminate another link before resuming communications with the sensor 850 for which a release was requested. The central hub may then issue "wait" signals to the versatile sensor 852 until the central hub 840 terminates a link and re-establishes communications with the activity monitor 850.

In some embodiments, a versatile sensor 852 may alleviate processing burden on a central hub, and expand the sensor capacity within the network. For example, once a versatile sensor 852 assumes responsibility for handling data of another sensor 850 within a network, a central hub for the network may ignore transmissions from the sensor 850 for which the versatile sensor has assumed responsibility. Additionally, the central hub 840 may initiate a new link with a new sensor added to the network, since the central hub has been alleviated of the communication and data-processing obligations for the sensor 850 for which the versatile sensor has assumed responsibility. In some implementations, a versatile sensor 852 may assume responsibility for more than one sensor within a network 820, and thereby enable the central hub 840 to establish new links with more than one new sensor added to the network.

In some implementations, any sensor within a network may transmit or broadcast identifying information that identifies a type of sensor and/or a communication protocol used by the sensor. A versatile sensor may receive the identifying information and maintain a list of sensors within range and/or within a network based upon the received identifying information. The identifying information may be used to establish communications with other sensors within range of the versatile sensor.

According to some embodiments, a server 710 may manage intra- or inter-network sensor configurations and communications. For example, server 710 may instruct a versatile sensor 852 within a network 820 to receive data from and/or assume responsibility for one or more sensors 850 within the local network 820. As another example, server 710 may instruct a versatile sensor 952 of a first network 920 to receive data from a sensor 856 in a proximal network 820. Server 710 may also instruct a versatile sensor to stop receiving data from and/or terminate responsibility for one or more sensors within a network, or stop receiving data from one or more sensors in a proximal network. Instructions issued by server 710 for a versatile sensor may be conveyed via a central hub of the network in which the versatile sensor belongs.

According to some embodiments, a versatile sensor or versatile display may piggy-back data from another sensing device to a central hub, computer, or server. For example, a versatile display may interact with another sensing device, e.g., an intelligent activity monitor, and download stored data from the activity monitor during the interaction. At a later time, the versatile display may establish a connection with a central hub, computer, or server and upload the data.

VIII-C. Sensor Modes of Operation

A versatile sensor 852 may operate in more than one mode in a network, and in some embodiments may alter the modes of operation of its dependent sensors. According to some embodiments, a versatile sensor may be configured to change from a first mode to a second mode of operation based upon information received in data from a dependent sensor and/or upon information obtained from the versatile sensor's own on-board sensing apparatus. In some cases, the modes of operation of the versatile sensor may be distinguished by levels of power consumption. In some instances, the modes of operation of the versatile sensor may be distinguished by data processing algorithms executed. According to some embodiments, a versatile sensor may be configured to alter a mode of operation of one or more dependent sensors based upon information obtained from the versatile sensor's own on-board sensing apparatus. The modes of operation of a dependent sensor may be distinguished by levels of power consumption and/or data processing algorithms executed.

According to one example, a versatile sensor 852 (e.g., a heart rate monitor) may operate in a first mode of operation while processing its own data that is received from on-board sensing apparatus. The versatile sensor may also monitor data received from a dependent sensor 850 (e.g., an activity monitor) in the network. The first mode may be a low-power mode of operation in which the heart-rate monitor samples, processes, and transmits heart-rate data to a central hub 840 at sparse predetermined intervals (e.g., any interval length more than about 5 seconds in some embodiment, more than about 10 seconds in some embodiments, or even longer in some implementations). According to one embodiment, the versatile sensor 852 may remain in the first mode of operation as long as the detected data is within a preselected range, e.g., the heart rate is within a normal heart-rate range for a given sensed activity that may be reported from an intelligent activity monitor.

The versatile sensor may change to a second mode of operation and/or cause a change in mode of operation of one or more of its dependent sensors when actionable data is identified. In some implementations, actionable data may comprise data received from the versatile sensor or a dependent sensor 850 that signals an appreciable change in status of the subject or entity being monitored. For example, a dependent sensor's data may indicate that a user has changed from an inactive state (e.g., sitting or lying) to an active state (e.g., walking, running, biking, etc.). In some implementations, actionable data may comprise data received from the versatile sensor's sensing apparatus, e.g., an indication that the heart rate has changed by a significant amount, e.g., more than about 10% in some embodiments, more than about 20% in some embodiments, more than about 30% in some embodiments, and more than about 50% in some embodiments.

Actionable data may, in some cases, be identified by a versatile sensor after processing the data, e.g., to determine whether a threshold value has been crossed, or whether an allotted amount of time has expired. In other embodiments, actionable data may be tagged by a dependent sensor with a status code. The status code may indicate that the data is within a normal range of values, e.g., a blood glucose level within a normal range, or outside a normal range. A tag associated with data indicating a sensed parameter is outside a normal range, or has changed by a predetermined amount may signal that the associated data is actionable data. A dependent sensor may preliminarily process its own data and tag data for transmission to a versatile sensor.

When the versatile sensor, or a dependent sensor, changes from a first state of operation to a second state, the power consumption and/or processing algorithms of the sensor may change significantly. For example, the level of power consumption may change by more than about 30% in some embodiments, more than about 50% in some embodiments, more than about 100% in some embodiments, and yet more than about 200% in some embodiments. According to some embodiments, a versatile sensor may be operating in a low-power state in which it may sparsely sample its own data and/or data from one or more dependent sensors. The versatile sensor 852 may or may not process data from the dependent sensors in the first mode of operation. In a second mode of operation, the versatile sensor 852 may sample and process its own data and, optionally, data from one or more dependent sensors at higher sampling rates, e.g., reducing one or more sampling intervals to a fraction of their value when sparse sampling was used. The versatile sensor may exhibit higher power consumption, and one or more dependent sensors may exhibit higher power consumption.

As an additional example, a versatile sensor 852 (e.g., a heart-rate monitor) may exit a low-power state upon identifying actionable data that indicates a subject's heart rate has changed by more than a threshold amount. The versatile sensor may then begin receiving and processing data from a dependent sensor (e.g., an activity monitor) to identify whether the subject has changed from a resting state to an active state, and, optionally, to determine what type of activity the subject is undergoing. The versatile sensor may then make a determination as to whether to issue an alarm signal, indicating the subject is in danger, record the data, and/or ignore the change in heart rate.

In some embodiments, a versatile sensor 852 may alter its data processing algorithms responsive to identifying actionable data received from its own sensor or from a dependent sensor. For example, a versatile sensor 852 may receive data from a dependent sensor (e.g., activity monitor) indicating that a subject has changed from a resting state to an active state. The versatile sensor 852 (e.g., heart-rate monitor) may then change the way in which it processes data from its own sensors. For example, instead of processing sensed heart-rate data to determine only inter-beat intervals or heart beats per minute, the versatile sensor may process the data with more complex algorithms to detect arrhythmias or other heart-beat anomalies.

In another example, a versatile sensor may detect an intensity of an activity, and change its and/or a dependent sensors operation mode or modes responsive to the change in activity. For example, an elite athlete may transition from a moderate pace (e.g., a recovery pace) to a fast pace (e.g., a pace near or at a maximal effort for the athlete). The change of pace may be detected by a versatile sensor, which may then issue instructions to collect and process data more frequently. In some implementations, a versatile sensor may be configured to identify the most probably duration or distance over which the pace will be sustained, and recompute pace or other activity/fitness metrics based upon the duration or distance. For example, when a runner changes pace to an intense level, a versatile sensor may recognize for the runner that the new pace is most likely to be sustained for a 400 meter (or 440 yard) interval. The versatile sensor may then change pace calculations from minutes-per-kilometer (or minutes-per-mile) to seconds-per-400-meter (or seconds-per-quarter).

In some embodiments, a versatile sensor may issue an instruction to one or more dependent sensors to change their mode of operation responsive to the versatile sensor detecting actionable data from its own sensed data. For example, a versatile sensor 852 (e.g., heart-rate monitor) may detect a significant change in heart rate. The versatile sensor may then transmit an instruction to dependent sensor 850 (e.g., activity monitor) to wake from a low-power state and collect and transmit activity data. In some implementations, a versatile sensor may also issue an instruction to one or more dependent sensors to place them in a low-power state when full data collection and transmission is no longer needed by versatile sensor.

After identifying actionable data and executing algorithms responsive to the identification of actionable data, a versatile sensor may return to a prior mode of operation, e.g., to a low-power mode of operation. Continuing with one of the examples above, a heart-rate monitor that has changed from a first mode to a second mode of operation upon detecting a significant change in heart rate may determine that the changed heart rate is attributed to a change in activity of the subject and is a normal condition. The heart rate monitor may then return to the first mode of operation.

In some implementations, a versatile sensor may be configured to manage power consumption of and/or communications with dependent sensors. A versatile sensor 852 may be configured to activate, alter, and deactivate any combination of data sampling, data processing, and communication schedules of its dependent sensors. For example, a versatile sensor (e.g., heart-rate monitor) may communicate with and instruct a dependent sensor (e.g., activity monitor) to sample and process data according to a first schedule that is determined by the versatile sensor. The versatile sensor may also instruct the dependent sensor to communicate results of the sampling and processing to the versatile sensor according to a second schedule that is determined by the versatile sensor. The second schedule may be the same or different from the first schedule. For example, the second schedule may have longer intervals of non-activity between collection and communication of data.

According to some embodiments, a versatile sensor may issue an instruction to a dependent sensor to enter a sleep mode when data from that sensor is not needed, e.g., the versatile sensor may detect that a heart-rate or other sensed parameter for a subject has entered a normal steady-state condition. The versatile sensor may issue an instruction to a dependent sensor to exit a sleep mode when data from that sensor is needed, e.g., a heart-rate or other sensed parameter has appreciably changed from a normal steady-state condition and further information is needed to identify a cause of the change.

Although a versatile sensor was primarily described as being a heart-rate monitor in the above examples, in another embodiment the heart-rate monitor may be a dependent sensor and an activity monitor may be configured to operate as a versatile sensor. Additionally, it will be appreciated that the functionalities of versatile sensors, sensor, and intelligent sensors may be utilized in a wide variety of sensing systems, not only those limited to intelligent activity monitors and heart-rate monitors.

IX. Example Fitness/Health Sensing Systems

As may be appreciated from the above descriptions, a versatile sensor 852 or versatile display 101 may provide improvements to data handling, data processing, and power usage in a network of sensors. For example, a versatile sensor may process its own data in conjunction with data from one or more sensors within the network to enrich the informational content of the resulting data provided by the versatile sensor 852 to a central hub 840 or server 710. As one example, a first stationary sensor may be configured to operate as a versatile sensor, in that it may listen for data from other sensors including a mobile versatile sensor. The first stationary sensor may detect a presence or passing by of a versatile sensor, and may exchange data with the versatile sensor when the versatile sensor is within range of the first sensor. The first sensor may report to a central hub that the mobile versatile sensor has come within range of the stationary sensor. Similarly, the versatile sensor may detect the first sensor, and may exchange data with the first sensor. The mobile sensor may also report to its central hub that it passed by the first stationary sensor. Such functionality may be useful in medical facilities, estates, parks, or physical plants (e.g., manufacturing facilities, commercial facilities, etc.)

In a medical facility, an intelligent activity monitor 850 may be attached to a subject receiving care and may be configured as a versatile sensor. There may be stationary health monitoring equipment (e.g., a heart monitor, a sleep monitor, a blood oxygenation sensor, etc.) in a room where the subject is recovering. Monitor lines may be connected to the patient. When the subject becomes mobile, the subject may detach some health monitoring equipment, so that the subject may walk freely. A versatile sensor 852 associated with the health monitoring equipment may receive data from the activity monitor/versatile sensor that indicates that the subject is becoming active and that the subject may be sitting, or standing, or walking. Accordingly, the stationary versatile sensor may report the activity to a central hub, e.g., a nurse's station. In some implementations, the central hub may return a message directed to the activity monitor/versatile sensor or the stationary versatile sensor, e.g., an authorization for detaching monitoring equipment, and optionally to cease certain monitoring operations. The authorization may be communicated to the subject in any suitable way, e.g., tactile vibration, audible signal, visual display.

As the patient moves about the facility, the activity monitor/versatile sensor 850 may listen for other versatile sensors, or other versatile sensors may listen for the activity monitor/versatile sensor. When the activity monitor/versatile sensor 850 is within range of another versatile sensor, the other versatile sensor may communicate with and receive activity data from the subject's activity monitor/versatile sensor. The activity data may be reported to the central hub, and used to establish a record of the subject's progress for the particular walk, as well as for day-to-day progress. The subject's activity monitor/versatile sensor may keep its own record of activity for the subject's benefit. Additionally, the activity monitor may detect versatile sensors and also report, or confirm, that it passed by the versatile sensors.

When a patient returns to a room for rest, health monitoring equipment may detect data from the activity monitor/versatile sensor. The activity monitor/versatile sensor 850 may indicate that the patient has returned to a resting state. The health monitoring equipment and/or the activity monitor may signal the patient so as to prompt the patient to reconnect any monitor lines to the health monitoring equipment that was previously disconnected.

In another example, a versatile sensor (cardiac monitor) may normally monitor inter-beat intervals (IBIs) and blood pressure (BP), according to one embodiment. Should the IBIs adversely change and/or BP become significantly elevated, the versatile sensor 852 may evaluate data from an activity monitor 850 attached to a subject, and determine that the subject has transitioned from a sedentary state (e.g., lying in bed) to an active state (e.g., walking a significant distance from the bed). In such a case, the versatile sensor 852 may report that the subject's heart rate is normal for the condition of walking and also report a duration of walking activity with an average walking heart rate and an average resting heart rate, rather than sounding an alarm responsive to a significant change in heart rate. Conversely, if there is a significant change in IBIs and/or BP with no accompanying sensed change in activity level, then the versatile sensor may issue an alarm signal.

Figure 4F:
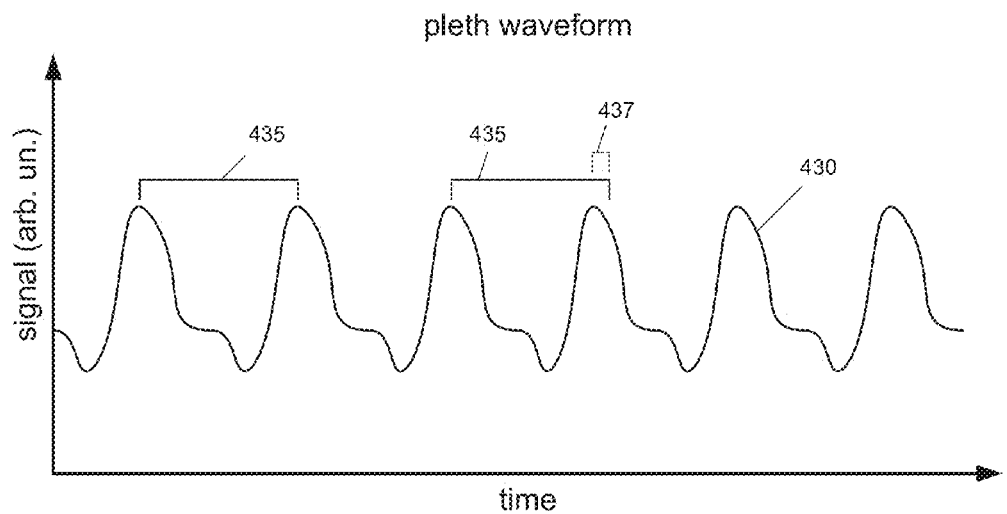
FIG. 4F depicts illustrative examples of pleth waveform data that may be obtained by a fitness sensing system, according to some embodiments.
Figure 4G:
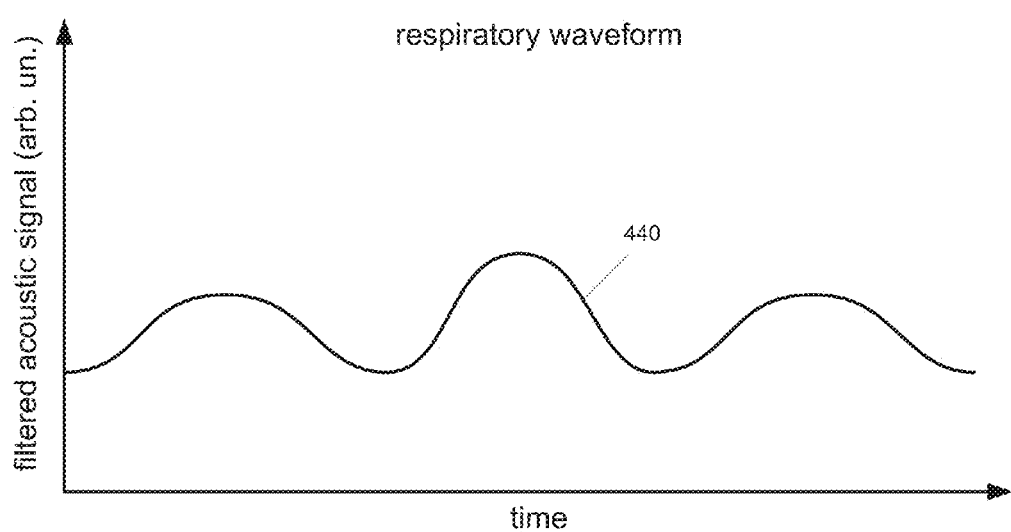
FIG. 4G shows an illustrative example of respiratory waveform data that may be obtained by a fitness sensing system, according to some embodiments.

Referring to FIG. 4F, IBI intervals may be monitored by analysis of a pleth waveform 430 or any suitably-derived waveform that is representative of a subject's cardiac cycle. Inter-beat intervals 435 may be monitored on an average basis in a first mode of operation. For example, and number of beats over a duration greater than about 5 seconds may be used to compute a beats-per-minute value for the subject. In some embodiments, a versatile sensor may, upon detection of actionable data, be configured to further process the data to detect inter-beat variability 437. It has been found that inter-beat variability is typical for a healthy subject, and detection of low inter-beat variability can signal the onset of a harmful cardiac event. Accordingly, a versatile sensor may, upon receipt of actionable data, further process data to detect additional features from the data.

In another example, a versatile sensor may operate in conjunction with a blood glucose meter and receive data from a blood glucose meter. According to some embodiments, the blood glucose meter may utilize IR light to interrogate subcutaneous vessels and provide an approximate blood glucose level. The glucose meter may be incorporated in an intelligent monitor such as that shown in FIGS. 1F-1H or FIGS. 1J-1L. In some implementations, the blood glucose meter may be calibrated periodically by a user following a finger-prick test. The blood glucose meter may detect at some time a high blood sugar level, and signal the user to exercise. An intelligent activity monitor may detect the type and amount of exercise, and signal the user when a sufficient amount of exercise has been performed. In some cases, the detected blood glucose level may be used to automatically set an exercise goal for the user.

Figure 11:
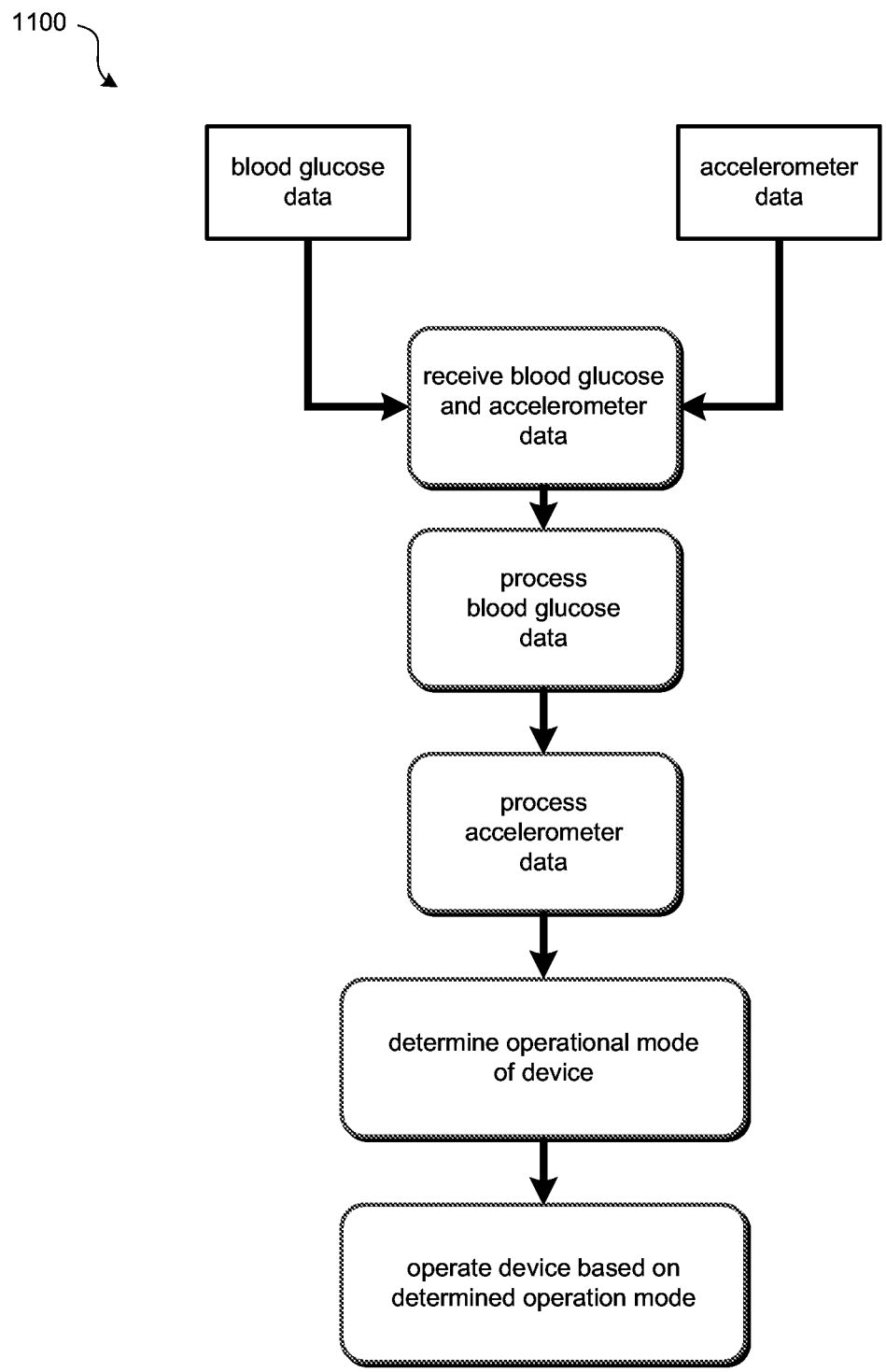
FIG. 11 depicts an example of a process of determining an operational mode of a device.

According to some embodiments, a fitness sensing system may comprise a processor, at least one display, a blood glucose monitor, and an intelligent activity monitor. The intelligent activity monitor may include at least one accelerometer. The blood glucose monitor may be a non-invasive monitor in some embodiments or may be a strip reading monitor in some embodiments. In some implementations, the fitness sensing system may include both a non-invasive blood glucose monitor and a strip reading glucose monitor. The processor may be configured to process first data received from an accelerometer of the fitness sensing system to identify, from among a plurality of different activities, an activity performed by the subject. The processor may further be configured to compute at least one metric representative of the identified activity, and to process second data received from a blood glucose monitor of the fitness sensing system. According to some embodiments, the processor may further be configured to determine an operational mode, from among a plurality of operational modes, for the blood glucose monitor based upon the results of the at least one metric and the processing of the second data. For example, the processor may be configured to place the blood glucose monitor in any one of the plurality of operational modes based upon the processed data from the blood glucose monitor and the data received from the accelerometer. FIG. 11 depicts an example of a process 1100 of determining an operational mode of a device in a fitness sensing system.

In one aspect, the processor, after determining an operational mode, may issue a control signal to a non-invasive blood glucose monitor to change a frequency at which blood glucose measurements are made. For example, the processor may detect a low level of activity of the subject based upon analysis of data from the accelerometer, and issue a control signal to the non-invasive blood glucose monitor to reduce a frequency at which blood glucose measurements are made. In some implementations, the processor may detect a blood glucose level that exceeds a predetermined threshold, and present, via the at least one display, a first signal to the subject to induce the subject to become active or increase a level of activity, e.g., transition from a resting state to a walking state, or walk at a faster pace. The first signal may be an alpha-numeric message displayed on a liquid crystal display, a flashing sequence of one or more LED lights, or a tactile or auditory signal. The processor may then measure an amount of activity performed by the subject subsequent the presenting of the first signal, and present, via the at least one display, a second signal to the subject indicating that the subject has performed a predetermined recommended amount of activity. The recommended amount of activity may be an amount of activity that would be expected to burn a predetermined amount of calories. The caloric burn may be an amount recommended by a health organization for changing a subject's glucose level by a certain amount, or may be an amount determined, by the processor, from historical data for the subject that correlates a change in glucose level with an amount of activity.

In some embodiments, the processor may detect a rate of change of a subject's blood glucose level and compare the rate of change to a stored threshold value. If the rate of change exceeds the stored threshold value, the processor may issue a control signal to the intelligent activity monitor to collect acceleration data at an increased frequency. The processor may then detect an amount of activity performed by the subject, and determine that the rate of change of a subject's blood glucose level is attributed to the activity level of the subject. Accordingly, the processor may not issue an alarm, but may revise a time for which a subsequent glucose measurement, either non-invasive or via a disposable test strip, is to be made or is signaled to the subject.

In some cases, the processor may detect a rate of change of a subject's blood glucose level that exceeds the stored threshold value, and also detect a period of relative inactivity of the subject that encompasses, in time, the detected rate of change of the subject's blood glucose level. In response to detecting both the rate of change of the subject's blood glucose level that exceeds the stored threshold value, and the period of relative inactivity, the processor may present, e.g., via the at least one display, a signal to the subject to induce the subject to perform an invasive blood glucose measurement, e.g., a finger prick to produce a sample on a disposable test strip. In some embodiments, the processor may further execute a calibration process following the invasive blood glucose measurement.

In some embodiments, the calibration process may comprise receiving data from a blood glucose strip reader, wherein the strip reader is controlled by the processor to analyze the test strip. The calibration process may comprise computing, by the processor, a first blood glucose level from data received from the non-invasive blood glucose monitor and further computing a second blood glucose level from data received from the blood glucose strip reader. The calibration process may include comparing, by the processor, the first blood glucose level and the second blood glucose level, and adjusting, by the processor, a scaling factor used by the processor or the non-invasive blood glucose monitor such that the first blood glucose level becomes approximately equal to the second blood glucose level.

According to some embodiments, the fitness sensing system may be further configured to detect, by the processor, data representative of a tapping motion of the accelerometer, and present, via the at least one display, an indication of blood glucose level responsive to the detected tapping. In some implementations, detected tapping motion may cause the processor to present, via the at least one display, an indication of the subject's progress toward an activity goal responsive to the detected tapping.

In some embodiments, a fitness sensing system may be configured to obtain additional data from a non-invasive blood glucose monitor, e.g., plethysmography data, blood oxygenation data, and/or heart-rate data as described above in connection with FIGS. 1J-1L. According to some embodiments, the fitness sensing system may be configured to interrogate, by at least one light source (e.g., at least one source of the non-invasive blood glucose monitor) a region of the subject, and receive, by at least one photodetector, radiation from the at least one light source via the interrogated region of the subject. The received light may be transmitted through the interrogated region of the subject or may be reflected from the interrogated region. Signals from the photodetectors may be analyzed to provide plethysmography data, blood oxygenation data, and/or heart-rate data.

The number of light sources and wavelengths used may be controlled by the processor and dependent on the type of data requested by the processor. For example, to obtain blood glucose data, the processor may issue control signals to multiple light sources operating at respective multiple wavelengths. To obtain heart-rate data, the processor may issue control signals to a fewer number of light sources. In some implementations, the processor may be configured to analyze a plethysmography waveform from data received from the at least one photodetector. The processor may be further configured to compute a blood oxygenation level from the data received from the at least one photodetector. In some embodiments, the processor may compute a fitness metric representative of a fitness level or health of the subject, wherein the fitness metric comprises a measured rate of caloric burn during an activity, a heart rate during the activity, and a blood oxygenation level during the activity.

In some embodiments, the fitness monitor may be configured to activate, by the processor, the blood glucose monitor, and measure, by the at least one light source, a heart rate of the subject for a duration of time determined by the processor. The activation of the blood glucose monitor and duration of time may be determined by the processor based upon a type of activity, intensity level, or amount of activity detected by the processor. The blood glucose monitor may then provide heart rate data representative of the subject's measured heart rate to the processor. In some implementations, the processor may then compute a fitness index value for the subject based at least upon the received heart rate data.

According to some embodiments, power management of a fitness sensing system is structured to conserve power as much as possible, so as to extend the useful life of any on-board battery or batteries. In various embodiments, power management circuitry may be configured to activate sensors at selected times for the recording of physiological and/or activity data. The selected times may be determined dynamically from most recently processed data. As noted above, a fitness sensing system comprising an intelligent activity monitor and a blood glucose monitor may determine, based upon a recent glucose reading and an accrued amount of activity, when to activate the glucose monitor for a subsequent reading. In some cases, a fitness sensing system may determine a preferred time during a physiological cycle to collect sufficient data to characterize the corresponding physiological event with sufficient accuracy. For example, a fitness sensing system may determine a preferred time during a respiratory cycle to collect and process acoustic data to characterize respiratory rate and cycle volume. The preferred time may be a fraction of the cycle occurring around a peak event. For example and with regard to walking or running, the preferred time may occur during foot strike. Measurement techniques for certain activities that may be used or modified for power conservation are described further in U.S. Pat. Nos. 6,298,314, 6,018,705, 6,898,550, 6,493,652, and 7,187,924, all of which are incorporated herein by reference in their entirety.

In a physical plant, an intelligent activity monitor/versatile sensor 850 may be attached to a subject (e.g., a security guard, a facility engineer) that regularly walks through the plant. In the plant may be a plurality of versatile sensors or other sensors, which may be security sensors, safety sensors, operational status sensors, or any combination thereof. The sensors may be stand-alone sensors having limited range wireless communication only, without a need for wired links throughout the plant. When the subject walks through the plant, the subject's activity monitor/versatile sensor 850 may monitor, process, and record data representative of the activity of the subject. Additionally, the activity monitor/versatile sensor 850 may interact with each of the sensors for which it comes in range. In some cases, a stationary versatile sensor may record that the activity monitor/versatile sensor 850 passed through its range. In some embodiments, the activity monitor/versatile sensor may record that it passed through the range of a versatile sensor or other sensor. According to some embodiments, the activity monitor/versatile sensor 850 may be configured to receive a status identification of a versatile sensor or other sensor when it comes within the range of the sensing device. For example, when the subject comes within range of a versatile sensor, the versatile sensor may communicate to the activity monitor/versatile sensor 850 that its status is normal or abnormal. The activity monitor/versatile sensor, upon receiving the status information, may signal the status to the subject using any suitable signaling method, e.g., tactile, audible, visual display.

For personal use, a versatile sensor or versatile display may be configured to communicate with and receive data from devices in a home or at an exercise facility. For example, a scale may include a weight sensor and transmitter configured to transmit an individual's weight to a versatile sensor or versatile display. The versatile sensor may receive and record the weight, when brought within transmission range of the scale (which need not be at the time that the subject steps onto the scale). The versatile sensor may upload the weight data at a later time when the versatile sensor comes within range of a hub. The weight data may be routed to a personal log for the subject.

In some embodiments, a versatile sensor or versatile display may be used to piggy-back data from one or more sensing devices of a network to a central hub or server. Returning to the physical plant example, a subject's activity monitor/versatile sensor 850 may be configured to request and receive logged data from a stationary sensor (which may or may not be configured to operate as a versatile sensor) in the plant when the subject comes within range of the stationary sensor. The data may be uploaded at a later time from the activity monitor/versatile sensor 850 when the activity monitor comes within range of a receiving station for a central hub or server, wherein a link may be established between the receiving station and the activity monitor/versatile sensor 850. According to some embodiments, data may be ported automatically by a versatile sensor without any data uploading or downloading actions required by the user.

When data is piggy-backed by a versatile sensor, the data may be encoded by the originating sensor to include identifying information of the originating sensor. The identifying information may be a unique alpha-numeric string associated with the originating sensor. In some embodiments, a versatile sensor that transports the data may attach its own identifying information. Returning to the example of the scale and a subject's weight above, the scale may first attach identifying information that indicates the data originated from the scale and is representative of a subject's weight. The versatile sensor may add identifying information that indicates the weight data is transported by a particular versatile sensor, that may be associated with a particular subject. Accordingly, the weight may be recorded in a fitness log associated with that particular versatile sensor.

It will be appreciated that similar data transport functionality will be useful in an exercise facility that may have various types of intelligent exercise equipment. A versatile sensor (that may comprise an intelligent activity monitor) may communicate with and receive exercise-related data from each piece of intelligent equipment used by a subject wearing the versatile sensor. In some embodiments, a versatile sensor that can communicate with and receive data from a plurality of different exercise equipment may be beneficial, since the versatile sensor need not be programmed to identify each and every type of exercise activity. Instead, the type of exercise, relevant exercise data, and/or data processing algorithm may be determined by the exercise-specific equipment.

According to some embodiments, a fitness sensing system may comprise a combination of one or more versatile sensors, an intelligent activity monitor (which may be configured as a versatile sensor), and at least one physiological sensor. The physiological sensor may be embodied as one or more high-intensity light sources configured to probe a subject, and one or more photodetectors configured to receive scattered or reflected light from the one or more light sources. In some implementations, the fitness sensing may be disposed in a single wearable band, such as the one depicted in FIGS. 1F-1H.

A fitness sensing system may be configured to compute a fitness metric that is indicative of a subject's overall fitness and/or health level. For example, a versatile sensor may collect activity data, blood oxygenation data, respiratory data, cardiac data, and compute a fitness metric from the combined results. In some embodiments, the fitness metric may be representative of a $VO_2$ max value for the subject or may be a recognized or standardized fitness or health index (HI). According to some embodiments, a fitness metric $F_m$ may be given by the following formula.

$$F_m = \beta \frac{P}{R \times O \times H} \quad (9)$$

In EQ. 9, β represents a proportionality constant, P may represent a pace, or equivalent pace calculated from a different activity via metabolic equivalents, O may represent a blood oxygenation level, R may represent a respiratory rate, and H may represent a heart rate. The fitness metric in EQ. 9 has been formulated such that a higher number indicates a better level of fitness. For example, for a given pace P, an individual with a lower respiratory rate R, lower blood oxygenation O, and lower heart rate H will be a healthier or more fit individual, since he is able to achieve a same pace more efficiently (taxing the cardiovascular system by a lesser amount).

Some embodiments may use other fitness metrics, or a metric where a lower number, rather than a higher number, indicates a better level of fitness. Other factors (e.g., body mass index, blood pressure, resting metabolic rate, caloric burn rate, metabolic rate) may be included in addition to, or alternative to, those shown in EQ. 9. A fitness index such as that shown in EQ. 9 may provide a snapshot of a subject's fitness level and/or health.

A fitness metric may provide one way in which to monitor health conditions of subjects. For example, certain ailments may adversely affect a fitness index for an individual. Ailments that can adversely affect a fitness index include, but are not limited to, COPD, CHF, arthritis, dementia, diabetes, depression, PAD, hypertension, and obesity. In type two diabetes (T2D) there have been studies that indicate that an increase in a subject's $VO_2$ max level directly correlates to reduced dependency in medication. For COPD patients, a fitness index (e.g., $VO_2$ max) may provide a diagnostic marker showing the stage and progress of the disease.

Some studies have shown that physical activity may help correct a disease state, reduce medication, or delay the onset or progress of a disease state. The CDC/HHS recommends moderate to vigorous activity about 150 minutes a week for the normal population. Although some activity monitors may monitor basic parameters of an activity, conventional monitors cannot provide an objective viewpoint or metric as to how well a patient or athlete is progressing on their fitness journey. A fitness sensing system may provide a convenient way to measure and track a subject's fitness level on a daily basis.

There is currently little or no guidance for ailing individuals as to what level of exercise is most effective for their condition. Although workout tables have been generated for various ages, e.g., listing maximum recommended heart rates by age and gender, these tables do not take into account disease states or medication regimens for individuals. Thus, with regard to exercise-based treatment of an ailments, one does not know whether the level of exercise is too little to be effective, or too much to pose an additional health risk. A fitness sensing system can provide data for large populations of users, from which guidelines for exercise may be established based on age, gender, ailment, and stage of ailment.

When treating an ailment, there may be times where medication prescribed to treat a disease causes a detrimental effect on the subject, e.g., lowering the body's ability to metabolize oxygen. Monitoring a fitness index for a subject afflicted with one or more of these ailments may provide a convenient way to effectiveness of various types of treatment, including exercise, and recovery of the subject. For example, a fitness sensing system may allow a physician or individual to see, almost immediately, any impact a prescribed treatment may have on the human engine (heart-lung-circulatory system).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, and/or methods, if such features, systems, articles, materials, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., feature generator 310, preprocessor 305, inference engine 320, activity engines 340-m, and data service 360, and versatile sensor networking functionality, may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

Various aspects of versatile sensors described above may be implemented in hardware, software, firmware, or a combination thereof. For example, any of the operational aspects of the versatile sensor which involve processing data, handling data, and/or communications may be implemented using machine-readable instructions that are executable by a microprocessor and embodied on at least one tangible, computer-readable storage device. The instructions may be executed or placed in operation on a microprocessor or microcontroller of the versatile sensor. In some implementations, instructions may be placed in operation on a central hub or server that operates in combination with operation of a versatile sensor.

The terms "program" or "software" are used herein in a generic sense to refer to any type of computer code or set of computer-executable instructions that can be employed to program a computer or other processor to implement various aspects of the present technology as discussed above. The term "processor" may be used to refer to at least one microprocessor, microcontroller, or any suitable programmable logic device including, but not limited to field programmable gate arrays. Additionally, it should be appreciated that according to one aspect of this embodiment, one or more computer programs that when executed perform methods of the present technology need not reside on a single computer, processor, or microcontroller, but may be distributed in a modular fashion amongst a number of different computers, processors, or microcontrollers to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A system configured to be supported by a subject, the system comprising:

a processor;

a physiological monitor comprising at least one light source arranged to interrogate a region of the subject and at least one photodetector arranged to receive radiation from the at least one light source that has been transmitted through or reflected from the interrogated region, the physiological monitor being configured to operate in a plurality of different monitoring modes in each of which the at least one light source and at least one photodetector are controlled to cause the physiological monitor to monitor a different set of one or more physiological parameters of the subject, wherein at least a first one of the plurality of monitoring modes monitors at least blood oxygenation of the subject and at least a second one of the plurality of monitoring modes monitors at least a physiological parameter selected from the group consisting of: blood glucose, plethysmography, and heart rate; and an activity monitor comprising an accelerometer;

wherein the processor is configured to process data from the accelerometer to compute at least one metric for an activity being performed by the subject, and determine a monitoring mode, from among the plurality of monitoring modes, of the physiological monitor based upon the computed metric for the activity;

wherein the physiological monitor is configured to receive a control signal from the processor that identifies the determined monitoring mode in which the physiological monitor is to operate, and is further configured to operate in the determined monitoring mode in response to the received control signal; and wherein each of the plurality of monitoring modes comprises a mode in which at least one physiological parameter of the subject is monitored based upon at least one measurement made by the physiological monitor while the physiological monitor is in the determined monitoring mode.

2. The system of claim 1, wherein the processor is further configured to present on at least one display an indication of blood glucose level responsive to a user tapping a housing containing the accelerometer.

3. The system of claim 1, wherein the processor is further configured to present on at least one display an indication of the subject's progress toward an activity goal responsive to a user tapping a housing containing the accelerometer.

4. The system of claim 1, wherein the at least one light source comprises at least one laser source for interrogating the region of the subject.

5. The system of claim 1, wherein the second one of the plurality of monitoring modes monitors plethysmography of the subject.

6. The system of claim 5, wherein the processor is further configured to analyze plethysmography waveform data received from the at least one photodetector when the physiological monitor operates in the second one of the plurality of monitoring modes.

7. The system of claim 1, wherein the processor is further configured to compute a blood oxygenation level from the data received from the at least one photodetector when the physiological monitor operates in the first one of the plurality of monitoring modes.

8. The system of claim 7, wherein the processor is further configured to compute a fitness metric representative of a fitness level of the subject, wherein the fitness metric comprises a combination of a measured rate of caloric burn during an activity identified by the processor, a heart rate during the activity, and a blood oxygenation level during the activity.

9. The system of claim 1, wherein the second one of the plurality of monitoring modes monitors heart rate of the subject.

10. The system of claim 9, wherein the processor is further configured to activate the physiological monitor to sense and provide heart rate data to the processor for a selected duration of time.

11. The system of claim 9, wherein the processor is configured to determine inter-beat variability of the subject when the determined monitoring mode monitors heart rate of the subject.

12. The system of claim 1, wherein the processor is further configured to process data from the physiological monitor in combination with the data received from the accelerometer to determine the monitoring mode.

13. The system of claim 1, wherein the processor is further configured to process the data received from the accelerometer to identify, from among a plurality of different activities, an activity performed by the subject and to compute the at least one metric representative of the identified activity.

14. The system of claim 1, wherein the processor is packaged with the physiological monitor separately from the accelerometer.

15. The system of claim 1, wherein processor is further configured to switch the physiological monitor to a power conserving state.

16. The system of claim 1, wherein the second one of the plurality of monitoring modes monitors blood glucose of the subject.

17. A method for operating a system that is configured to be supported by a subject, the method comprising:

processing, by a processor, first data received from an accelerometer of the system;

computing, by the processor, at least one metric for an activity being performed by the subject from the first data;

processing, by the processor, second data received from a physiological monitor comprising at least one light source arranged to interrogate a region of the subject and at least one photodetector arranged to receive radiation from the at least one light source that has been transmitted through or reflected from the interrogated region, wherein the physiological monitor is configured to operate in a plurality of different monitoring modes in each of which the at least one light source and at least one photodetector are controlled to cause the physiological monitor to monitor a different set of one or more physiological parameters of the subject, wherein at least a first one of the plurality of monitoring modes monitors at least blood oxygenation of the subject and at least a second one of the plurality of monitoring modes monitors at least a physiological parameter selected from the group consisting of: blood glucose, plethysmography, and heart rate;

determining, by the processor, a monitoring mode, from among the plurality of monitoring modes, of the physiological monitor based upon the at least one metric, wherein each of the plurality of monitoring modes comprises a mode in which at least one physiological parameter of the subject is determined based upon at least one measurement made by the physiological monitor while the physiological monitor is in the determined monitoring mode;

receiving, at the physiological monitor, a control signal from the processor that identifies the determined monitoring mode in which the physiological monitor is to operate; and operating the physiological monitor in the determined monitoring mode determined by the processor.

18. The method of claim 17, wherein the second one of the plurality of monitoring modes monitors blood glucose of the subject.

19. The method of claim 18, wherein the determined monitoring mode monitors blood glucose and further comprising:

detecting, by the processor, a rate of change of a blood glucose level that exceeds a predetermined threshold; and issuing, by the processor, a control signal to the accelerometer to collect acceleration data at an increased frequency.

20. The method of claim 18, wherein the determined monitoring mode monitors blood glucose and further comprising:

detecting, by the processor, a blood glucose level that exceeds a predetermined threshold;

presenting, via at least one display, a first signal to the subject to induce the subject to increase an activity level;

measuring, by the processor, an amount of activity performed by the subject subsequent the presenting of the first signal; and presenting, via the at least one display, a second signal to the subject indicating that the subject has performed a predetermined recommended amount of activity.

21. The method of claim 18, wherein the determined monitoring mode monitors blood glucose and further comprising:

detecting, by the processor, a rate of change in a blood glucose level that exceeds a predetermined threshold;

detecting, by the processor, a period of inactivity of the subject that encompasses the detected rate of change;

presenting, via at least one display, a signal to the subject to induce the subject to perform an invasive blood glucose measurement using a disposable strip.

22. The method of claim 18, wherein the determined monitoring mode monitors blood glucose and further comprising:

detecting, by the processor, data representative of a tapping motion of the accelerometer; and presenting, via at least one display, an indication of blood glucose level responsive to the detected tapping.

23. The method of claim 17, further comprising:

detecting, by the processor, data representative of a tapping motion of the accelerometer; and presenting, via at least one display, an indication of the subject's progress toward an activity goal responsive to the detected tapping.

24. The method of claim 17, wherein the operating further comprises:

interrogating, by the at least one light source, the region of the subject; and receiving, by the at least one photodetector, radiation from the at least one light source that has been transmitted through or reflected from the interrogated region of the subject.

25. The method of claim 24, wherein the determined monitoring mode monitors plethysmography and further comprising analyzing, by the processor, a plethysmography waveform from data received from the at least one photodetector.

26. The method of claim 24, wherein the determined monitoring mode monitors blood oxygenation and further comprising computing, by the processor, a blood oxygenation level from the data received from the at least one photodetector.

27. The method of claim 26, further comprising:

identifying, by the processor, an activity performed by the subject; and computing, by the processor, a fitness metric representative of a fitness level of the subject, wherein the fitness metric comprises a combination of a measured rate of caloric burn during the activity, a heart rate during the activity, and a blood oxygenation level during the activity.

28. The method of claim 24, wherein the determined monitoring mode monitors heart rate and the operating further comprises:

detecting, with the at least one light source and the at least one photodetector, a heart rate of the subject for a duration of time determined by the processor; and providing, by the physiological monitor, heart rate data representative of the measured heart rate to the processor.

29. The method of claim 28, further comprising:

computing, by the processor, a fitness index value for the subject based at least upon the received heart rate data.

30. The method of claim 17, further comprising processing the second data from the physiological monitor in combination with the first data to determine the monitoring mode.

31. The method of claim 17, further comprising:

processing, by the processor, the first data to identify, from among a plurality of different activities, an activity performed by the subject; and computing, by the processor, the at least one metric representative of the identified activity.

32. The method of claim 17, wherein the second one of the plurality of monitoring modes monitors plethysmography of the subject.

33. The method of claim 17, wherein the second one of the plurality of monitoring modes monitors heart rate of the subject.

* * * * *

UNITED STATES PATENT AND TRADEMARK OFFICE
CERTIFICATE OF CORRECTION

PATENT NO. : 9,734,304 B2  
APPLICATION NO. : 13/840098  
DATED : August 15, 2017  
INVENTOR(S) : Blackadar et al.

Page 1 of 1

It is certified that error appears in the above-identified patent and that said Letters Patent is hereby corrected as shown below:

On the Title Page

Item (72) Inventor is corrected to read:
-- Thomas P. Blackadar, Natick (MA);
David P. Monahan, West Chester (PA);
Thomas J. Quinlan, Stow (MA);
Paul J. Gaudet, Dracut (MA);
Norbert Ohlenbusch, Andover (MA);
Jerry Zhang, Westborough (MA) --.

Signed and Sealed this
Eighth Day of October, 2019

Andrei Iancu
*Director of the United States Patent and Trademark Office*